(12) United States Patent
Walsh et al.

(10) Patent No.: US 10,151,754 B2
(45) Date of Patent: Dec. 11, 2018

(54) CELL SURFACE PROSTATE CANCER ANTIGEN FOR DIAGNOSIS

(71) Applicant: MINOMIC INTERNATIONAL LTD., Macquarie Park (AU)

(72) Inventors: Bradley Walsh, Turramurra (AU); Douglas Campbell, North Sydney (AU); Irene Justiniano Fuenmayor, St Ives (AU); Aline Nocon, Leichardt (AU); Julie Soon, North Bondi (AU); Quach Truong, Leichardt (AU); Sandra Wissmueller, Currans Hill (AU); Pamela Russell, Surfers Paradise (AU)

(73) Assignee: Minomic International Ltd., New South Wales (AU)

( * ) Notice: Subject to any disclaimer, the term of this patent is extended or adjusted under 35 U.S.C. 154(b) by 153 days.

(21) Appl. No.: 15/111,973

(22) PCT Filed: Jan. 16, 2015

(86) PCT No.: PCT/AU2015/000018
§ 371 (c)(1),
(2) Date: Jul. 15, 2016

(87) PCT Pub. No.: WO2015/106311
PCT Pub. Date: Jul. 23, 2015

(65) Prior Publication Data
US 2016/0349263 A1    Dec. 1, 2016

Related U.S. Application Data

(60) Provisional application No. 61/928,776, filed on Jan. 17, 2014.

(51) Int. Cl.
*G01N 33/574*    (2006.01)
*C07K 16/30*    (2006.01)

(52) U.S. Cl.
CPC ....... *G01N 33/57434* (2013.01); *C07K 16/30* (2013.01); *C12Y 304/21077* (2013.01); *C07K 2317/34* (2013.01); *G01N 2333/705* (2013.01); *G01N 2333/96455* (2013.01); *G01N 2400/40* (2013.01)

(58) Field of Classification Search
None
See application file for complete search history.

(56) References Cited

U.S. PATENT DOCUMENTS

| | | | |
|---|---|---|---|
| 3,645,852 A | 2/1972 | Axen et al. | |
| 3,691,016 A | 9/1972 | Patel et al. | |
| 3,720,760 A | 3/1973 | Bennich et al. | |
| 3,969,287 A | 7/1976 | Jaworek et al. | |
| 4,195,128 A | 3/1980 | Hildebrand et al. | |
| 4,229,537 A | 10/1980 | Hodgins | |
| 4,247,642 A | 1/1981 | Hirohara | |
| 4,330,440 A | 5/1982 | Ayers et al. | |
| 4,376,110 A | 3/1983 | David et al. | |
| 5,622,836 A | 4/1997 | Walker et al. | |
| 6,116,013 A | 9/2000 | Moeller | |
| 7,960,517 B2 | 6/2011 | Couto et al. | |
| 7,985,560 B2 | 7/2011 | Valkirs et al. | |
| 2003/0077282 A1 | 4/2003 | Bigler et al. | |
| 2013/0224209 A1* | 8/2013 | Wang | C12Q 1/6886 424/139.1 |

FOREIGN PATENT DOCUMENTS

| | | |
|---|---|---|
| CN | 101918836 A | 12/2010 |
| WO | WO 2008-140774 A2 | 11/2008 |
| WO | WO 2013-119964 A2 | 8/2013 |

OTHER PUBLICATIONS

Whipple et al, TheScientificWorldJournal, 8, 1250-1253, 2008.*
Aikawa et al., "Glypican-1 modulates the angiogenic and metastatic potential of human and mouse cancer cells", Journal of Clinical Investigation, 2008, vol. 118(1):89-99.
Ambrosini-Spaltro, Andrea, "Immunohistochemical and Molecular Prognostic/Predictive Markers in Neoplastic Diseases", Doctoral Dissertation, University of Bologna, 2012, 60 pages.
Dainak et al., "Methods in Cell Separations", Adv Biochem Engin/Biotechnol, 2007, vol. 106:1-18.
David et al., "Molecular Cloning of a Phosphatidylinositol-anchored Membrane Heparan Sulfate Proteoglycan from Human Lung Fibroblasts", The Journal of Cell Biology, 1990, vol. 111:6-2, 3165-3176.
Duan et al., "GPC-1 may serve as a predictor of perineural invasion and a prognosticator of survival in pancreatic cancer", Asian Journal of Surgery, 2013, 36(1):7-12.
Filmus et al., "Glypicans", Genome Biology, 2008, 9:224, 6 pages.
Filmus et al., "Glypicans: proteoglycans with a surprise", J. Clin Invest, 2001, 108:497-501.
Fujise et al., "Daily regulates Dpp morphogen gradient formation in the *Drosophila* wing", Development, 2003, 130:1515-1522.
Han et al., "*Drosophila* glypicans control the cell-to-cell movement of Hedgehog by a dynamin-independent process", Development, 2004, 131(3):601-611.
Hoffman et al., "Prostate-specific antigen testing accuracy in community practice", BMC Family Practice, 2002, 3:19.

(Continued)

*Primary Examiner* — Mark Halvorson
(74) *Attorney, Agent, or Firm* — Baker & Hostetler LLP

(57) ABSTRACT

The present invention provides compositions and methods of detecting prostate cancer in the body fluids or tissues of patients. Prostate cancer is detected by measuring the level of glypican-1 in a body fluid sample. In one embodiment prostate cancer is detected by contacting a body fluid sample with an anti-glypican-1 antibody, such as MIL-38. The invention includes kits for detection of prostate cancer in a body fluid sample, comprising an anti-glypican-1 antibody and glypican-1 standards.

18 Claims, 17 Drawing Sheets
Specification includes a Sequence Listing.

(56) References Cited

OTHER PUBLICATIONS

Hollinger et al., "Engineered antibody fragments and the rise of single domains", Nature Biotechnology, 2005, 23(9):1126-1136.

Kleeff et al., "The Cell-surface Heparan Sulfate Proteoglycan Glypican-1 Regulates Growth Factor Action in Pancreatic Carcinoma Cells and Is Overexpressed in Human Pancreatic Cancer", J. Clin. Invest., 1998, vol. 102(9):1662-1673.

Kohler et al., "Continuous cultures of fused cells secreting antibody of predefined specificity", Nature, 1975, 256:495-497.

Matsuda et al., "Glypican-1 is overexpressed in human breast cancer and modulates the mitogenic effects of multiple heparin-binding growth factors in breast cancer cells", Cancer Research, 2001, 61(14):5562-5569.

Obort et al., "Prostate-specific antigen: Any successor in sight?", Reviews in Urology, 2013, 15(3):97-107.

Orfao et al., "General Concepts About Cell Sorting Techniques", Clinical Biochemistry, 1996, vol. 29(1):5-9.

Posthumus et al., "Analysis and Simulation of a Neutralizing Epitope of Transmissible Gastroenteritis Virus", Journal of Virology, 1990, 64(7):3304-3309.

Qiao et al., "Heparan Sulfate Proteoglycans as Regulators of Fibroblast Growth Factor-2 Signaling in Brain Endothelial Cells: Specific Role for Glypican-1 in Glioma Angiogenesis", The Journal of Biological Chemistry, 2003, 278(18):16045-16053.

Rotmans et al., "Cross-Linking of *Schistosoma mansoni* Antigens and their covalent binding on the surface of polystyrene microtitration trays for use in the ELISA", Journal of Immunological Methods, 1983, 57:87-98.

Russell et al., "Immunohistochemical characterisation of the monoclonal antibody BLCA-38 for the detection of prostate cancer", Cancer Immunology, Immunotherapy, 2004, 53(11):995-1004.

Su et al., "Glypican-1 is frequently overexpressed in human gliomas and enhances FGF-2 signaling in glioma cells", The American Journal of Pathology, 2006, 168(6):2014-2026.

Suhovskih et al., "Proteoglycan Expression in Normal Human Prostate Tissue and Prostate Cancer", ISRN Oncology, 2013, vol. 2013, Article ID 680136, 9 pages.

Timmerman et al., "Functional reconstruction and synthetic mimicry of a conformational epitope using CLIPS™ technology", Journal of Molecular Recognition, 2007, 20:283-329.

Tung et al., "Modern Flow Cytometry: A Practical Approach", Clinics in Laboratory Medicine, 2007, vol. 27(3):453-468.

Veugelers et al., "Glypican-6, a new member of the glypican family of cell surface proteoglycans", J. Biol Chem, 1999, 274(38):26968-26977.

Walker et al., "Detection of malignant cells in voided urine from patients with bladder cancer, a novel monoclonal assay", Journal of Urology, 1989, 142(6):1578-1583.

Whipple et al., "A $Kras^{G12D}$-driven Genetic Mouse Model of Pancreatic Cancer Requires Glypican-1 for Efficient Proliferation and Angiogenesis", Oncogene, 2012, 31(20):2535-2544.

Wissmueller et al., "Development of an antibody based test for the diagnosis of prostate cancer", BJU International (Mar. 2014) vol. 113, Supp. 4, pp. 45, Abstract No. 90. $67^{th}$ Annual Scientific Meeting of the Urological Society of Australia and New Zealand, Brisband, QLD, Australia, Mar. 16, 2014-Mar. 19, 2014. (whole document).

Bortell et al., "Nicotinamide Adenine Dinucleotide (NAD) and Its Metabolites Inhibit T Lymphocyte Proliferation: Role of Cell Surface NAD Glycohydrolase and Pyrophosphatase Activities", The Journal of Immunology, 2001, 167, 2049-2059.

van Hal et al., "Evaluation of Soluble CD44v6 as a Potential Serum Marker for Head and Neck Squamous Cell Carcinoma", Clinical Cancer Research, 1999, 5, 3534-3541.

Weber et al., "Adiponectin Downregulates Galectin-3 Whose Cellular Form is Elevated Whereas its Soluble Form is Reduced in Type 2 Diabetic Monocytes", FEBS Letters, 2009, 583, 3718-3724.

\* cited by examiner

GPC1_HUMAN  Mass: 61,641  Score: 4278  Matches: 166(134)  Sequences: 21(18)  emPAI: 5.60
Glypican-1 OS=Homo sapiens GN=GPC1 PE=1 SV=2

Sequence Coverage: 46%

Matched peptides are underlined

1  MELRARGWWL  LCAAAALVAC  ARGDPASKSR  SCGEVRQIYG  AKGFSLSDVP
 51  QAEISGEHLR  ICPQGYTCCT  SEMEENLANR  SHAELETALR  DSSRVLQAML
101  ATQLRSFDDH  FQHLLNDSER  TLQATFPGAF  GELYTQNARA  FRDLYSELRL
151  YYRGANLHLE  ETLAEFWARL  LERLFKQLHP  QLLPDDYLD  CLGKQAEALR
201  PFGEAPRELR  LRATRAFVAA  RSFVQGLGVA  SDVVRKVAQV  PLGPECSRAV
251  MKLVYCAHCL  GVPGARPCPD  YCRNVLKGCL  ANQADLDAEW  RMLLDSWLI
301  TDKFWGTSGV  ESVIGSVHTW  LAEAINALQD  NRDTLTAKVI  QGCGNPKVNP
351  QGPGPEEKRR  RGKLAPRERP  PSGTLEKLVS  EAKAQLRDVQ  DFWISLPGTL
401  CSEKMALSTA  SDDRCWNGMA  RGRYLPEVMG  DGLANQINNP  EVEVDITKPD
451  MTIRQQIMQL  KIMTNRLRSA  YNGNDVDFQD  ASDDGSGSGS  GDGCLDDLCS
501  RKVSRKSSSS  RTPLTHALPG  LSEQEGQKTS  AASCPQPPTF  LLPLLLFLAL
551  TVARPRWR        (SEQ ID NO: 23)

Figure 1

Mass Spectrometry of Size Exclusion HPLC Fraction #29

GPC1_HUMAN    Mass: 61641    Score: 290    Matches: 8(8)    Sequences: 8(8)    emPAI: 0.52
Glypican-1 OS=Homo sapiens GN=GPC1 PE=1 SV=2

Sequence Coverage: 14%

Matched peptides are underlined

```
  1  MELRARGWWL LCAAAALVAC ARGDPASKSR SCGEVRQIYG ARGFSLSDVP
 51  QAEISGEHLR ICPQGYTCCT SEMEENLANR SHAELETALR DSSRVLQAML
101  ATQLRSFDDH FQHLLNDSER TLQATFPGAF GELYTQNARA FRDLYSELRL
151  YYEGANLHLE ETLAEFWARL LERLFKQLHP QLLIPDDYLD CLGKQAEALR
201  PFGEAPRELR LRATRAFVAA RSFVQGLGVA SDVTRKVRQY PLGPECSRAV
251  MKLVYCAHCL GVPGARPCPD YCRNVLRGCL AMQADIDAEW RNLLDSMVLI
301  TDKFWGTSGV ESVIGSVHTW LAEAINALQD NRDTLTAKVI QGCGNPKVNP
351  QGPGEEKRR RGKLAPRERP PSGTLEKLVS EAKAQLRDVQ DFWISLPGTL
401  CSEKMALSTA SDDRCWNGMA RGRYLPEVMG DGLANQINNP EVEVDITKPD
451  MTIRQQINML KIMTMRLRSA YNGNDVDFQD ASNDSGSGSG GDGCLDDLCS
501  RKVSRKSSSS RTPLHALPG LSEQEGQKTS AASCPQPFZE LLFLLFLAI
551  TVAEKWR   (SEQ ID NO: 23)
```

Figure 3

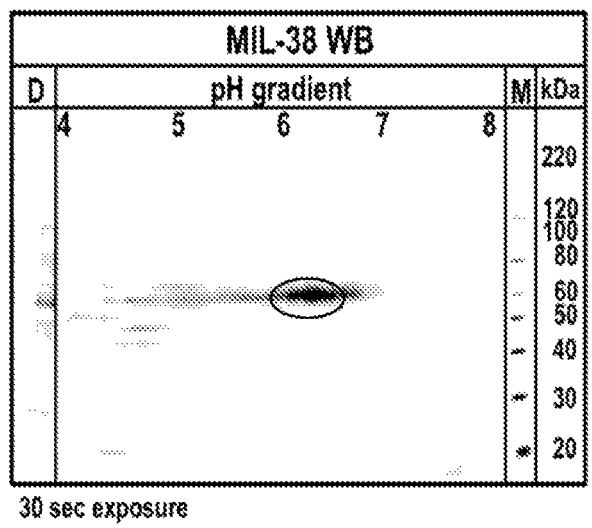
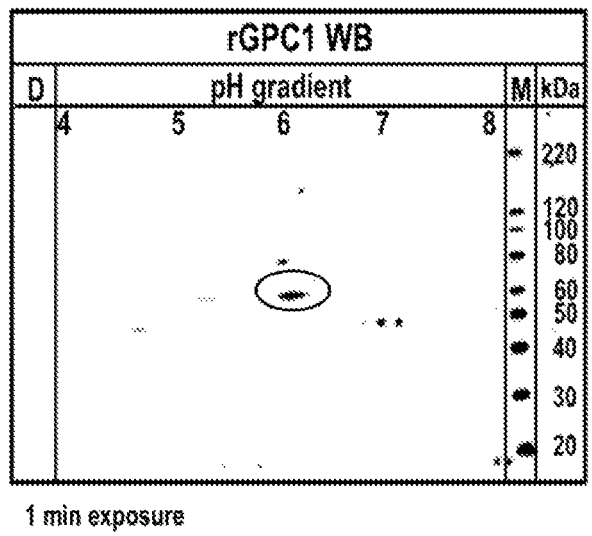
Figure 4

A

GPC1_HUMAN    Mass: 61641    Score: 852    Matches: 30(22)    Sequences: 11(9)    emPAI: 0.69
Glypican-1 OS=Homo sapiens GN=GPC1 PE=1 SV=2

Sequence Coverage: 16%

Matched peptides are underlined

```
  1  MELRARGWWL  LCAAAALVAC  ARGDPASKSR  SCGEVRQIYG  AKGFSLSDVP
 51  QAEISGEHLR  ICPQGYTCCT  SEMEENLANR  SHAELETALR  DSSRVLQAML
101  ATQLRSFDDH  FQHLLNDSER  TLQATFPGAF  GELYTQNARA  FRDLYSELRL
151  YYRGANLHLE  ETLAEFWARL  LERLFKQLHP  QLLPDDYLD   CIGKQAEAIR
201  PFGEAPRELR  LRATRAFVAA  RSFVQGLGTA  SDVRKTVRQV  PLGPECSRAV
251  MKLVYCAHCL  GVPGARECPD  YCRNVLKGCL  AAQADLDAEW  RNLLDSWVLI
301  TDKFWGTSGV  ESVIGSVHTW  LAEAINALQD  MRDITAKVI   QGCGMPFVNP
351  QGPGPEEKRR  RGKIAPRERP  PSGTLEKLVS  EAKAQLRDVQ  DEMISLPGTL
401  CSEKMALSTA  SDDRCWNGMA  RGRYLPEVMG  DGLAMQIWNP  EVEVDITKPD
451  MTIRQQIMQL  KIMTNRLRSA  YNGNDVDFQD  ASDDGSGSGS  GDGCLDMLCS
501  RKVSRKSSSS  RTPLTHALPS  LSEQEGQKTS  AASCPQPPTF  LIPLLLFLAL
551  TVAREWWR (SEQ ID NO: 23)
```

Figure 8

GPC1_HUMAN    Mass: 61641    Score: 1531    Matches: 48(43)    Sequences: 11(10)    emPAI: 1.42
Glypican-1 OS=Homo sapiens GN=GPC1 PE=1 SV=2

Sequence Coverage: 18%

Matched peptides are underlined

1 MELRARGWWL LCAAAALVAC LCAAAALVAC ARGDPASKSR SCGEVRQIYG AKGFSLSDVP
 51 QAEISGEHLR ICPQGYTCCT SDMEEMLANR SHAELETALR DSSRVLQAML
101 ATQLRSFDDH FQHLLNDSER TLQATFPGAF GELITQMARA FRDLYSELRL
151 YYRGANLHLE ETLAEFWARL LERLFKQLHP QLLLPDDYLD CLGKQARAIR
201 PFGEAPRELR LRATRAFVAA RSFVQGLGVA SDVVRKVAQV PLGPECSRAV
251 MKLVYCAHCL GVPGARPCPD YCRNVLKGCL AMQADLDAEW RNLLDSMLLI
301 TDKFWGTSGV ESVIGSVHTW LAEAINALQD NRDTLTARVI QGCGNPKVMP
351 QGFGPEEKRR RGKLAPRERP PSGTLEKLVS EAKAQLRDVQ DFWISLPGTL
401 CSEKMALSIA SDDRCWNGMA RGRYLPEVMG DGLAMQIMNP EVEVDITKPD
451 MTIRQIMQL KIMTNRLRSA YNGNDVDFQD ASDNGSGSGS GDGCLDDLCS
501 RKVSRKSSSS RTPLTHALPG LSEQEGQKTS AASCPQPTTF LLPLLIFLAI
551 TVARFRWR (SEQ ID NO: 23)

Figure 8

GPC1_HUMAN    Mass: 61681    Score: 1364    Matches: 59(55)    Sequences: 13(9)    emPAI: 1.18
Glypican-1 OS=Homo sapiens GN=GPC1 PE=1 SV=2

Sequence Coverage: 24%

Matched peptides are underlined

1    MELRARGWWL   LCAAAALVAC    ARGDPASKSR    SCGEVRQIYG    AKGFSLSDVP
51   QAEISGEHLR   ICPQGYTCCT    SEMEENIANR    SHAELETALR    DSSRVLQAML
101  ATQLRSFDDH   FQHLLNDSER    TLQATPGAF    GELYTQNARA    FRDLYSELRL
151  YYRGANLHLE   ETLAEFWARL    LERLFKQLHP    QLLFDDTLD    CLGKQAEAIR
201  PFGEAFRELR   LRATRAFVAA    RSFVQGLGVA    SDVVRKVAQV    PLGFECSRAV
251  MKLVYCAHCL   GVPGARPCPD    YCRNVLKGCL    ANQADIDAEW    RMLLDSMVLI
301  TDKFWGTSGV   ESVIGSVHTW    LAEAIMALQD    MRDCLIAKVI    QGCGMFRVNP
351  DGPGPEEKRR   RGKIAFRERP    PSGIEKLVS    EARAQLRDVQ    DFWISLPGTL
401  CSERMALSTA   SDDRCWNGMA    RSRYLPEVMG    DGLANQIRNP    EVEVDITKPD
451  MTIRQQIMQL   KIMTNRLRSA    YNGNDVDFQD    ASDDFSGSGS    GDGCIDDLCS
501  RKVSRKSSSS   RTPLTHALPG    LSEQEGQRTS    AASCQPPTF    LLFLLLTLAL
551  TVARFBWR    (SEQ ID NO: 23)

Figure 8

SEQUENCE LISTING

```
<160> NUMBER OF SEQ ID NOS: 24

<210> SEQ ID NO 1
<211> LENGTH: 1677
<212> TYPE: DNA
<213> ORGANISM: Homo sapiens

<400> SEQUENCE: 1
atggagctcc gggcccgagg ctggtggctg ctatgtgcgg ccgcagcgct ggtcgcctgc      60
gcccgcgggg acccggccag caagagccgg agctgcggcg aggtccgcca gatctacgga     120
gccaagggct tcagcctgag cgacgtgccc caggcggaga tctcgggtga gcacctgcgg     180
atctgtcccc agggctacac ctgctgcacc agcgagatgg aggagaacct ggccaaccgc     240
agccatgccg agctggagac cgcgctccgg gacagcagcc gcgtcctgca ggccatgctt     300
gccacccagc tgcgcagctt cgatgaccac ttccagcacc tgctgaacga ctcggagcgg     360
acgctgcagg ccaccttccc cggcgccttc ggagagctgt acacgcagaa cgcgagggcc     420
```

```
ttccgggacc tgtactcaga gctgcgcctg tactaccgcg gtgccaacct gcacctggag    480
gagacgctgg ccgagttctg ggcccgcctg ctcgagcgcc tcttcaagca gctgcacccc    540
cagctgctgc tgcctgatga ctacctggac tgcctgggca agcaggccga ggcgctgcgg    600
cccttcgggg aggccccgag agagctgcgc ctgcgggcca cccgtgcctt cgtggctgct    660
cgctcctttg tgcagggcct gggcgtggcc agcgacgtgg tccggaaagt ggctcaggtc    720
cccctgggcc cggagtgctc gagagctgtc atgaagctgg tctactgtgc tcactgcctg    780
ggagtccccg cgccaggcc ctgccctgac tattgccgaa atgtgctcaa gggctgcctt    840
gccaaccagg ccgacctgga cgccgagtgg aggaacctcc tggactccat ggtgctcatc    900
accgacaagt tctggggtac atcgggtgtg agagtgtca tcggcagcgt gcacacgtgg    960
ctggcggagg ccatcaacgc cctccaggac aacagggaca cgctcacggc caaggtcatc    1020
cagggctgcg ggaaccccaa ggtcaacccc cagggccccg ggcctgagga agcggcgc    1080
cggggcaagc tggccccgcg ggagaggcca ccttcaggca cgctggagaa gctggtctcc    1140
gaagccaagg cccagctccg cgacgtccag gacttctgga tcagcctccc agggacactg    1200
tgcagtgaga gatggccct gagcactgcc agtgatgacc gctgctggaa cgggatggcc    1260
agaggccggt acctccccga ggtcatgggt gacggcctgg ccaaccagat caacaacccc    1320
gaggtggagt ggacatcac caagccggac atgaccatcc ggcagcagat catgcagctg    1380
aagatcatga ccaaccggct gcgcagcgcc tacaacggca cgacgtgga cttccaggac    1440
gccagtgacg acggcagcgg ctcgggcagc ggtgatggct gtctggatga cctctgcagc    1500
cggaaggtca gcaggaagag ctccagctcc cggacgccct tgacccatgc cctcccaggc    1560
ctgtcagagc aggaaggaca gaagacctcg gctgccagct gccccagcc ccgaccttc    1620
ctcctgcccc tcctcctctt cctggccctt acagtagcca ggccccggtg gcggtaa    1677
```

<210> SEQ ID NO 2
<211> LENGTH: 558
<212> TYPE: PRT
<213> ORGANISM: Homo sapiens

<400> SEQUENCE: 2

```
Met Glu Leu Arg Ala Arg Gly Trp Trp Leu Leu Cys Ala Ala Ala
1               5                  10                  15

Leu Val Ala Cys Ala Arg Gly Asp Pro Ala Ser Lys Ser Arg Ser Cys
                20                  25                  30

Gly Glu Val Arg Gln Ile Tyr Gly Ala Lys Gly Phe Ser Leu Ser Asp
            35                  40                  45

Val Pro Gln Ala Glu Ile Ser Gly Glu His Leu Arg Ile Cys Pro Gln
        50                  55                  60

Gly Tyr Thr Cys Cys Thr Ser Glu Met Glu Glu Asn Leu Ala Asn Arg
65                  70                  75                  80

Ser His Ala Glu Leu Glu Thr Ala Leu Arg Asp Ser Ser Arg Val Leu
                85                  90                  95

Gln Ala Met Leu Ala Thr Gln Leu Arg Ser Phe Asp Asp His Phe Gln
            100                 105                 110

His Leu Leu Asn Asp Ser Glu Arg Thr Leu Gln Ala Thr Phe Pro Gly
        115                 120                 125

Ala Phe Gly Glu Leu Tyr Thr Gln Asn Ala Arg Ala Phe Arg Asp Leu
    130                 135                 140

Tyr Ser Glu Leu Arg Leu Tyr Tyr Arg Gly Ala Asn Leu His Leu Glu
```

```
            145                 150                 155                 160
        Glu Thr Leu Ala Glu Phe Trp Ala Arg Leu Leu Glu Arg Leu Phe Lys
                        165                 170                 175

Gln Leu His Pro Gln Leu Leu Pro Asp Asp Tyr Leu Asp Cys Leu
                        180                 185                 190

Gly Lys Gln Ala Glu Ala Leu Arg Pro Phe Gly Glu Ala Pro Arg Glu
                        195                 200                 205

Leu Arg Leu Arg Ala Thr Arg Ala Phe Val Ala Ala Arg Ser Phe Val
                        210                 215                 220

Gln Gly Leu Gly Val Ala Ser Asp Val Val Arg Lys Val Ala Gln Val
        225                 230                 235                 240

Pro Leu Gly Pro Glu Cys Ser Arg Ala Val Met Lys Leu Val Tyr Cys
                        245                 250                 255

Ala His Cys Leu Gly Val Pro Gly Ala Arg Pro Cys Pro Asp Tyr Cys
                        260                 265                 270

Arg Asn Val Leu Lys Gly Cys Leu Ala Asn Gln Ala Asp Leu Asp Ala
                        275                 280                 285

Glu Trp Arg Asn Leu Leu Asp Ser Met Val Leu Ile Thr Asp Lys Phe
                        290                 295                 300

Trp Gly Thr Ser Gly Val Glu Ser Val Ile Gly Ser Val His Thr Trp
        305                 310                 315                 320

Leu Ala Glu Ala Ile Asn Ala Leu Gln Asp Asn Arg Asp Thr Leu Thr
                        325                 330                 335

Ala Lys Val Ile Gln Gly Cys Gly Asn Pro Lys Val Asn Pro Gln Gly
                        340                 345                 350

Pro Gly Pro Glu Glu Lys Arg Arg Gly Lys Leu Ala Pro Arg Glu
                        355                 360                 365

Arg Pro Pro Ser Gly Thr Leu Glu Lys Leu Val Ser Glu Ala Lys Ala
                        370                 375                 380

Gln Leu Arg Asp Val Gln Asp Phe Trp Ile Ser Leu Pro Gly Thr Leu
        385                 390                 395                 400

Cys Ser Glu Lys Met Ala Leu Ser Thr Ala Ser Asp Asp Arg Cys Trp
                        405                 410                 415

Asn Gly Met Ala Arg Gly Arg Tyr Leu Pro Glu Val Met Gly Asp Gly
                        420                 425                 430

Leu Ala Asn Gln Ile Asn Asn Pro Glu Val Glu Val Asp Ile Thr Lys
                        435                 440                 445

Pro Asp Met Thr Ile Arg Gln Gln Ile Met Gln Leu Lys Ile Met Thr
                        450                 455                 460

Asn Arg Leu Arg Ser Ala Tyr Asn Gly Asn Asp Val Asp Phe Gln Asp
        465                 470                 475                 480

Ala Ser Asp Asp Gly Ser Gly Ser Gly Asp Gly Cys Leu Asp
                        485                 490                 495

Asp Leu Cys Ser Arg Lys Val Ser Arg Lys Ser Ser Ser Arg Thr
                        500                 505                 510

Pro Leu Thr His Ala Leu Pro Gly Leu Ser Glu Gln Glu Gly Gln Lys
                        515                 520                 525

Thr Ser Ala Ala Ser Cys Pro Gln Pro Thr Phe Leu Leu Pro Leu
                        530                 535                 540

Leu Leu Phe Leu Ala Leu Thr Val Ala Arg Pro Arg Trp Arg
        545                 550                 555

<210> SEQ ID NO 3
```

```
<211> LENGTH: 23
<212> TYPE: PRT
<213> ORGANISM: Homo sapiens

<400> SEQUENCE: 3

Met Glu Leu Arg Ala Arg Gly Trp Trp Leu Leu Cys Ala Ala Ala
1               5                   10                  15

Leu Val Ala Cys Ala Arg Gly
            20

<210> SEQ ID NO 4
<211> LENGTH: 28
<212> TYPE: PRT
<213> ORGANISM: Homo sapiens

<400> SEQUENCE: 4

Ala Ala Ser Cys Pro Gln Pro Pro Thr Phe Leu Leu Pro Leu Leu
1               5                   10                  15

Phe Leu Ala Leu Thr Val Ala Arg Pro Arg Trp Arg
            20                  25

<210> SEQ ID NO 5
<211> LENGTH: 507
<212> TYPE: PRT
<213> ORGANISM: Homo sapiens

<400> SEQUENCE: 5

Asp Pro Ala Ser Lys Ser Arg Ser Cys Gly Glu Val Arg Gln Ile Tyr
1               5                   10                  15

Gly Ala Lys Gly Phe Ser Leu Ser Asp Val Pro Gln Ala Glu Ile Ser
            20                  25                  30

Gly Glu His Leu Arg Ile Cys Pro Gln Gly Tyr Thr Cys Cys Thr Ser
        35                  40                  45

Glu Met Glu Glu Asn Leu Ala Asn Arg Ser His Ala Glu Leu Glu Thr
    50                  55                  60

Ala Leu Arg Asp Ser Ser Arg Val Leu Gln Ala Met Leu Ala Thr Gln
65                  70                  75                  80

Leu Arg Ser Phe Asp Asp His Phe Gln His Leu Leu Asn Asp Ser Glu
                85                  90                  95

Arg Thr Leu Gln Ala Thr Phe Pro Gly Ala Phe Gly Glu Leu Tyr Thr
            100                 105                 110

Gln Asn Ala Arg Ala Phe Arg Asp Leu Tyr Ser Glu Leu Arg Leu Tyr
        115                 120                 125

Tyr Arg Gly Ala Asn Leu His Leu Glu Glu Thr Leu Ala Glu Phe Trp
    130                 135                 140

Ala Arg Leu Leu Glu Arg Leu Phe Lys Gln Leu His Pro Gln Leu Leu
145                 150                 155                 160

Leu Pro Asp Asp Tyr Leu Asp Cys Leu Gly Lys Gln Ala Glu Ala Leu
                165                 170                 175

Arg Pro Phe Gly Glu Ala Pro Arg Glu Leu Arg Leu Arg Ala Thr Arg
            180                 185                 190

Ala Phe Val Ala Ala Arg Ser Phe Val Gln Gly Leu Gly Val Ala Ser
        195                 200                 205

Asp Val Val Arg Lys Val Ala Gln Val Pro Leu Gly Pro Glu Cys Ser
    210                 215                 220

Arg Ala Val Met Lys Leu Val Tyr Cys Ala His Cys Leu Gly Val Pro
225                 230                 235                 240
```

-continued

```
Gly Ala Arg Pro Cys Pro Asp Tyr Cys Arg Asn Val Leu Lys Gly Cys
            245                 250                 255

Leu Ala Asn Gln Ala Asp Leu Asp Ala Glu Trp Arg Asn Leu Leu Asp
        260                 265                 270

Ser Met Val Leu Ile Thr Asp Lys Phe Trp Gly Thr Ser Gly Val Glu
    275                 280                 285

Ser Val Ile Gly Ser Val His Thr Trp Leu Ala Glu Ala Ile Asn Ala
290                 295                 300

Leu Gln Asp Asn Arg Asp Thr Leu Thr Ala Lys Val Ile Gln Gly Cys
305                 310                 315                 320

Gly Asn Pro Lys Val Asn Pro Gln Gly Pro Gly Pro Glu Glu Lys Arg
            325                 330                 335

Arg Arg Gly Lys Leu Ala Pro Arg Glu Arg Pro Pro Ser Gly Thr Leu
        340                 345                 350

Glu Lys Leu Val Ser Glu Ala Lys Ala Gln Leu Arg Asp Val Gln Asp
    355                 360                 365

Phe Trp Ile Ser Leu Pro Gly Thr Leu Cys Ser Glu Lys Met Ala Leu
370                 375                 380

Ser Thr Ala Ser Asp Asp Arg Cys Trp Asn Gly Met Ala Arg Gly Arg
385                 390                 395                 400

Tyr Leu Pro Glu Val Met Gly Asp Gly Leu Ala Asn Gln Ile Asn Asn
            405                 410                 415

Pro Glu Val Glu Val Asp Ile Thr Lys Pro Asp Met Thr Ile Arg Gln
        420                 425                 430

Gln Ile Met Gln Leu Lys Ile Met Thr Asn Arg Leu Arg Ser Ala Tyr
    435                 440                 445

Asn Gly Asn Asp Val Asp Phe Gln Asp Ala Ser Asp Asp Gly Ser Gly
450                 455                 460

Ser Gly Ser Gly Asp Gly Cys Leu Asp Asp Leu Cys Ser Arg Lys Val
465                 470                 475                 480

Ser Arg Lys Ser Ser Ser Arg Thr Pro Leu Thr His Ala Leu Pro
            485                 490                 495

Gly Leu Ser Glu Gln Glu Gly Gln Lys Thr Ser
        500                 505

<210> SEQ ID NO 6
<211> LENGTH: 10
<212> TYPE: PRT
<213> ORGANISM: Homo sapiens

<400> SEQUENCE: 6

Lys Val Asn Pro Gln Gly Pro Gly Pro Glu
1               5                   10

<210> SEQ ID NO 7
<211> LENGTH: 9
<212> TYPE: PRT
<213> ORGANISM: Homo sapiens

<400> SEQUENCE: 7

Lys Val Asn Pro Gln Gly Pro Gly Pro
1               5

<210> SEQ ID NO 8
<211> LENGTH: 6
<212> TYPE: PRT
<213> ORGANISM: Homo sapiens
```

-continued

<400> SEQUENCE: 8

Thr Gln Asn Ala Arg Ala
1               5

<210> SEQ ID NO 9
<211> LENGTH: 9
<212> TYPE: PRT
<213> ORGANISM: Homo sapiens

<400> SEQUENCE: 9

Thr Gln Asn Ala Arg Ala Phe Arg Asp
1               5

<210> SEQ ID NO 10
<211> LENGTH: 461
<212> TYPE: PRT
<213> ORGANISM: Mus musculus

<400> SEQUENCE: 10

Met Ala Trp Val Trp Thr Leu Leu Phe Leu Met Ala Ala Ala Gln Ser
1               5                   10                  15

Ile Gln Ala Gln Ile Gln Leu Val Gln Ser Gly Pro Glu Leu Lys Lys
            20                  25                  30

Pro Gly Glu Thr Val Lys Ile Ser Cys Lys Ala Ser Gly Tyr Ala Phe
        35                  40                  45

Thr Asp Tyr Ser Met Asn Trp Val Lys Gln Ala Pro Gly Lys Gly Leu
    50                  55                  60

Arg Trp Met Gly Trp Ile Asn Thr Glu Thr Gly Glu Pro Thr Tyr Thr
65                  70                  75                  80

Asp Asp Phe Lys Gly Arg Phe Ala Phe Ser Leu Glu Thr Ser Ala Ser
                85                  90                  95

Thr Ala Phe Leu Gln Ile Asn Asn Leu Arg Asn Glu Asp Thr Ala Thr
            100                 105                 110

Tyr Phe Cys Ala Arg His Tyr Asp Tyr Gly Gly Phe Pro Tyr Trp Gly
        115                 120                 125

Gln Gly Thr Leu Val Thr Val Ser Ala Ala Lys Thr Thr Pro Pro Ser
    130                 135                 140

Val Tyr Pro Leu Ala Pro Gly Ser Ala Ala Gln Thr Asn Ser Met Val
145                 150                 155                 160

Thr Leu Gly Cys Leu Val Lys Gly Tyr Phe Pro Glu Pro Val Thr Val
                165                 170                 175

Thr Trp Asn Ser Gly Ser Leu Ser Ser Gly Val His Thr Phe Pro Ala
            180                 185                 190

Val Leu Gln Ser Asp Leu Tyr Thr Leu Ser Ser Ser Val Thr Val Pro
        195                 200                 205

Ser Ser Thr Trp Pro Ser Glu Thr Val Thr Cys Asn Val Ala His Pro
    210                 215                 220

Ala Ser Ser Thr Lys Val Asp Lys Lys Ile Val Pro Arg Asp Cys Gly
225                 230                 235                 240

Cys Lys Pro Cys Ile Cys Thr Val Pro Glu Val Ser Ser Val Phe Ile
                245                 250                 255

Phe Pro Pro Lys Pro Lys Asp Val Leu Thr Ile Thr Leu Thr Pro Lys
            260                 265                 270

Val Thr Cys Val Val Val Asp Ile Ser Lys Asp Asp Pro Glu Val Gln
        275                 280                 285

Phe Ser Trp Phe Val Asp Asp Val Glu Val His Thr Ala Gln Thr Gln

```
            290                 295                 300
Pro Arg Glu Glu Gln Phe Asn Ser Thr Phe Arg Ser Val Ser Glu Leu
305                 310                 315                 320

Pro Ile Met His Gln Asp Trp Leu Asn Gly Lys Glu Phe Lys Cys Arg
                325                 330                 335

Val Asn Ser Ala Ala Phe Pro Ala Pro Ile Glu Lys Thr Ile Ser Lys
            340                 345                 350

Thr Lys Gly Arg Pro Lys Ala Pro Gln Val Tyr Thr Ile Pro Pro Pro
        355                 360                 365

Lys Glu Gln Met Ala Lys Asp Lys Val Ser Leu Thr Cys Met Ile Thr
370                 375                 380

Asp Phe Phe Pro Glu Asp Ile Thr Val Glu Trp Gln Trp Asn Gly Gln
385                 390                 395                 400

Pro Ala Glu Asn Tyr Lys Asn Thr Gln Pro Ile Met Asp Thr Asp Gly
                405                 410                 415

Ser Tyr Phe Val Tyr Ser Lys Leu Asn Val Gln Lys Ser Asn Trp Glu
            420                 425                 430

Ala Gly Asn Thr Phe Thr Cys Ser Val Leu His Glu Gly Leu His Asn
        435                 440                 445

His His Thr Glu Lys Ser Leu Ser His Ser Pro Gly Lys
450                 455                 460

<210> SEQ ID NO 11
<211> LENGTH: 234
<212> TYPE: PRT
<213> ORGANISM: Mus musculus

<400> SEQUENCE: 11

Met Ser Val Leu Thr Gln Val Leu Ala Leu Leu Leu Leu Trp Leu Thr
1               5                   10                  15

Gly Ala Arg Cys Asp Ile Gln Met Thr Gln Ser Pro Ala Ser Leu Ser
            20                  25                  30

Ala Ser Val Gly Glu Thr Val Thr Ile Thr Cys Arg Ala Ser Gly Asn
        35                  40                  45

Val His Asn Tyr Leu Ala Trp Tyr Gln Gln Lys Gln Gly Lys Ser Pro
    50                  55                  60

Gln Leu Leu Val Tyr Thr Ala Lys Thr Leu Ala Asp Gly Val Pro Ser
65                  70                  75                  80

Arg Phe Ser Gly Ser Gly Ser Gly Thr Gln Tyr Ser Leu Lys Ile Asn
                85                  90                  95

Ser Leu Gln Pro Glu Asp Phe Gly Thr Tyr Tyr Cys Gln His Phe Trp
            100                 105                 110

Ser Asn Pro Trp Thr Phe Gly Gly Gly Thr Lys Leu Glu Ile Lys Arg
        115                 120                 125

Ala Asp Ala Ala Pro Thr Val Ser Ile Phe Pro Pro Ser Ser Glu Gln
    130                 135                 140

Leu Thr Ser Gly Gly Ala Ser Val Val Cys Phe Leu Asn Asn Phe Tyr
145                 150                 155                 160

Pro Lys Asp Ile Asn Val Lys Trp Lys Ile Asp Gly Ser Glu Arg Gln
                165                 170                 175

Asn Gly Val Leu Asn Ser Trp Thr Asp Gln Asp Ser Lys Asp Ser Thr
            180                 185                 190

Tyr Ser Met Ser Ser Thr Leu Thr Leu Thr Lys Asp Glu Tyr Glu Arg
        195                 200                 205
```

His Asn Ser Tyr Thr Cys Glu Ala Thr His Lys Thr Ser Thr Ser Pro
    210                 215                 220

Ile Val Lys Ser Phe Asn Arg Asn Glu Cys
225                 230

<210> SEQ ID NO 12
<211> LENGTH: 238
<212> TYPE: PRT
<213> ORGANISM: Mus musculus

<400> SEQUENCE: 12

Met Gly Ile Lys Met Glu Ser Gln Thr Gln Val Phe Val Tyr Met Leu
1               5                   10                  15

Leu Trp Leu Ser Gly Val Asp Gly Asp Ile Val Met Thr Gln Ser Gln
            20                  25                  30

Lys Phe Met Ser Thr Ser Ile Gly Asp Arg Val Ser Val Thr Cys Lys
        35                  40                  45

Ala Ser Gln Asn Val Gly Ser His Val Ala Trp Phe Gln Gln Lys Pro
    50                  55                  60

Gly Gln Ser Pro Lys Ala Leu Ile Tyr Ser Ala Ser Tyr Arg Tyr Ser
65                  70                  75                  80

Gly Val Thr Asp Arg Phe Thr Gly Ser Gly Ser Gly Thr Asp Phe Thr
                85                  90                  95

Leu Thr Ile Asn Asn Val Gln Ser Glu Asp Leu Ala Glu Tyr Phe Cys
            100                 105                 110

Gln Gln Tyr Asn Ser Phe Pro Phe Thr Phe Gly Ser Gly Thr Lys Leu
        115                 120                 125

Glu Ile Lys Arg Ala Asp Ala Ala Pro Thr Val Ser Ile Phe Pro Pro
130                 135                 140

Ser Ser Glu Gln Leu Thr Ser Gly Gly Ala Ser Val Val Cys Phe Leu
145                 150                 155                 160

Asn Asn Phe Tyr Pro Lys Asp Ile Asn Val Lys Trp Lys Ile Asp Gly
                165                 170                 175

Ser Glu Arg Gln Asn Gly Val Leu Asn Ser Trp Thr Asp Gln Asp Ser
            180                 185                 190

Lys Asp Ser Thr Tyr Ser Met Ser Ser Thr Leu Thr Leu Thr Lys Asp
        195                 200                 205

Glu Tyr Glu Arg His Asn Ser Tyr Thr Cys Glu Ala Thr His Lys Thr
    210                 215                 220

Ser Thr Ser Pro Ile Val Lys Ser Phe Asn Arg Asn Glu Cys
225                 230                 235

<210> SEQ ID NO 13
<211> LENGTH: 1386
<212> TYPE: DNA
<213> ORGANISM: Mus musculus

<400> SEQUENCE: 13
atggcttggg tgtggacctt gctattcctg atggctgctg cccaaagtat ccaagcacag    60
atccagttgg tgcagtctgg acctgagctg aagaagcctg gagagacagt caagatctcc   120
tgcaaggctt ctggttatgc cttcacagac tattcaatga actgggtgaa gcaggctcca   180
ggaaagggtt taaggtggat gggctggata aacactgaga ctggtgagcc aacatataca   240
gatgacttca aggacggtt tgccttctct ttggaaacct ctgccagcac tgcctttttg   300
cagatcaaca acctcagaaa tgaagacacg gctacatatt tctgtgctag acactatgat   360

```
tacgggggt ttccttactg gggccaaggg actctggtca ctgtctctgc agccaaaacg    420
acacccccat ctgtctatcc actggcccct ggatctgctg cccaaactaa ctccatggtg    480
accctgggat gcctggtcaa gggctatttc cctgagccag tgacagtgac ctggaactct    540
ggatccctgt ccagcggtgt gcacaccttc ccagctgtcc tgcagtctga cctctacact    600
ctgagcagct cagtgactgt cccctccagc acctggccca gcgagaccgt cacctgcaac    660
gttgcccacc cggccagcag caccaaggtg gacaagaaaa ttgtgcccag ggattgtggt    720
tgtaagcctt gcatatgtac agtcccagaa gtatcatctg tcttcatctt ccccccaaag    780
cccaaggatg tgctcaccat tactctgact cctaaggtca cgtgtgttgt ggtagacatc    840
agcaaggatg atcccgaggt ccagttcagc tggtttgtag atgatgtgga ggtgcacaca    900
gctcagacgc aacccgggga ggagcagttc aacagcactt tccgctcagt cagtgaactt    960
cccatcatgc accaggactg gctcaatggc aaggagttca atgcagggt caacagtgca   1020 gctttccctg cccccatcga gaaaaccatc tccaaaacca aggcagacc gaaggctcca   1080 caggtgtaca ccattccacc tcccaaggag cagatggcca aggataaagt cagtctgacc   1140
tgcatgataa cagacttctt ccctgaagac attactgtgg agtggcagtg aatgggcag   1200 ccagcggaga actacaagaa cactcagccc atcatggaca cagatggctc ttacttcgtc   1260
tacagcaagc tcaatgtgca gaagagcaac tgggaggcag gaaatacttt cacctgctct   1320
gtgttacatg agggcctgca caaccaccat actgagaaga gcctctccca ctctcctggt   1380
aaatga                                                              1386

<210> SEQ ID NO 14
<211> LENGTH: 705
<212> TYPE: DNA
<213> ORGANISM: Mus musculus

<400> SEQUENCE: 14
atgagtgtgc tcactcaggt cctggcgttg ctgctgctgt ggcttacagg tgccagatgt     60
gacatccaga tgactcagtc tccagcctcc ctatctgcat ctgtgggaga aactgtcacc    120
atcacatgtc gagcaagtgg gaatgttcac aattatttag catggtatca gcagaaacag    180
ggaaaatctc ctcaactcct ggtctatact gcaaaaacct agcagatgg tgtgccatca    240 aggttcagtg gcagtggatc aggaacacaa tattctctca agatcaatag cctgcagcct    300
gaagattttg ggacttatta ctgtcaacat ttttggagta atccgtggac gttcggtgga    360
ggcaccaagc tggaaatcaa acgggctgat gctgcaccaa ctgtatccat cttcccacca    420
tccagtgagc agttaacatc tggaggtgcc tcagtcgtgt gcttcttgaa caacttctac    480
cccaaagaca tcaatgtcaa gtggaagatt gatggcagtg aacgacaaaa tggcgtcctg    540
aacagttgga ctgatcagga cagcaaagac agcacctaca gcatgagcag caccctcacg    600
ttgaccaagg acgagtatga acgacataac agctatacct gtgaggccac tcacaagaca    660
tcaacttcac ccattgtcaa gagcttcaac aggaatgagt gttag                    705

<210> SEQ ID NO 15
<211> LENGTH: 717
<212> TYPE: DNA
<213> ORGANISM: Mus musculus

<400> SEQUENCE: 15
atgggcatca gatggagtc acagactcag gtctttgtat acatgttgct gtggttgtct     60
ggtgttgatg gagacattgt gatgacccag tctcaaaagt tcatgtccac atcaatagga    120
```

```
gacagggtca gcgtcacctg caaggccagt cagaatgtgg gttctcatgt agcctggttt      180
cagcagaaac cagggcaatc tcctaaagca ctgatttact cggcatccta ccggtacagc      240
ggagtcactg atcgcttcac aggcagtgga tctgggacag atttcactct caccatcaac      300
aatgtgcagt ctgaagactt ggcagagtat ttctgtcagc aatataacag ttttccattc      360
acgttcggtt cggggacaaa gttggaaata aaacgggctg atgctgcacc aactgtatcc      420
atcttcccac catccagtga gcagttaaca tctggaggtg cctcagtcgt gtgcttcttg      480
aacaacttct accccaaaga catcaatgtc aagtggaaga ttgatggcag tgaacgacaa      540
aatggcgtcc tgaacagttg gactgatcag gacagcaaag acagcaccta gcatgagc      600 agcaccctca cgttgaccaa ggacgagtat gaacgacata cagctatac ctgtgaggcc      660 actcacaaga catcaacttc acccattgtc aagagcttca acaggaatga gtgttag      717
```

<210> SEQ ID NO 16
<211> LENGTH: 558
<212> TYPE: PRT
<213> ORGANISM: Homo sapiens

<400> SEQUENCE: 16

```
Met Glu Leu Arg Ala Arg Gly Trp Trp Leu Leu Cys Ala Ala Ala Ala
1               5                   10                  15

Leu Val Ala Cys Ala Arg Gly Asp Pro Ala Ser Lys Ser Arg Ser Cys
            20                  25                  30

Gly Glu Val Arg Gln Ile Tyr Gly Ala Lys Gly Phe Ser Leu Ser Asp
        35                  40                  45

Val Pro Gln Ala Glu Ile Ser Gly Glu His Leu Arg Ile Cys Pro Gln
    50                  55                  60

Gly Tyr Thr Cys Cys Thr Ser Glu Met Glu Glu Asn Leu Ala Asn Arg
65                  70                  75                  80

Ser His Ala Glu Leu Glu Thr Ala Leu Arg Asp Ser Ser Arg Val Leu
                85                  90                  95

Gln Ala Met Leu Ala Thr Gln Leu Arg Ser Phe Asp Asp His Phe Gln
            100                 105                 110

His Leu Leu Asn Asp Ser Glu Arg Thr Leu Gln Ala Thr Phe Pro Gly
        115                 120                 125

Ala Phe Gly Glu Leu Tyr Thr Gln Asn Ala Arg Ala Phe Arg Asp Leu
    130                 135                 140

Tyr Ser Glu Leu Arg Leu Tyr Tyr Arg Gly Ala Asn Leu His Leu Glu
145                 150                 155                 160

Glu Thr Leu Ala Glu Phe Trp Ala Arg Leu Leu Glu Arg Leu Phe Lys
                165                 170                 175

Gln Leu His Pro Gln Leu Leu Leu Pro Asp Asp Tyr Leu Asp Cys Leu
            180                 185                 190

Gly Lys Gln Ala Glu Ala Leu Arg Pro Phe Gly Glu Ala Pro Arg Glu
        195                 200                 205

Leu Arg Leu Arg Ala Thr Arg Ala Phe Val Ala Ala Arg Ser Phe Val
    210                 215                 220

Gln Gly Leu Gly Val Ala Ser Asp Val Val Arg Lys Val Ala Gln Val
225                 230                 235                 240

Pro Leu Gly Pro Glu Cys Ser Arg Ala Val Met Lys Leu Val Tyr Cys
                245                 250                 255

Ala His Cys Leu Gly Val Pro Gly Ala Arg Pro Cys Pro Asp Tyr Cys
            260                 265                 270
```

```
Arg Asn Val Leu Lys Gly Cys Leu Ala Asn Gln Ala Asp Leu Asp Ala
        275                 280                 285

Glu Trp Arg Asn Leu Leu Asp Ser Met Val Leu Ile Thr Asp Lys Phe
    290                 295                 300

Trp Gly Thr Ser Gly Val Glu Ser Val Ile Gly Ser Val His Thr Trp
305                 310                 315                 320

Leu Ala Glu Ala Ile Asn Ala Leu Gln Asp Asn Arg Asp Thr Leu Thr
                325                 330                 335

Ala Lys Val Ile Gln Gly Cys Gly Asn Pro Lys Val Asn Pro Gln Gly
            340                 345                 350

Pro Gly Pro Glu Glu Lys Arg Arg Gly Lys Leu Ala Pro Arg Glu
        355                 360                 365

Arg Pro Pro Ser Gly Thr Leu Glu Lys Leu Val Ser Glu Ala Lys Ala
    370                 375                 380

Gln Leu Arg Asp Val Gln Asp Phe Trp Ile Ser Leu Pro Gly Thr Leu
385                 390                 395                 400

Cys Ser Glu Lys Met Ala Leu Ser Thr Ala Ser Asp Arg Cys Trp
                405                 410                 415

Asn Gly Met Ala Arg Gly Arg Tyr Leu Pro Glu Val Met Gly Asp Gly
            420                 425                 430

Leu Ala Asn Gln Ile Asn Asn Pro Glu Val Glu Val Asp Ile Thr Lys
                435                 440                 445

Pro Asp Met Thr Ile Arg Gln Gln Ile Met Gln Leu Lys Ile Met Thr
    450                 455                 460

Asn Arg Leu Arg Ser Ala Tyr Asn Gly Asn Asp Val Asp Phe Gln Asp
465                 470                 475                 480

Ala Ser Asp Asp Gly Ser Gly Ser Gly Ser Gly Asp Gly Cys Leu Asp
                485                 490                 495

Asp Leu Cys Ser Arg Lys Val Ser Arg Lys Ser Ser Ser Arg Thr
            500                 505                 510

Pro Leu Thr His Ala Leu Pro Gly Leu Ser Glu Gln Glu Gly Gln Lys
    515                 520                 525

Thr Ser Ala Ala Ser Cys Pro Gln Pro Thr Phe Leu Leu Pro Leu
        530                 535                 540

Leu Leu Phe Leu Ala Leu Thr Val Ala Arg Pro Arg Trp Arg
545                 550                 555

<210> SEQ ID NO 17
<211> LENGTH: 23
<212> TYPE: PRT
<213> ORGANISM: Homo sapiens

<400> SEQUENCE: 17

Gly Asn Pro Lys Val Asn Pro Gln Gly Pro Gly Pro Glu Glu Lys Arg
1               5                   10                  15

Arg Arg Gly Lys Leu Ala Pro
            20

<210> SEQ ID NO 18
<211> LENGTH: 19
<212> TYPE: PRT
<213> ORGANISM: Homo sapiens

<400> SEQUENCE: 18

Gly Glu Leu Tyr Thr Gln Asn Ala Arg Ala Phe Arg Asp Leu Tyr Ser
1               5                   10                  15
```

Glu Leu Arg

<210> SEQ ID NO 19
<211> LENGTH: 17
<212> TYPE: PRT
<213> ORGANISM: Artificial Sequence
<220> FEATURE:
<223> OTHER INFORMATION: Description of Artificial Sequence: Labeled
      homo sapiens Glypican-1 sequence

<400> SEQUENCE: 19

Arg Asn Pro Lys Val Asn Pro Gln Gly Pro Gly Pro Glu Glu Lys Arg
1               5                   10                  15

Arg

<210> SEQ ID NO 20
<211> LENGTH: 15
<212> TYPE: PRT
<213> ORGANISM: Homo sapiens

<400> SEQUENCE: 20

Pro Lys Val Asn Pro Gln Gly Pro Gly Pro Glu Glu Lys Arg Arg
1               5                   10                  15

<210> SEQ ID NO 21
<211> LENGTH: 17
<212> TYPE: PRT
<213> ORGANISM: Artificial Sequence
<220> FEATURE:
<223> OTHER INFORMATION: Description of Artificial Sequence: Labeled
      homo sapiens Glypican-1 sequence

<400> SEQUENCE: 21

Arg Asn Glu Leu Cys Thr Gln Asn Cys Arg Ala Phe Arg Asp Leu Tyr
1               5                   10                  15

Ser

<210> SEQ ID NO 22
<211> LENGTH: 11
<212> TYPE: PRT
<213> ORGANISM: Homo sapiens

<400> SEQUENCE: 22

Val Asn Pro Gln Gly Pro Gly Pro Glu Glu Lys
1               5                   10

<210> SEQ ID NO 23
<211> LENGTH: 558
<212> TYPE: PRT
<213> ORGANISM: Homo sapiens

<400> SEQUENCE: 23

Met Glu Leu Arg Ala Arg Gly Trp Trp Leu Leu Cys Ala Ala Ala Ala
1               5                   10                  15

Leu Val Ala Cys Ala Arg Gly Asp Pro Ala Ser Lys Ser Arg Ser Cys
                20                  25                  30

Gly Glu Val Arg Gln Ile Tyr Gly Ala Lys Gly Phe Ser Leu Ser Asp
            35                  40                  45

Val Pro Gln Ala Glu Ile Ser Gly Glu His Leu Arg Ile Cys Pro Gln
        50                  55                  60

Gly Tyr Thr Cys Cys Thr Ser Glu Met Glu Glu Asn Leu Ala Asn Arg
65                  70                  75                  80

-continued

```
Ser His Ala Glu Leu Glu Thr Ala Leu Arg Asp Ser Arg Val Leu
                 85                  90                  95

Gln Ala Met Leu Ala Thr Gln Leu Arg Ser Phe Asp Asp His Phe Gln
            100                 105                 110

His Leu Leu Asn Asp Ser Glu Arg Thr Leu Gln Ala Thr Phe Pro Gly
        115                 120                 125

Ala Phe Gly Glu Leu Tyr Thr Gln Asn Ala Arg Ala Phe Arg Asp Leu
    130                 135                 140

Tyr Ser Glu Leu Arg Leu Tyr Arg Gly Ala Asn Leu His Leu Glu
145                 150                 155                 160

Glu Thr Leu Ala Glu Phe Trp Ala Arg Leu Leu Glu Arg Leu Phe Lys
                165                 170                 175

Gln Leu His Pro Gln Leu Leu Leu Pro Asp Asp Tyr Leu Asp Cys Leu
            180                 185                 190

Gly Lys Gln Ala Glu Ala Leu Arg Pro Phe Gly Glu Ala Pro Arg Glu
        195                 200                 205

Leu Arg Leu Arg Ala Thr Arg Ala Phe Val Ala Ala Arg Ser Phe Val
    210                 215                 220

Gln Gly Leu Gly Val Ala Ser Asp Val Val Arg Lys Val Ala Gln Val
225                 230                 235                 240

Pro Leu Gly Pro Glu Cys Ser Arg Ala Val Met Lys Leu Val Tyr Cys
                245                 250                 255

Ala His Cys Leu Gly Val Pro Gly Ala Arg Pro Cys Pro Asp Tyr Cys
            260                 265                 270

Arg Asn Val Leu Lys Gly Cys Leu Ala Asn Gln Ala Asp Leu Asp Ala
        275                 280                 285

Glu Trp Arg Asn Leu Leu Asp Ser Met Val Leu Ile Thr Asp Lys Phe
    290                 295                 300

Trp Gly Thr Ser Gly Val Glu Ser Val Ile Gly Ser Val His Thr Trp
305                 310                 315                 320

Leu Ala Glu Ala Ile Asn Ala Leu Gln Asp Asn Arg Asp Thr Leu Thr
                325                 330                 335

Ala Lys Val Ile Gln Gly Cys Gly Asn Pro Lys Val Asn Pro Gln Gly
            340                 345                 350

Pro Gly Pro Glu Glu Lys Arg Arg Arg Gly Lys Leu Ala Pro Arg Glu
        355                 360                 365

Arg Pro Pro Ser Gly Thr Leu Glu Lys Leu Val Ser Glu Ala Lys Ala
    370                 375                 380

Gln Leu Arg Asp Val Gln Asp Phe Trp Ile Ser Leu Pro Gly Thr Leu
385                 390                 395                 400

Cys Ser Glu Lys Met Ala Leu Ser Thr Ala Ser Asp Asp Arg Cys Trp
                405                 410                 415

Asn Gly Met Ala Arg Gly Arg Tyr Leu Pro Glu Val Met Gly Asp Gly
            420                 425                 430

Leu Ala Asn Gln Ile Asn Asn Pro Glu Val Glu Val Asp Ile Thr Lys
        435                 440                 445

Pro Asp Met Thr Ile Arg Gln Gln Ile Met Gln Leu Lys Ile Met Thr
    450                 455                 460

Asn Arg Leu Arg Ser Ala Tyr Asn Gly Asn Asp Val Asp Phe Gln Asp
465                 470                 475                 480

Ala Ser Asp Asp Gly Ser Gly Ser Gly Asp Gly Cys Leu Asp
                485                 490                 495
```

```
Asp Leu Cys Ser Arg Lys Val Ser Arg Lys Ser Ser Ser Ser Arg Thr
            500                 505                 510

Pro Leu Thr His Ala Leu Pro Gly Leu Ser Glu Gln Glu Gly Gln Lys
        515                 520                 525

Thr Ser Ala Ala Ser Cys Pro Gln Pro Pro Thr Phe Leu Leu Pro Leu
        530                 535                 540

Leu Leu Phe Leu Ala Leu Thr Val Ala Arg Pro Arg Trp Arg
545                 550                 555

<210> SEQ ID NO 24
<211> LENGTH: 17
<212> TYPE: PRT
<213> ORGANISM: Homo sapiens

<400> SEQUENCE: 24

Cys Pro Lys Val Asn Pro Gln Gly Pro Gly Pro Glu Glu Lys Arg Arg
1               5                   10                  15

Cys
```

CELL SURFACE PROSTATE CANCER ANTIGEN FOR DIAGNOSIS

INCORPORATION BY CROSS-REFERENCE

The present application is a National Stage Application filed under 35 U.S.C. 371 of International Application No. PCT/AU2015/000018, filed Jan. 16, 2015, which claims priority from Unites States of America provisional patent application No. 61/928,776 filed on 17 Jan. 2014, the entire contents of which are incorporated herein by cross-reference.

FIELD OF THE INVENTION

The present invention relates generally to the field of prostate cancer diagnostics. In particular, the present invention relates to the identification of biomarkers in biological samples, which can be used in the detection of prostate cancer. The identified markers may also be used in determining prognosis and monitoring response to treatment for prostate cancer patients.

BACKGROUND OF THE INVENTION

Prostate cancer is the most frequently diagnosed visceral cancer and the second leading cause of cancer death for men in the United States. The American Cancer Society estimates that in 2013 about 238,590 new cases of prostate cancer will be diagnosed and 29,720 men will die of the disease. Overall, one in six men will be diagnosed with prostate cancer in their lifetime.

Currently, prostate cancer can be detected by either digital rectal exam (DRE) or by the measurement of prostate-specific antigen (PSA) in the blood of patients. However, neither test is entirely conclusive, and both can lead to false negatives (leaving real cancers undetected), and false positives (signaling cancer where there is none). For example, standard PSA tests conducted at the recommended 4.0 ng/ml cutoff, are 86% sensitive to cancer patients but only 33% specific, producing false positives in roughly 67% of non-cancer patients (Hoffman et al. 2002). False positives are usually followed by invasive and painful biopsies.

A need exists for prostate cancer diagnostic tests with improved accuracy and/or sensitivity.

SUMMARY OF THE INVENTION

The present invention is based, in part, on the discovery that glypican-1 heparan sulfate proteoglycan (GPC-1) levels are elevated in the body fluids or tissues of prostate cancer patients. The present inventors have discovered that glypican-1 is a new marker for prostate cancer. Accordingly, the present invention provides for methods of detecting glypican-1 to determine the existence of prostate cancer in patients.

In one embodiment, the invention provides for methods for detecting prostate cancer in a patient comprising obtaining a body fluid or tissue sample from a patient, contacting said sample with an anti-glypican-1 antibody, determining that said patient has prostate cancer or an increased likelihood of developing prostate cancer based upon binding of said anti-glypican-1 antibody to said body fluid or tissue sample. In some embodiments the levels of one or more additional prostate markers are measured in the body fluid or tissue sample, and the determination that the patient has cancer is based upon the levels of glypican-1 and the levels of the one or more additional markers in the patient body fluid or tissue sample. In some embodiments, the cancer is prostate cancer, and the additional marker is PSA. In some embodiments, the anti-glypican-1 antibody is MIL-38. In other embodiments, the anti-glypican-1 antibody is not MIL-38. In some embodiments, the anti-glypican-1 antibody is an antibody fragment or recombinant antibody capable of binding glypican-1. In some embodiments, the anti-glypican-1 antibody is labeled for easy detection. In some embodiments the antibody label can be a fluorescent label, a biotin-avidin amplification system, a chemiluminescence system, microspheres or colloidal gold among others.

In some embodiments the body fluid sample obtained from the patient is a blood, serum, plasma, or urine sample.

In one embodiment, the anti-glypican-1 antibody binding to the patient's body fluid or tissue sample is compared to the level of anti-glypican-1 antibody binding of a control sample; wherein increased anti-glypican-1 antibody binding of the body fluid or tissue sample over the control sample is associated with the presence of prostate cancer. In some embodiments, said control sample comprises the body fluid from an age-matched prostate cancer-free patient.

In other embodiments, the level of anti-glypican-1 antibody binding to the patient's body fluid or tissue is compared to the level of anti-glypican-1 antibody binding to a reference standard, wherein increased anti-glypican-1 antibody binding of the body fluid or tissue sample over the reference standard sample is associated with the presence of prostate cancer. In some embodiments, said reference standard comprises a sample with known glypican-1 content. In some embodiments, the comparison of the anti-glypican-1 binding to the body fluid or tissue is compared to the anti-glypican-1 binding to the glypican-1 standards to quantify the amount of glypican-1 in said body fluid.

In some embodiments, glypican-1 content higher than about: 0.1 ng/ml, 0.5 ng/ml, 1 ng/ml, 5 ng/ml, 10 ng/ml, 15 ng/ml or 20 ng/ml in the body fluid sample is indicative of prostate cancer.

The diagnostic methods of the invention may further comprise administering one or more prostate cancer treatments to a patient, and following changes in the level of glypican-1 in body fluids or tissues as a mechanism to monitor patient recovery or responses to the prostate cancer treatments. In some embodiments, the anti-glypican-1 antibody binding is detected via techniques such as immunofluorescence, radiolabeling, immunoblotting, enzyme-linked immunoassay, flow cytometry, optical density, and chemiluminescence.

The present invention also includes kits for detecting glypican-1 in the body fluids or tissues of patients. In one embodiment the kit for detecting prostate cancer comprises a first anti-glypican-1 antibody, a pharmaceutically acceptable carrier, and glypican-1 standards; wherein said kit is capable of detecting glypican-1 in the body fluid or tissue of a patient. In some embodiments the kit further comprises a secondary ligand. In some embodiments the secondary ligand is a second anti-glypican-1 antibody. In one embodiment, the second anti-glypican-1 antibody is the same as the first anti-glypican-1 antibody.

In some embodiments, the secondary ligand is conjugated to a label for rapid detection of said ligand.

The present invention thus relates at least to the following series of numbered embodiments below:

Embodiment 1

A method of detecting prostate cancer in a patient, the method comprising measuring the level of glypican-1 in a body fluid sample from a patient and determining that said patient has prostate cancer or an increased likelihood of developing prostate cancer based upon the level of glypican-1 in the body fluid sample.

Embodiment 2

The method of detecting prostate cancer in a patient of embodiment 1, comprising the steps of:
(a) obtaining a body fluid sample from a patient;
(b) contacting said body fluid sample with an anti-glypican-1 antibody; and
(c) determining that said patient has prostate cancer or an increased likelihood of developing prostate cancer based upon binding of said anti-glypican-1 antibody to said body fluid sample.

Embodiment 3

The method of embodiment 2, wherein said anti-glypican-1 antibody is MIL-38.

Embodiment 4

The method of embodiment 2, wherein said body fluid sample is contacted with a population of antibodies, wherein:
antibodies of the population comprise:
(a) a heavy chain variable region comprising:
a complementarity determining region 1 (CDR1) comprising or consisting of an amino acid sequence defined by positions 50-54 of SEQ ID NO: 10;
a complementarity determining region 2 (CDR2) comprising or consisting of an amino acid sequence defined by positions 69-85 of SEQ ID NO: 10;
a complementarity determining region 3 (CDR3) comprising or consisting of an amino acid sequence defined by positions 118-126 of SEQ ID NO: 10; and
(b) a light chain variable region comprising:
a complementarity determining region 1 (CDR1) comprising or consisting of an amino acid sequence defined by positions 44-54 of SEQ ID NO: 11;
a complementarity determining region 2 (CDR2) comprising or consisting of an amino acid sequence defined by positions 70-76 of SEQ ID NO: 11;
a complementarity determining region 3 (CDR3) comprising or consisting of an amino acid sequence defined by positions 109-117 of SEQ ID NO: 11; and
antibodies of the population do not comprise a light chain variable region comprising:
a complementarity determining region 1 (CDR1) comprising or consisting of an amino acid sequence defined by positions 48-58 of SEQ ID NO: 12;
a complementarity determining region 2 (CDR2) comprising or consisting of an amino acid sequence defined by positions 74-80 of SEQ ID NO: 12;
a complementarity determining region 3 (CDR3) comprising or consisting of an amino acid sequence defined by positions 113-121 of SEQ ID NO: 12.

Embodiment 5

The method of embodiment 4, wherein the antibody population is produced by or otherwise identical to an antibody population as generated by hybridoma cells deposited on 22 Aug. 2014 at CellBank Australia (CBA) under accession number CBA20140026.

Embodiment 6

The method of embodiment 2, wherein said anti-glypican-1 antibody is not MIL-38.

Embodiment 7

The method of any one of embodiments 2 to 4, wherein said anti-glypican-1 antibody is an antibody fragment or recombinant antibody capable of binding glypican-1.

Embodiment 8

The method of any one of embodiments 2 to 7, wherein said anti-glypican-1 antibody is labeled.

Embodiment 9

The method of embodiment 8, wherein said label is chosen from a group consisting of a radiolabel, a fluorescent label, a biotin-avidin amplification system, a chemiluminescence system, microspheres, and colloidal gold.

Embodiment 10

The method of any one of embodiments 2 to 9, wherein anti-glypican-1 antibody binding is detected via a technique selected from the group consisting of immunofluorescence, radiolabeling, immunoblotting, Western blotting, enzyme-linked immunosorbant assay (ELISA), flow cytometry, immunoprecipitation, immunohistochemistry, biofilm test, affinity ring test, antibody array optical density test, and chemiluminescence.

Embodiment 11

The method of embodiment 1, wherein said level of glypican-1 in the body fluid sample from a patient is compared to the level of glypican-1 in a control sample; wherein increased anti-glypican-1 antibody binding of the body fluid sample over the control sample is associated with the presence of prostate cancer.

Embodiment 12

The method of embodiment 11, wherein a 50% or more increase in the level of glypican-1 of said body fluid sample over the level of glypican-1 in the control sample is indicative of prostate cancer.

Embodiment 13

The method of any one of embodiments 2 to 10, wherein anti-glypican-1 antibody binding to said body fluid sample is compared to anti-glypican-1 antibody binding of a control sample; wherein increased anti-glypican-1 antibody binding of the body fluid sample over the control sample is associated with the presence of prostate cancer.

Embodiment 14

The method of embodiment 13, wherein a 50% or more increase in the anti-glypican-1 antibody binding to said body fluid sample over the level of anti-glypican-1 antibody binding of the control sample is indicative of prostate cancer.

Embodiment 15

The method of any one of embodiments 2 to 10, 13 or 14 wherein anti-glypican-1 antibody binding to said body fluid sample is compared to anti-glypican-1 antibody binding to one or more glypican-1 standards; wherein the anti-glypican-1 antibody binding of the standards is used to quantify the amount of glypican-1 in said body fluid sample.

Embodiment 16

The method of any one of embodiments 1 to 15, wherein a glypican-1 content higher than about 10 ng/ml in the body fluid sample is indicative of prostate cancer.

Embodiment 17

The method of any one of embodiments 1 to 16, further comprising:
    measuring the level of prostate-specific antigen (PSA) in a body fluid sample from the patient, and
    determining that said patient has prostate cancer or an increased likelihood of developing prostate cancer based upon (i) the level of PSA measured in the body fluid sample, and (ii) binding of said anti-glypican-1 antibody to said body fluid sample.

Embodiment 18

The method of embodiment 17, wherein the level of prostate-specific antigen (PSA) is measured in a blood sample from the patient.

Embodiment 19

The method of embodiment 17 or embodiment 18, wherein the level of prostate-specific antigen (PSA) in the body fluid sample measured is compared to the level of PSA measured in a control sample; wherein increased PSA levels in the body fluid sample over the control sample is associated with the presence of prostate cancer.

Embodiment 20

The method of any one of embodiments 1 to 19, wherein said body fluid is selected from the group consisting of blood, serum, plasma, and urine.

Embodiment 21

A kit for detecting prostate cancer comprising a first anti-glypican-1 antibody, a pharmaceutically acceptable carrier, and glypican-1 standards; wherein said kit is capable of detecting glypican-1 in the body fluid of a patient.

Embodiment 22

The kit of embodiment 21, wherein the anti-glypican-1 antibody is not MIL-38.

Embodiment 23

The kit of embodiment 21, wherein the anti-glypican-1 antibody is MIL-38.

Embodiment 24

The kit of embodiment 21, wherein the anti-glypican-1 antibody is the antibody referred to in any one of embodiments 4, 5 or 7.

Embodiment 25

The kit of any one of embodiments 21 to 24, further comprising a secondary ligand.

Embodiment 26

The kit of embodiment 25, wherein said secondary ligand is a second anti-glypican-1 antibody or an aptamer capable of binding to glypican-1; wherein said second anti-glypican-1 antibody can be the same as the first anti-glypican-1 antibody.

Embodiment 27

The kit of embodiment 25 or embodiment 26, wherein said secondary ligand is conjugated to a label for rapid detection of said ligand.

Embodiment 28

The kit of embodiment 27, wherein said label is for use in a detection method selected from the group consisting of immunofluorescence, radiolabeling, immunoblotting, Western blotting, enzyme-linked immunosorbant assay (ELISA), flow cytometry, immunoprecipitation, immunohistochemistry, biofilm test, affinity ring test, antibody array optical density test, and chemiluminescence.

Embodiment 29

The kit of any one of embodiments 22 to 28, wherein the kit comprises components for conducting an ELISA.

BRIEF DESCRIPTION OF THE DRAWINGS

FIG. 1. Characterization of the cell bound MIL-38 glypican-1 antigen.
DU-145 prostate cancer cells were processed with a Membrane Protein Extraction Kit (MPEK, Merck) and incubated with the MIL-38 antibody attached to magnetic beads. The antigen was then immunoprecipitated and washed on the magnetic beads before eluting the antigen and subjecting said antigen to mass spectrometry analysis. Results of mass spec analysis are shown identifying glypican-1 as the MIL-38 antigen. The 18 unique peptide sequences spanning the glypican-1 protein are underlined.

FIG. 3. Mass spectrometry of size-exclusion chromatography purified MIL-38 antigen.
Fraction number A29 from size-exclusion chromatography separation of FIG. 2 was analyzed via mass spectrometry. Results of mass spec analysis are shown identifying glypican-1 as the MIL-38 antigen with 8 unique peptide sequences spanning the glypican-1 protein underlined.

FIG. 4. MIL-38 and anti-GPC-1 antibodies show overlapping reactivity on 2D gel western blot.

Membrane protein extracts of DU-145 prostate cancer cells were separated on 2D gel (pI gradient-horizontal, and molecular mass vertical). Western blots using MIL-38 antibody and commercial rGPC-1 rabbit polyclonal antibodies show overlapping reactivity marking a 60 Kd protein (circled in figure). Lane D is a one dimension separation for DU-145 extracts as a control. Lane M is a one dimension separation lane for molecular size markers as controls.

Figure 5:
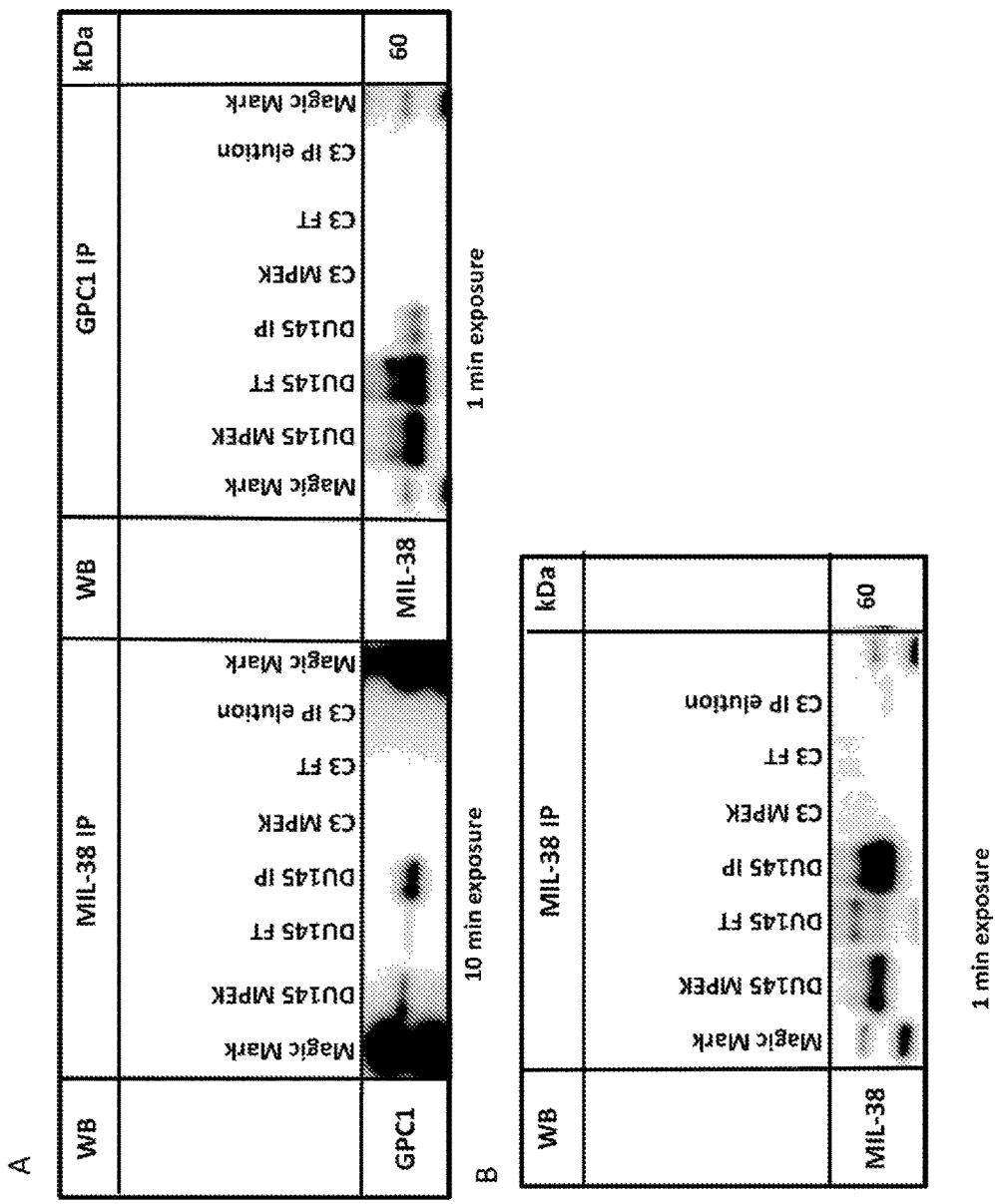

FIG. 5. MIL-38 can detect immunoprecipitates of GPC-1 antibodies and vice versa.

MIL-38 and rabbit anti-GPC-1 antibodies were each used to immunoprecipitate their antigens from DU-145 prostate cancer or C3 (MIL-38 negative) cell membrane protein extracts. Shown are the western blots of the immunoprecipitations detected with either MIL-38 or anti-GPC-1 antibody. FIG. 5A depicts GPC-1 detection of MIL-38 immunoprecipitates (left) and MIL-38 detection of GPC-1 immunoprecipitates (right). FIG. 5B depicts MIL-38 detection of MIL-38 immunoprecipitates as a control. Lanes are: Magic Mark—commercial protein marker as control; DU145 MPEK—prostate cancer membrane protein extract (not immunoprecipitated); DU145 FT—prostate cancer flow through from immune precipitation; DU145 IP-immunoprecipitate using antibody; C3 MPEK-(MIL-38 negative) control membrane protein extract (not immunoprecipitated); C3 FT-(MIL-38 negative) cell flow through from immune precipitation; C3 IP elution-(MIL-negative) cell immunoprecipitate using antibody. MIL-38 can detect the immunoprecipitate from rGPC-1 antibody and vice versa. MIL-38 can also bind to all controls including DU145 MPEK and to IP conducted by MIL-38.

Figure 6:
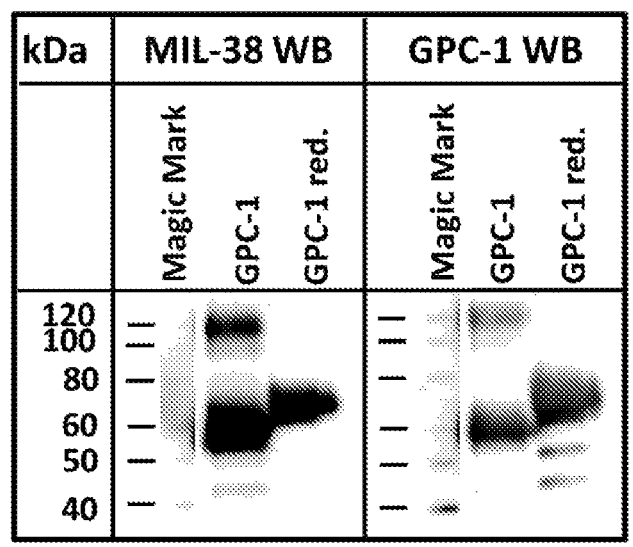

FIG. 6. MIL-38 detects recombinant glypican-1

A recombinant glypican-1 produced in NS0 cells was tested for reactivity with MIL-38 and anti-GPC-1 antibodies. Western blots show reactivity of both MIL-38 and rabbit polyclonal anti-GPC-1 antibody with the recombinant glypican-1. Lanes are: Magic Mark-commercial protein marker as control; GPC-1—recombinant Glypican-1 protein; GPC-1 red-recombinant Glypican-1 protein with reducing agent.

Figure 7:
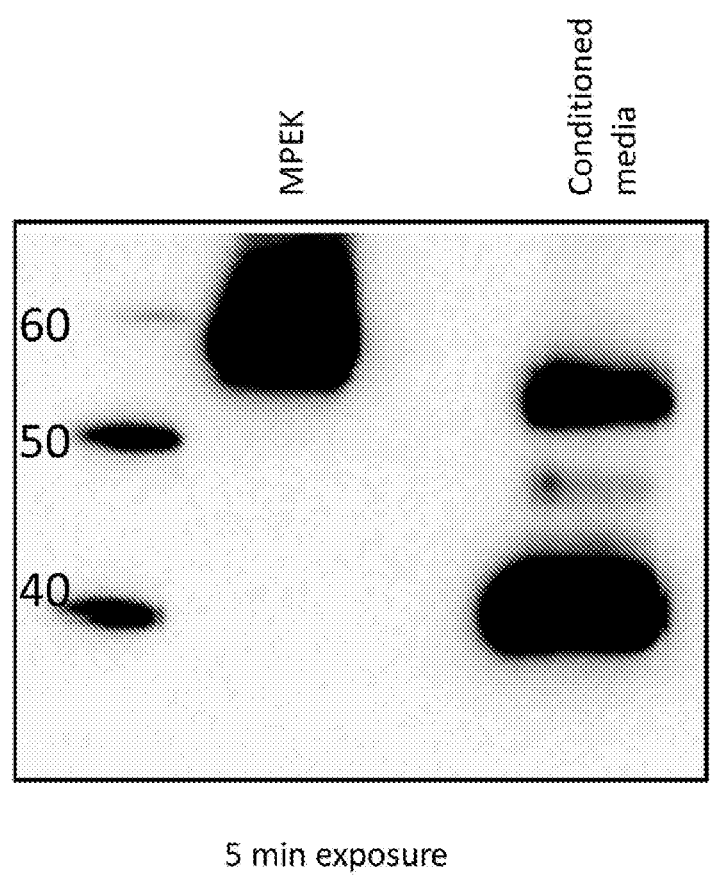

FIG. 7. MIL-38 can detect antigen secreted into cell culture supernatant.

DU-145 prostate cancer cells were incubated with serum free media for 36 hours to produce cell free conditioned media. The conditioned media without any cells was immunoprecipitated using the MIL-38 antibody and compared to a standard IP using DU-145 MPEK membrane protein extracts. Shown is a western blot of the immunoprecipitates using the MIL-38 antibody. The MIL-38 antibody can detect antigens of 40 and 55 kD in the conditioned liquid media.

FIG. 8. MIL-38 antigen detected in cell culture supernatant is glypican-1

DU-145 prostate cancer cells were incubated with serum free media for 36 hours to produce cell free conditioned media. The conditioned media was immunoprecipitated using the MIL-38 antibody and the immunoprecipitates were sent for mass spectrometry analysis. FIG. 8A. A sample containing both the 40 and 55 kD MIL-38 reactive antigens was subjected to mass spec analysis. Results of mass spec analysis are shown identifying glypican-1 as the MIL-38 antigen from the conditioned liquid media with 9 unique peptide sequences spanning the N-terminus of the glypican-1 protein underlined. FIG. 8B. A sample containing the 40 kDa MIL-38 reactive antigen was subjected to mass spec analysis. Results of mass spec analysis are shown identifying glypican-1 as the MIL-38 antigen from the conditioned liquid media with 10 unique peptide sequences spanning the N-terminus of the glypican-1 protein underlined. FIG. 8C. A sample containing the 55 kDa MIL-38 reactive antigen was subjected to mass spec analysis. Results of mass spec analysis are shown identifying glypican-1 as the MIL-38 antigen from the conditioned liquid media with 9 unique peptide sequences spanning the N-terminus of the glypican-1 protein underlined.

Figure 9:
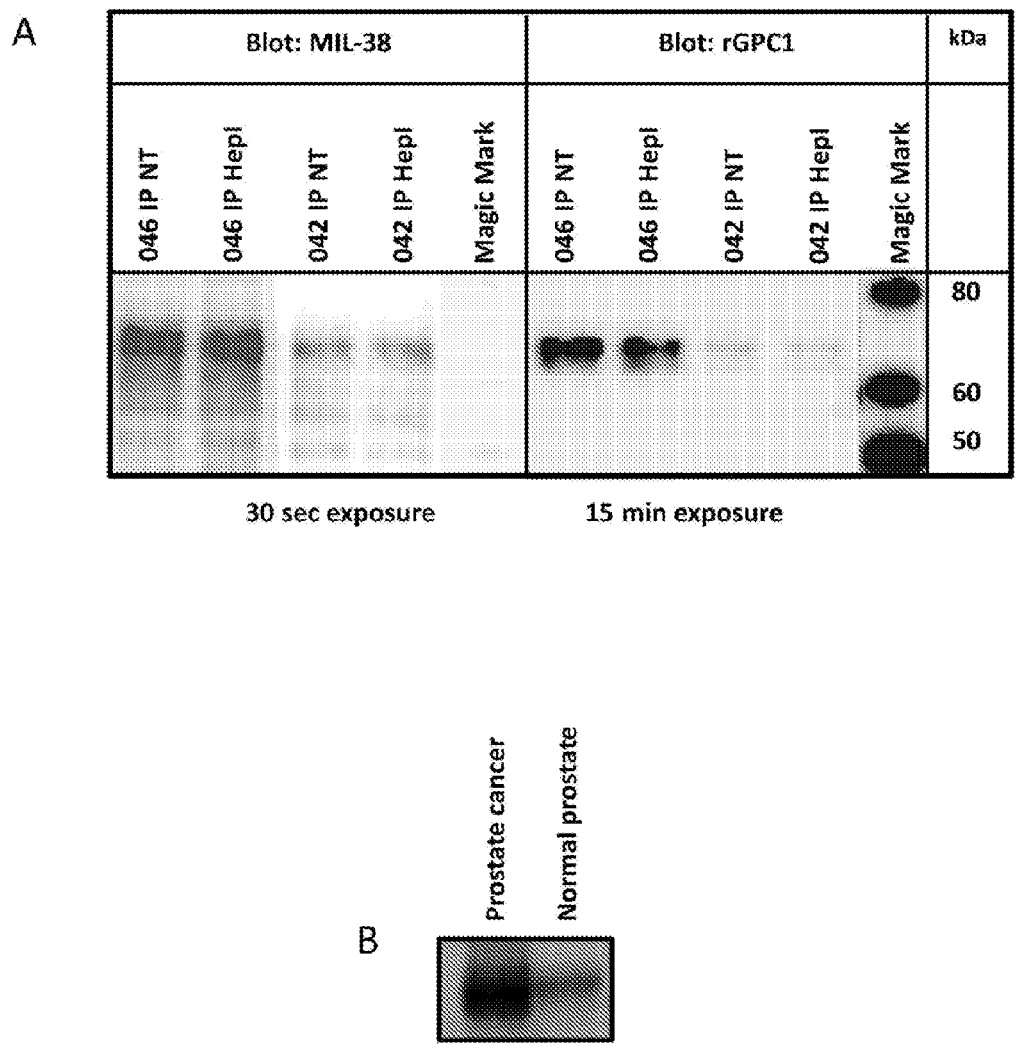

FIG. 9. MIL-38 antibody can detect glypican-1 in the plasma of prostate cancer patients and in membrane extracts of prostate cancers.

FIG. 9A. Plasma samples from one normal control patient and one prostate cancer patient were immunoprecipitated with the MIL-38 antibody. Shown are western blots with both the MIL-38 and rGPC1 antibodies. MIL-38 immunoprecipitated higher levels of glypican-1 protein in the plasma of the prostate cancer patient than the plasma of the control patient. Lanes are: 046 IP NT—IP from prostate cancer plasma; 046 IP HepI-IP from prostate cancer plasma treated with heparinase; 042 IP NT—IP from normal control plasma; 042 IP HepI-IP from normal control plasma treated with heparinase; Magic Mark-commercial protein marker as control. FIG. 9B. Membrane protein extracts from one normal prostate and one prostate cancer were obtained from Novus Bio. Equivalent amounts of protein were western blotted using MIL-38 antibody. The prostate cancer extract demonstrated higher expression of the MIL-38 antigen.

Figure 10:
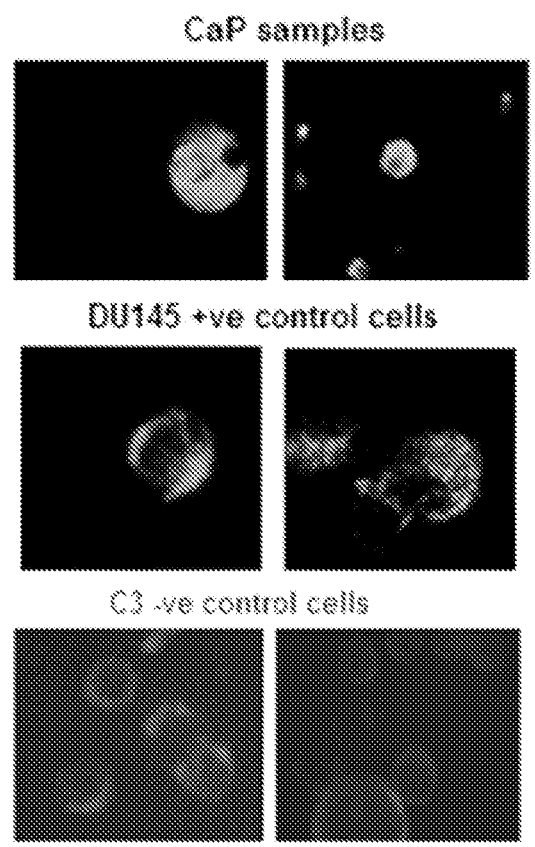

FIG. 10. MIL-38 can detect cancer in the urine of prostate cancer patients.

Urine samples from 125 age-matched patients were collected and tested for the presence of prostate cancer using MIL-38 antibody in an indirect immunofluorescence assay. Patients were classified as healthy controls, benign prostatic hypertrophy (BPH) or prostate cancer (CaP) based on either biopsy confirmation (BPH, CaP) or analysis of risk factors (healthy controls). Figure shows exemplary pictures of CaP experimental samples; DU145 positive control samples; and C3 negative control samples.

Figure 11:
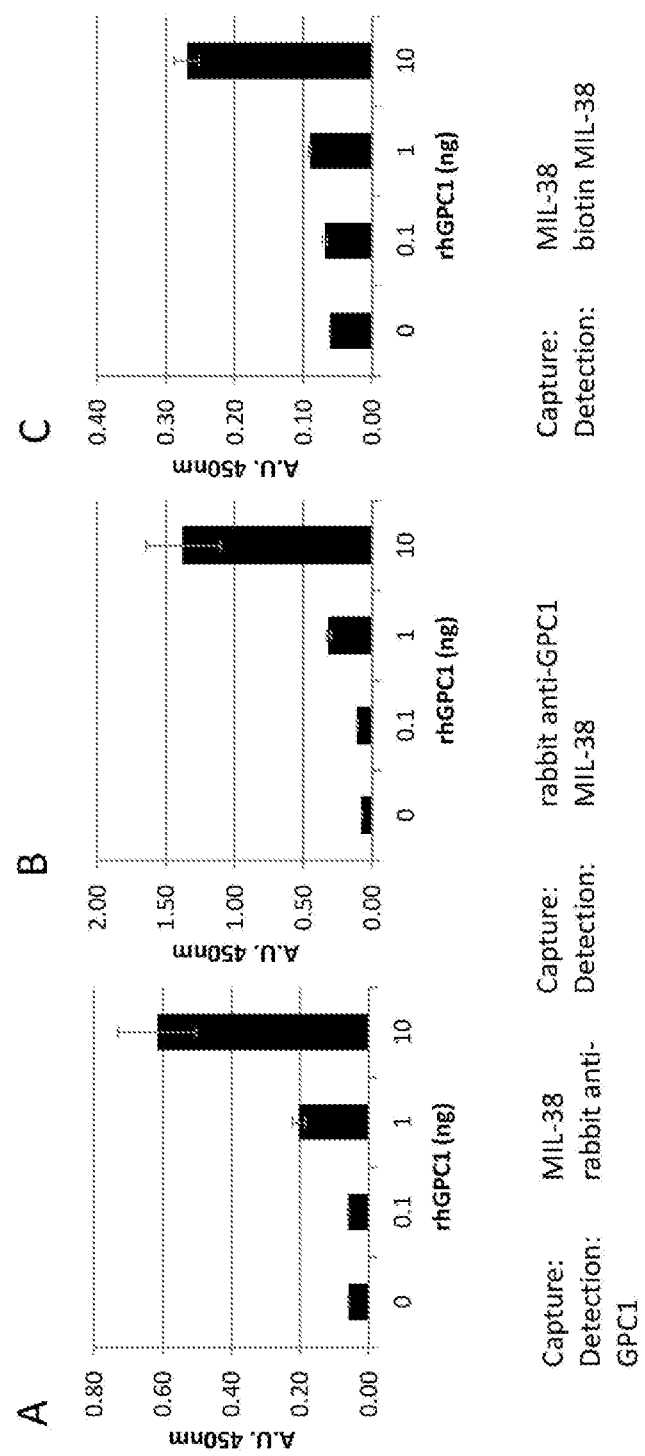

FIG. 11. MIL-38 can detect recombinant glypican-1 in a variety of ELISA formats

Sandwich ELISAs were performed using 0, 0.1, 1 or 10 ng recombinant human NS0-produced glypican-1 protein (rhGPC1) as analyte. FIG. 11A. Capture with MIL-38 antibody, detection with rabbit polyclonal anti-GPC1 (a-GPC1). FIG. 11B. Capture with anti-glypican-1 antibody, detection with MIL-38. FIG. 11C. Capture with MIL-38, detection with biotinylated MIL-38.

Figure 12:
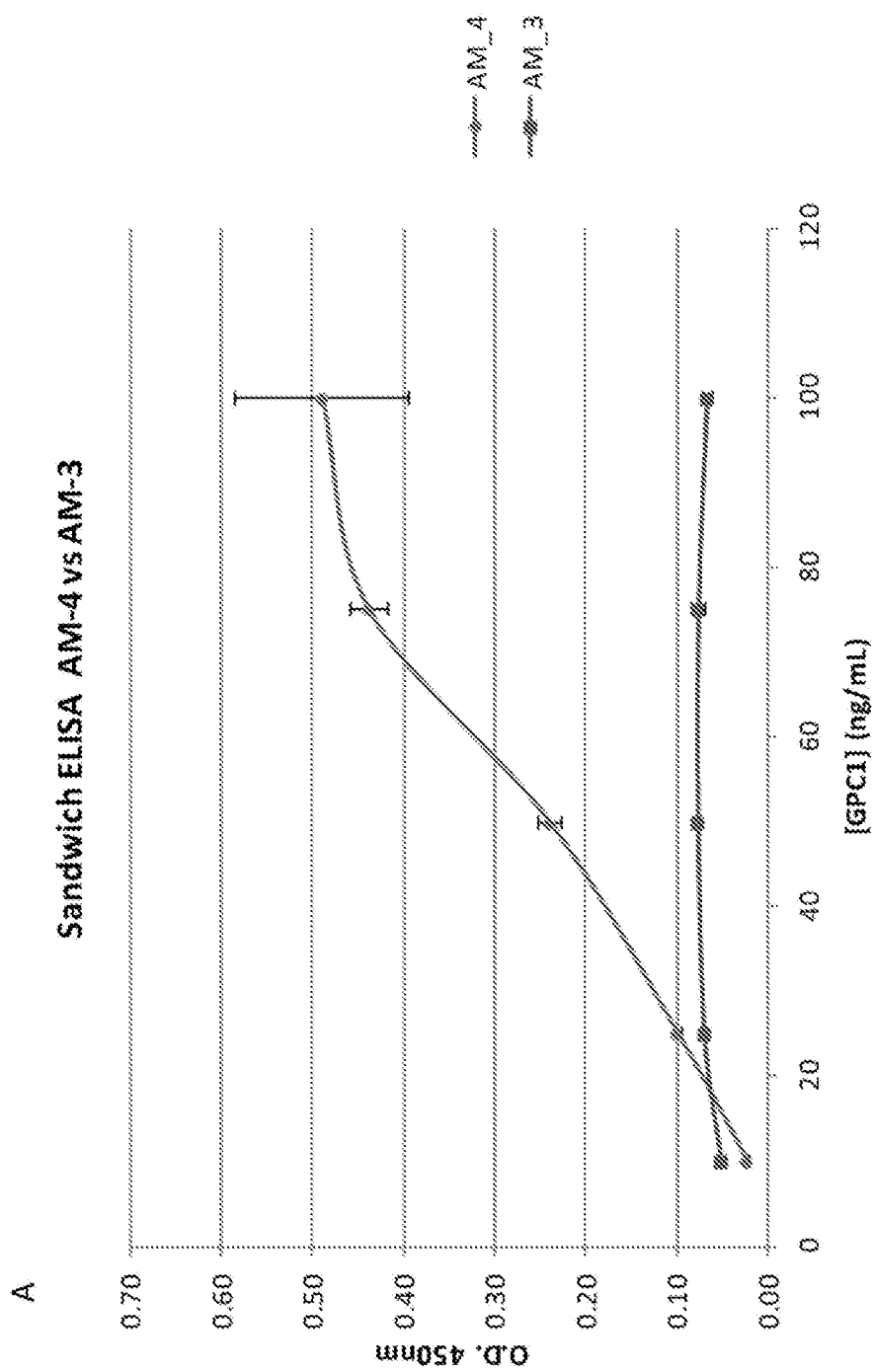
Figure 12:
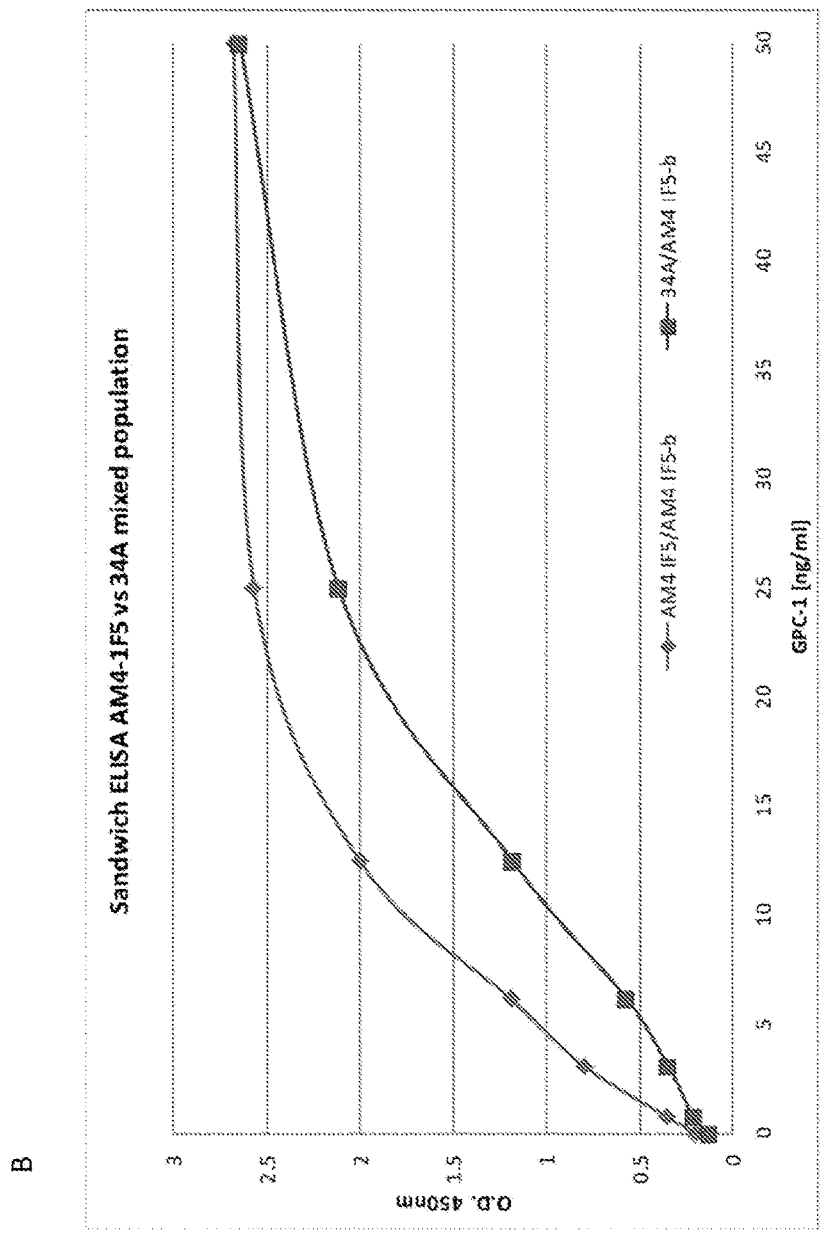

FIG. 12. Comparative sandwich ELISAs performed using different MIL-38 antibody preparations as capture antibodies.

FIG. 12A shows comparative sandwich ELISAs using AM3 and AM4 as capture antibodies. FIG. 12B shows comparative sandwich ELISAs using either a mixed preparation (34A) or a clonal population (AM4 1F5) as capture antibodies.

Figure 13:
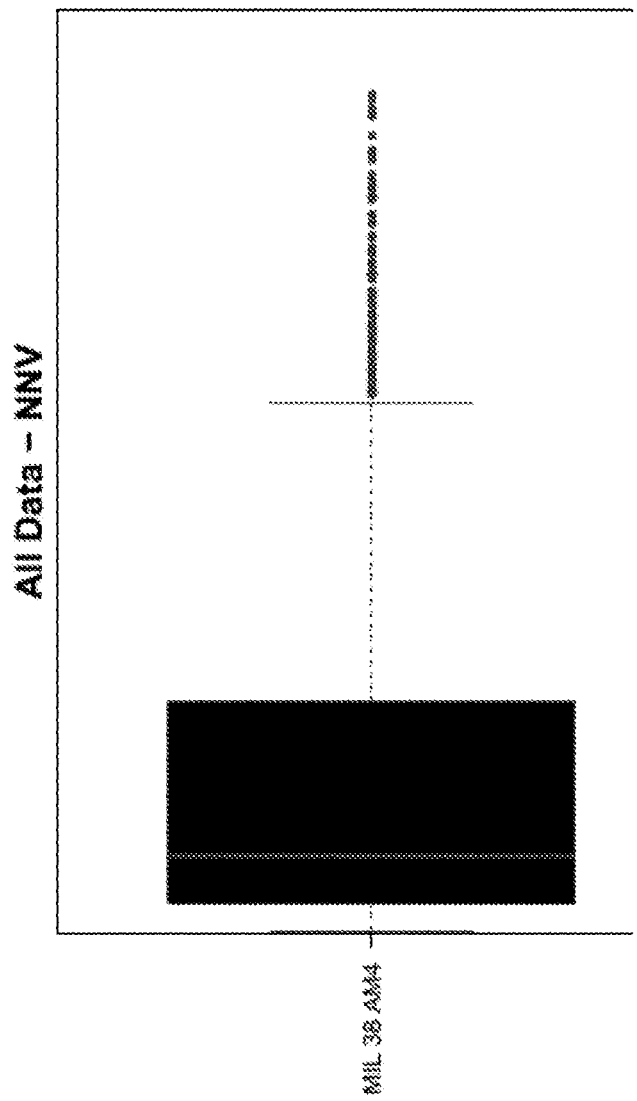

FIG. 13. Box plot graphs of raw data of antibody screening.

Figure 14:
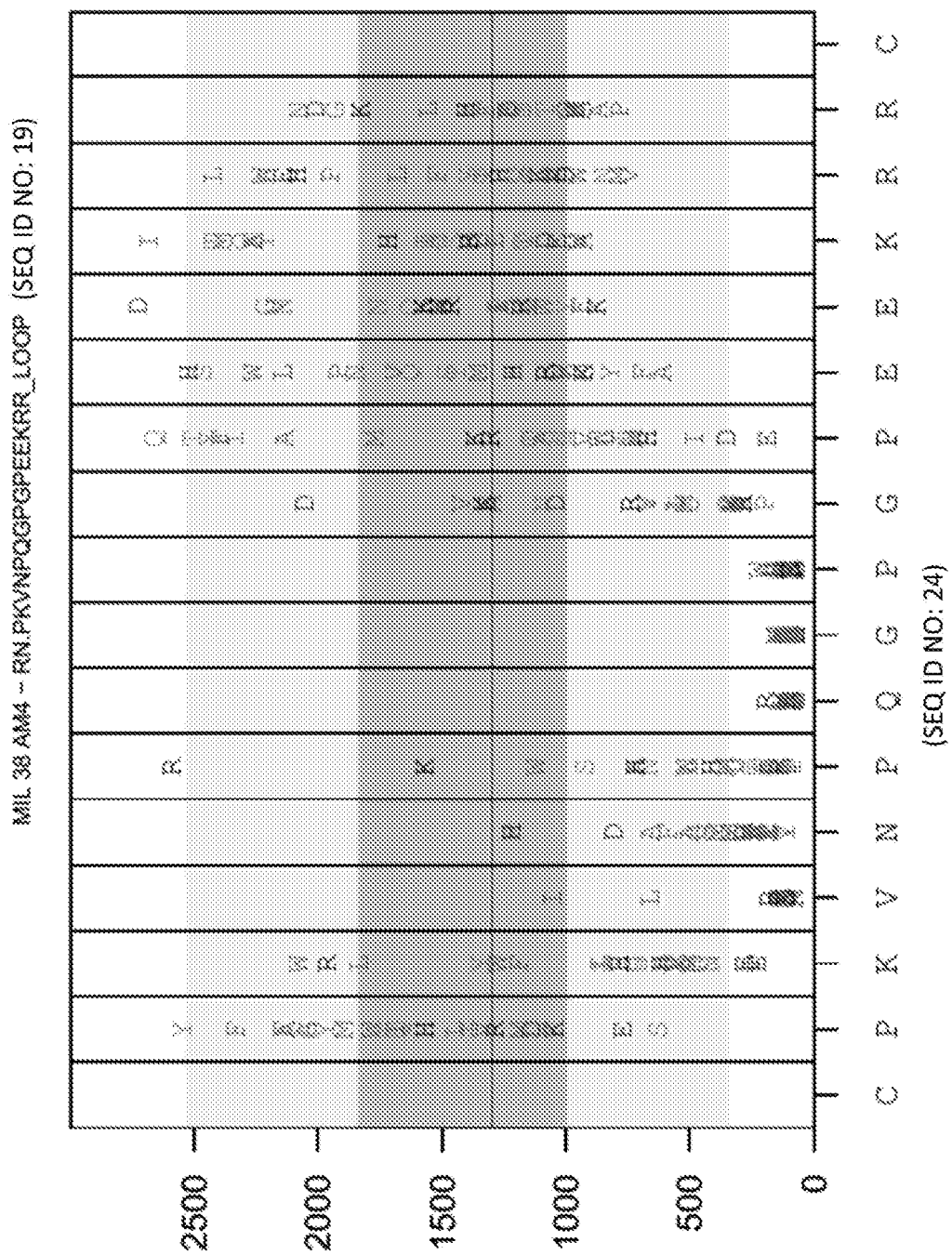

The binding of AM4 MIL-38 antibody to each of the synthesized peptides was tested in a PEPSCAN-based ELISA. The bottom and top of the boxes are the 25th and 75th percentile of the data. The band near the middle of the box is the 50th percentile (the median). The whiskers are at 1.5 the inter-quantile range, an indication of statistical outliers within the dataset (Mcgill et al., The American Statistician, 32: 12-16, 1978);

FIG. 14. Letterplot representation of MIL38-AM4 probed on the substitution analysis of set 3 (Example 13).

DETAILED DESCRIPTION

The present invention is based, in part, on the discovery that glypican-1 heparan sulfate proteoglycan (GPC-1) levels are elevated in the body fluids or cells of prostate cancer patients. The present inventors have discovered that glypican-1 is a new marker for prostate cancer. Accordingly, the present invention provides for methods of detecting the existence of prostate cancer in patients.

Normal human cells are only capable of forty to sixty cellular divisions before telomeric shortenings make them unviable. Prostate cancer cells however, are not subject to the Hayflick limit of divisions and continue to divide indefinitely causing abnormal growths.

The most common manifestation of cancer is the formation of tumors in the bodies of patients. In some embodiments of the present invention, the prostate cancer tumors can be painless and asymptomatic. In other embodiments, the tumors can cause physical discomfort or other localized symptoms such as fluid blockages or bleeding. In some embodiments, the prostate cancer of the present invention may cause systemic symptoms such as those caused by disrupting normal body functions. In other embodiments the symptoms of prostate cancers of the present invention can include change in bowel habits or bladder function.

One of the distinguishing factors between benign prostate tumors (non cancerous) and malignant prostate tumors (cancerous) is the ability to metastasize. Metastasis is the ability of cancers to spread (metastasize) to other parts of the body. Prostate cancer in patients is further categorized into stages according to the progression of the disease. The most common staging system is the TNM system, which categorizes cancer based on the size and extent of the primary tumor (T), the spread of the cancer to nearby lymph nodes (N), and the presence of secondary tumor formed by the metastasis (M) of the primary tumor to other parts of the body (American Cancer Society). Table 1 shows example definitions for each cancer stage.

TABLE 1

Definitions for cancer stages of the TNM system, adapted from the American Cancer Society.

| Stage | Definition |
| --- | --- |
| Stage 0 | Carcinoma in situ |
| Stage I, Stage II, and Stage III | Higher numbers indicate more extensive disease: Larger tumor size and/or spread of the cancer beyond the organ in which it first developed to nearby lymph nodes and/or tissues or organs adjacent to the location of the primary tumor |
| Stage IV | The cancer has spread to distant tissues or organs |

In some embodiments, the present invention can detect cancers at any one or more stages.

In some embodiments, the glypican-1 of the present invention is encoded by SEQ ID NO: 1. In some embodiments the glypican-1 protein is the full amino acid sequence of SEQ ID NO: 2. In some embodiments, the glypican-1 protein does not include the signal peptide of SEQ ID NO: 3. In some embodiments, the glypican-1 protein does not include the propeptide of SEQ ID NO: 4. In some embodiments, the glypican-1 protein of the present invention is SEQ ID NO: 5. In some embodiments glypican-1 of the present invention includes glypican-1 variants such as isoforms, splice variants, and allotypes. The present invention also provides a method of determining a prognosis for a patient with prostate cancer. In one embodiment, the method comprises obtaining a body fluid or tissue test sample from a patient, measuring the levels of glypican-1 in said body fluid or tissue, and comparing said levels with a fixed range of values wherein higher glypican-1 levels are associated with poorer prognosis or less favorable patient outcome.

Non-limiting examples of prostate cancers that may be detected with the present invention include prostatic intra-epithelial neoplasia, adenocarcinoma, leiomyosarcoma, and rhabdomyosarcoma One of the most powerful tools against cancer is early detection. Earlier stages of cancer tend to be easier to treat, and the prognosis for most cancers is generally better if the disease is still localized. There are many tests that can help diagnose cancer. In some embodiments, the present invention uses glypican-1 alone to detect prostate cancer. In other embodiments GPC-1 is used together with another antigen wherein the presence of prostate cancer is determined by the detection of both antigens. In one embodiment, the other antigen is PSA.

The present invention provides methods for detecting prostate cancer. Prostate cancer is the most frequently diagnosed visceral cancer and the second leading cause of cancer death for men in the United States. The American Cancer Society estimates that in 2013 about 238,590 new cases of prostate cancer will be diagnosed and 29,720 men will die of the disease. Overall, one is six men will be diagnosed with prostate cancer in their lifetime. Prostate cancers have been associated with many symptoms including difficulty urinating, erectile dysfunction and pain. Although most prostate cancers are slow growing, there are cases of aggressive prostate cancers which can metastasize and can ultimately lead to death.

There are two major prostate cancer detection tests currently used by medical professionals: a digital rectal exam (DRE), and the measurement of prostate-specific antigen (PSA) in the blood of patients. Unfortunately, neither of these tests is entirely conclusive and both can result in false negatives (leaving real cancers undetected), and false positives (signaling cancer where there is none). For example, standard PSA tests conducted at the recommended 4.0 ng/ml cutoff are 86% sensitive to cancer patients but only 33% specific, producing false positives in roughly 67% of non-cancer patients (Hoffman et al. 2002). The present invention describes methods for combining glypican-1 measurements with another prostate cancer antigen, PSA, wherein the presence of prostate cancer is determined based on the levels of glypican-1 in the body fluid or tissue of the patient and the results of the PSA test.

BLCA-38 (also known as MIL-38) is an $IgG_1$ murine raised antibody against human bladder cancer cell line UCRU-BL-17CL (Walker et al., 1989). The resulting antibody was shown to bind to most human bladder cancer lines (Russell et al., 2004). The antibody was described as binding a cell surface protein of 30 Kd and to be useful in detecting certain kinds of bladder carcinoma (U.S. Pat. No. 5,622, 836).

The present invention describes for the first time the identity of the MIL-38 antigen. The present inventors discovered the antigen through a series of immunoprecipitations, westerns blot analyses, mass spectrometry analyses, and 2D gels described below in Examples 1-8. In accordance with the present invention, any suitable agent and/or any suitable technique as known to those of skill in the art can be used to measure the levels of glypican-1 in a given sample (e.g. a body fluid sample), and use the measurement to diagnose and/or prognose prostate cancer in a patient from which the sample is derived. In some embodiments, the agent is an anti-glypican-1 antibody. In some embodiments of the invention MIL-38 antibody is used to bind to and detect a 60 kD glypican-1 proteoglycan. In some embodiments the MIL-38 antibody is used to detect the glypican-1 antigen on the surface of prostate cancer cells. In other embodiments, the MIL-38 antibody is used to detect soluble glypican-1 in the body fluids or tissues of prostate cancer patients. In some embodiments, the MIL-38 antibody has binding specificity for a glypican-1 epitope comprising a first segment KVNPQGPGPE (SEQ ID NO: 6) or KVNPQGPGP (SEQ ID NO: 7). The epitope may further comprise a second segment TQNARA (SEQ ID NO: 8) or TQNARAFRD (SEQ ID NO: 9). The present invention shows that MIL-38's ability to bind to prostate cancer tissue is based on the presence of the glypican-1 antigen and further demonstrates the use of other anti-glypican-1 antibodies to detect cancerous prostate cells. Therefore in some embodiments the anti-glypican-1 antibody is not MIL-38. Further the present invention demonstrates the ability to detect prostate cancer by detecting glypican-1 levels in the body fluids or tissues of patients. The present inventors have thus discovered that glypican-1 is a marker for prostate cancer.

According to the invention glypican-1 levels in body fluids or tissues can be detected using any suitable technique (e.g. any proteomic technique). In some embodiments, the glypican-1 levels can be detected using an anti-glypican-1 antibody. For example, the glypican-1 levels can be detected using an anti-glypican-1 antibody that comprises: a heavy chain variable region comprising a complementarity determining region 1 (CDR1) comprising or consisting of an amino acid sequence defined by positions 50-54 of SEQ ID NO: 10; a complementarity determining region 2 (CDR2) comprising or consisting of an amino acid sequence defined by positions 69-85 of SEQ ID NO: 10; a complementarity determining region 3 (CDR3) comprising or consisting of an amino acid sequence defined by positions 118-126 of SEQ ID NO: 10; and comprise a light chain variable region comprising a complementarity determining region 1 (CDR1) comprising or consisting of an amino acid sequence defined by positions 44-54 of SEQ ID NO: 11; a complementarity determining region 2 (CDR2) comprising or consisting of an amino acid sequence defined by positions 70-76 of SEQ ID NO: 11; a complementarity determining region 3 (CDR3) comprising or consisting of an amino acid sequence defined by positions 109-117 of SEQ ID NO: 11. The anti-glypican-1 antibody used to detect the glypican-1 levels may not comprise: a light chain variable region comprising a complementarity determining region 1 (CDR1) comprising or consisting of an amino acid sequence defined by positions 48-58 of SEQ ID NO: 12; a complementarity determining region 2 (CDR2) comprising or consisting of an amino acid sequence defined by positions 74-80 of SEQ ID NO: 12; and a complementarity determining region 3 (CDR3) comprising or consisting of an amino acid sequence defined by positions 113-121 of SEQ ID NO: 12. The anti-glypican-1 antibody may be produced by or otherwise identical to an antibody generated by hybridoma cells as deposited on 22 Aug. 2014 at CellBank Australia (CBA) under accession number CBA20140026.

In some embodiments of the invention, one or more other anti-glypican-1 antibodies may be used to detect glypican-1 in the body fluids or tissues of patients. In some embodiments, said other anti-glypican-1 antibodies can be any of the antibodies listed in (Table 2) of this application. In yet another embodiment, the antibody used to detect glypican-1 in the body fluids or tissues of patients could be any antibody capable of binding glypican-1. In some embodiments the antibodies of the present invention include antibody fragments or recombinant antibodies. In some embodiments the antibodies of the present invention include human antibodies, humanized antibodies and chimeric antibodies. In some embodiments the antibodies of the present invention are conjugated antibodies. A non-limiting list of the antibody fragments of the present invention include fragment antigen binding Fab, F(ab')$_2$, ScFv, Di-scFv sdAb, chemically linked F(ab')$_2$, bispecific antibodies, trispecific antibodies Fab3, Bis-scFv, Minibody bivalent antibodies, triabody trivalent antibodies, diabody bispecific antibodies, tetrabody tetravalent antibodies. A review of antibody fragments and domain combinations can be found in (Holliger and Hudson 2005, and US 2003/0077282).

TABLE 2

Anti-Glypican-1 Antibodies

| Company | Cat# | Reactivity | Use | Host | M/P | Binding specificity | Immunogen |
|---|---|---|---|---|---|---|---|
| R&D | BAF4519 | Human | WB, FC | Goat | poly | aa24-530 | mouse myeloma cell line NS0-derived recombinant human Glypican-1, Asp24-Ser530 (Accession# P35052) |
| Bioss | bs-2426R-Biotin | Human, mouse, rat, dog, cow, horse | WB, ELISA, IHC-P&F | Rabbit | poly | | Unknown immunogen, Biotin conjugated |
| Bioss | bs-2426-HRP | Human, mouse, rat, dog, cow, horse | WB, ELISA, IHC-P&F | Rabbit | poly | | Unknown immunogen, HRP conjugated |
| antibodies-online | ABIN740102 | Human, mouse, rat, dog, cow, horse | WB, ELISA, IHC-P&F | Rabbit | poly | C-term | Synthetic peptide derived from human glypican 1 C-terminus. Biotin conjugated. |
| antibodies-online | ABIN1174125 | Human | IHC, WB, ELISA | Rabbit | poly | | Unknown immunogen. Biotin conjugated |
| antibodies-online | ABIN740109 | Human, mouse, rat, dog, cow, horse | WB, ELISA, IHC-P&F | Rabbit | poly | C-term | Synthetic peptide derived from human glypican 1 C-terminus. Enquire about sequence info. HRP conjugated |
| antibodies-online | ABIN653109 | Human | WB, IHC, FACS, ELISA | Rabbit | poly | N-term | KLH conjugated sythetic peptide between 12-41aa from the N-terminal region of human Glypican-1 |

TABLE 2-continued

Anti-Glypican-1 Antibodies

| Company | Cat# | Reactivity | Use | Host | M/P | Binding specificity | Immunogen |
|---|---|---|---|---|---|---|---|
| antibodies-online | ABIN952553 | human | ELISA, IHC-p, WB, FACS | Rabbit | poly | N-term | KLH conjugated synthetic peptide between 12-41aa from the N-terminal region of human Glypican-1 |
| antibodies-online | ABIN797896 | human | IHC, WB | Rabbit | poly | N-term | synthetic peptide derived from N-terminal domain of human GPC1 |
| antibodies-online | ABIN347483 | mouse, rat, human | IHC, WB | Rabbit | poly | N-term | synthetic peptide derived from N-terminal domain of human GPC1 |
| antibodies-online | ABIN347484 | human | IHC, WB, ICC, ELISA | Rabbit | poly | N-term | synthetic peptide derived from N-terminal domain of human GPC1 |
| antibodies-online | ABIN740100 | Human, mouse, rat, dog, cow, horse | WB, ELISA, IHC-P&F, IF | Rabbit | poly | C-term | Synthetic peptide derived from human glypican 1 C-terminus. Enquire about sequence info. |
| antibodies-online | ABIN207433 | human | WB, ELISA | Rabbit | poly | C-term | synthetic peptide corresponding to C-terminal residues of human GPC1 precursor |
| antibodies-online | ABIN964659 | human, mouse, rat | WB, ELISA | Rabbit | poly | internal region | synthetic peptide corresponding to an internal region of human GPC-1 |
| antibodies-online | ABIN349638 | human | WB, ELISA | Rabbit | poly | internal region | synthetic peptide corresponding to human GPC1 |
| antibodies-online | ABIN1101824 | human | WB, ELISA | Rabbit | poly | internal region | synthetic peptide corresponding to an internal region of human GPC-1 |
| antibodies-online | ABIN595376 | human | WB, ELISA | Rabbit | poly | internal region | synthetic peptide corresponding to an internal region of human GPC-1 |
| antibodies-online | ABIN330371 | human | WB, ELISA | goat | poly | aa24-530 | NS0-derived rhGlypican 1 aa24-530 |
| antibodies-online | ABIN1479675 | human | FACS, IHC, WB, ELISA | Rabbit | poly | aa12-41 | KLH conjugated synthetic peptide from N-terminal region of human GPC1 |

In some aspects of the invention, a new anti-glypican-1 antibody can be generated from glypican-1 protein or a fragment or derivative thereof. By way of non-limiting example only, the anti-glypican-1 antibody can be raised against a glypican-1 epitope comprising a first segment KVNPQGPGPE (SEQ ID NO: 6) or KVNPQGPGP (SEQ ID NO: 7). The epitope may further comprise a second segment TQNARA (SEQ ID NO: 8) or TQNARAFRD (SEQ ID NO: 9). One skilled in the art will recognize that many procedures are available for the production of antibodies, for example, the methods described in (Harlow et al., 1988). In some embodiments, the glypican-1 immunogen used to create the anti-glypican-1 antibodies will include the post translational modifications of the native protein (e.g. folding). In some embodiments the glypican-1 immunogen will not include the signal peptide (SEQ ID No: 3), or the C-terminal propeptide (SEQ ID No: 4) sequences. In some embodiments, the glypican-1 immunogens are obtained from human or other mammalian cells such as transformed murine NS0, wild type DU-145, or other glypican-1 expressing cell line. In some embodiments the glypican-1 antigen can be cells expressing glypican-1. In some embodiments the glypican-1 immunogen can be whole cells or cell parts with glypican-1 protein on their surface. One skilled in the art will also appreciate that binding fragments or Fab fragments can be prepared from genetic information by various well-known procedures such as those described in (Borrebaeck et al., 1995; and U.S. Pat. No. 7,960,517).

In another embodiment of the present invention, polyclonal antibodies targeting glypican-1 may be created for the detection of prostate cancer. Again by way of non-limiting example only, the polyclonal antibody targeting glypican-1 can be raised against a series of glypican-1 epitopes including a glypican-1 epitope comprising a first segment KVNPQGPGPE (SEQ ID NO: 6) or KVNPQGPGP (SEQ ID NO: 7). The epitope may further comprise a second segment TQNARA (SEQ ID NO: 8) or TQNARAFRD (SEQ ID NO: 9). Various procedures known in the art may be used for the production of polyclonal antibodies to glypican-1 or a fragment of glypican-1. In one embodiment of the invention, the glypican-1 protein or fragment thereof may be injected into a host animal. In some embodiments the host animals can include but are not limited to rabbits, mice, rats, etc. In some embodiments the resulting sera is purified and tested for its ability to react with glypican-1 via techniques well known in the art such as westerns, ELISAs, immunofluorescence screens, flow cytometry, Fluorescence Activated Cell Sorting (FACS) or others.

In another embodiment, monoclonal antibodies (mAbs) directed against glypican-1 may be created for the detection of prostate cancer. Again by way of non-limiting example only, the monoclonal antibody targeting glypican can be raised against a glypican-1 epitope comprising a first segment KVNPQGPGPE (SEQ ID NO: 6) or KVNPQGPGP (SEQ ID NO: 7). The epitope may further comprise a second segment TQNARA (SEQ ID NO: 8) or TQNARAFRD (SEQ ID NO: 9). In one embodiment, anti-glypican-1 antibodies are created via the hybridoma technique (Kohler and Milstein 1975), or other techniques (Cole et al., 1985; or U.S. Pat. No. 6,116,013). For more details and examples on antibody production see U.S. Pat. No. 7,985,560.

In some embodiments of the present invention, glypican-1 is detected in the body fluids or tissues of patients by an anti-glypican-1 antibody. In some embodiments the body fluid sample obtained from the patient is a blood, serum, plasma, or urine sample. In other embodiments, glypican-1 is detected in tissue samples of patients. In some embodiments, the tissue samples include tumor biopsies or other patient tissue. In some aspects of this invention, the antibody detects glypican-1 via Western blot analysis, Enzyme-linked immunosorbent assays (ELISAs), fluorescent cell sorting or FACS, immunofluorescence, radiolabeling, immunoprecipitation, immunohistochemistry, immunoblotting, chemiluminescence, and/or other known techniques to detect protein with an antibody or other ligand such as a protein capable of binding glypican-1. In some embodiments, glypican-1 is detected via a biofilm test, or affinity ring test as described in US application 2013/016,736. In some embodiments glypican-1 is detected via glypican-1 binding agents coated to transparent surfaces (e.g. polycarbonate slides). Binding of glypican-1 or glypican-1 bearing cells can be detected by changes in optical density. In some embodiments, anti-glypican-1 antibody binding to said body fluid or tissue sample is compared to the anti-glypican-1 antibody binding to one or more glypican-1 calibration standards; wherein the anti-glypican-1 antibody binding of the calibration standards is used to quantify the amount of glypican-1 in said body fluid sample. In one embodiment, the calibration standards comprise one or more samples with known glypican-1 concentrations.

In some embodiments the measurement of glypican-1 is accomplished by contacting said body fluid or tissue sample with a glypican-1 ligand. In some embodiments the ligand can be an anti-glypican-1 antibody capable of binding the glypican-1 proteoglycan.

In some embodiments, the tissue or body fluid of a patient may require a pre-treatment prior to detection by the anti-glypican-1 ligand. In some embodiments, said pre-treatment may include treatment with agents such as heparinase PNGaseF, N-Glycosidase, alkaline phosphatase, or hepari-tinase among others. In other embodiments, said pre-treatment may include tissue lysis, membrane purification, blood plasma or serum fractionation, cell purification, or protein purification among others.

In some embodiments the measured levels of glypican-1 in the body fluid or tissue of a patient are compared against a control sample of body fluid or tissue from a cancer-free patient. In other embodiments the measured levels of glypican-1 in the body fluid or tissue of a patient are compared against pre-determined reference values or ranges of reference values. In other embodiments, the levels of glypican-1 in body fluids or tissues of a patient are indicative of prostate tumor size, or progression.

In some embodiments, the detection of glypican-1 from body fluid or tissue samples is conducted via Enzyme-linked immunosorbent assays (ELISAs). ELISAs comprise those based on colorimetry, chemiluminescence, and fluorometry. ELISAs have been successfully applied in the determination of low amounts of drugs and other antigenic components in body tissues or fluids such as blood, serum, and plasma samples, and are well known in the art. An ELISA that is useful in the present invention may employ any suitable capture reagent and detectable reagent including antibodies and derivatives thereof, protein ligands and the like. In certain embodiments, the ELISA is cell-based. In other embodiments, the ELISA detects cell-free antigens. In some embodiments the biological sample suspected of containing glypican-1 is contacted and incubated with the capture (or coat) antibodies so that the capture antibodies capture or bind to the glypican-1. The detection step involves use of the detectable antibody or detectable protein ligands, which can bind to said glypican-1 and be used to detect the presence or amount of glypican-1 based on detection of its label.

In some embodiments, the biological sample is contacted and incubated with the immobilized capture (or coat) reagent, which can be a glypican-1 antibody. This antibody may be from any species, but in some embodiments the antibody is a murine or rat antibody. In other embodiments the antibody is a murine antibody. In other embodiments the antibody is derived from a hybridoma. In some embodiments, the glypican-1 antibody is a recombinant antibody or antibody fragment. Immobilization conventionally is accomplished by insolubilizing the capture reagent either before the assay procedure, as by adsorption to a water-insoluble matrix or surface (U.S. Pat. No. 3,720,760) or non-covalent or covalent coupling (for example, using glutaraldehyde or carbodiimide cross-linking, with or without prior activation of the support with, e.g., nitric acid and a reducing agent as described in U.S. Pat. No. 3,645,852 or in Rotmans et al., 1983), or afterward, e.g., by immunoprecipitation.

In some embodiments, the solid phase used for immobilization may be any inert support or carrier that is essentially water insoluble and useful in immunometric assays, including supports in the form of, e.g., surfaces, particles, porous matrices, etc. Examples of commonly used supports include small sheets, Sephadex, polyvinyl chloride, plastic beads, and assay plates or test tubes manufactured from polyethylene, polypropylene, polystyrene, and the like including 96-well microtiter plates, as well as particulate materials such as filter paper, agarose, cross-linked dextran, and other polysaccharides. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are suitably employed for capture reagent immobilization. In one embodiment the immobilized capture reagent is coated on a microtiter plate, and in particular the solid phase used is a multi-well microtiter plate that can be used to analyze several samples at one time, e.g., a microtest 96-well ELISA plate such as that sold as Nunc Maxisorb or Immulon. In certain embodiments, the plate is a MICROTEST™ or MAXISORP™ 96-well ELISA plate such as that sold as NUNC MAXISORB™ or IMMULON™.

In some embodiments the solid phase is coated with the capture reagent as defined above, which may be linked by a non-covalent or covalent interaction or physical linkage as desired. Techniques for attachment include those described in U.S. Pat. No. 4,376,110 and the references cited therein. If covalent, the plate or other solid phase is incubated with a cross-linking agent together with the capture reagent under conditions well known in the art, e.g., such as for 1 hour at room temperature.

In other embodiments, commonly used cross-linking agents for attaching the capture reagent to the solid phase substrate include, e.g., 1,1-bis(diazoacetyl)-2-phenylethane, glutaraldehyde, N-hydroxy-succinimide esters, for example, esters with 4-azido-salicylic acid, homobifunctional imidoesters, including disuccinimidyl esters such as 3,3'-dithiobis-(succinimidyl-propionate), and bifunctional maleimides such as bis-N-maleimido-1,8-octane. Derivatizing agents such as methyl-3-[(p-azidophenyl)-dithio]pro-pi-oimi-date yield photoactivatable intermediates capable of forming cross-links in the presence of light.

In some embodiments, 96-well plates are utilized. In some embodiments the 96-well plates are coated with the capture reagent (typically diluted in a buffer such as 0.05 M sodium carbonate by incubation for at least about 10 hours, more preferably at least overnight, at temperatures of about 4-20° C., or about 4-8° C., and at a pH of about 8-12, or about pH 9-10, or about pH 9.6). If shorter coating times are desired, in some embodiments the plate can be coated for less time, e.g. at room temperature for two hours or less. In some embodiments, the plates may be stacked and coated long in advance of the assay itself, and then the assay can be carried out simultaneously on several samples in a manual, semi-automatic, or automatic fashion, such as by using robotics.

In some embodiments, the coated plates can be treated with a blocking agent that binds non-specifically to and saturates the binding sites to prevent unwanted binding of the free ligand to the excess sites on the wells of the plate. Non-limiting examples of appropriate blocking agents for this purpose include, e.g., gelatin, bovine serum albumin, egg albumin, casein, and non-fat milk. In some embodiments the blocking treatment can take place under conditions of ambient temperatures for about 1-4 hours. In other embodiments the blocking can take place over the course of 1 to 3 hours or less. In other embodiments the blocking can take place overnight at 0-4° C.

In some embodiments the glypican-1 standard (e.g. purified glypican-1 protein) or the biological sample to be analyzed, appropriately diluted, is added to the immobilized phase. In some embodiments, the dilution rate is about 1-15% by volume. In some embodiments, the glypican-1 protein standard will include the post-translational modifications of the native protein. In some embodiments, the glypican-1 protein standards are obtained from human or other mammalian cells such as transformed NS0, wild type DU-145, or other glypican-1 expressing cell line. In other embodiments, the glypican-1 protein may be purified from body fluids or tissues. In some embodiments, the glypican-1 standard will be a partial glypican-1 peptide or other epitope detected by the glypican-1 detection antibody, or ligand. In some embodiments the standard can be a cell expressing glypican-1. In some embodiments the dilution is about 10% by volume. A non-limiting group of buffers that may be used for dilution for this purpose include (a) PBS containing 0.5% BSA, 0.05% TWEEN 20™ detergent (P20), 0.05% PROCLIN™ 300 antibiotic, 5 mM EDTA, 0.25% CHAPS surfactant, 0.2% bovine γ-globulins, and 0.35M NaCl, pH 7.4; (b) PBS containing 0.5% bovine serum albumin, 0.05% polysorbate 20, 5 mM EDTA, 0.25% CHAPS, 0.2% bovine γ-globulins, and 0.35 M NaCl; pH 7.4 (c) PBS containing 0.5% BSA, 0.05% polysorbate 20 (P20), and 0.05% PROCLIN™ 300, pH 7; (d) PBS containing 0.5% BSA, 0.05% P20, 0.05% PROCLIN™ 300, 5 mM EDTA, and 0.35 M NaCl, pH 6.35; (e) PBS containing 0.5% BSA, 0.05% P20, 0.05% PROCLIN™ 300, 5 mM EDTA, 0.2% bovine γ-globulins, and 0.35 M NaCl, pH 7.4; and (f) PBS containing 0.5% BSA, 0.05% P20, 0.05% PROCLIN™ 300, 5 mM EDTA, 0.25% CHAPS, and 0.35 M NaCl, pH 7.4. PROCLIN™ 300 acts as a preservative, and TWEEN 20™ acts as a detergent to eliminate non-specific binding.

While the concentration of the capture reagents will generally be determined by the concentration range of interest of the glypican-1 taking any necessary dilution of the biological sample into account, the final concentration of the capture reagent will normally be determined empirically to maximize the sensitivity of the assay over the range of interest.

The conditions for incubation of sample and immobilized capture reagent are selected to maximize sensitivity of the assay and to minimize dissociation. In some embodiments, the incubation is accomplished at fairly constant temperatures, ranging from about 0° C. to about 40° C. In other embodiments the incubation is conducted from about 20 to 25° C. The time for incubation depends primarily on the temperature, being generally no greater than about 10 hours to avoid an insensitive assay. In some embodiments the incubation time is from about 0.5 to 3 hours. In other embodiments the incubation is about 1.5-3 hours or less at room temperature to maximize binding of free glypican-1 to capture reagents. The duration of incubation may be longer if a protease inhibitor is added to prevent proteases in the biological fluid from degrading the glypican-1.

In some embodiments, the detection method is a competitive ELISA. In some embodiments the incubation step includes the addition of unbound and unlabeled antibody. In some embodiments the known concentration of unlabeled antibody binds the free glypican-1 antigen and prevents it from becoming immobilized on the plate. In some embodiments the incubation step includes the addition of labeled glypican-1 protein of known concentrations. In some embodiments the amount of glypican-1 in the body fluid or tissue sample is detected as a diminishing binding of the mixed labeled glypican-1 protein. In other embodiments the ELISA is a sandwich ELISA.

At this stage, the pH of the incubation mixture will ordinarily be in the range of about 4-9.5. In other embodiments the pH range will be about 6-9. In yet another embodiment the pH range will be about 7-8. In another embodiment the pH of the assay (ELISA) diluent is pH 7.4. The pH of the incubation buffer is chosen to maintain a significant level of specific binding of the capture reagent to the glypican-1 being captured. Various buffers may be employed to achieve and maintain the desired pH during this step, including borate, phosphate, carbonate, Tris-HCl or Tris-phosphate, acetate, barbital, and the like. The particular buffer employed is not critical to the invention, but in individual assays one buffer may be preferred over another.

In some embodiments, the biological sample is separated (preferably by washing) from the immobilized capture reagent to remove uncaptured molecules. The solution used for washing is generally a buffer ("washing buffer") with a pH determined using the considerations and buffers described above for the incubation step. In one embodiment, the pH range of the washing buffer is about 6-9. The washing may be done one or more times. The temperature of washing is generally from refrigerator to moderate temperatures, with a constant temperature maintained during the assay period, typically from about 0-40° C. In other embodiments the washing temperature is about 4-30° C. For example, the wash buffer can be placed in ice at 4° C. in a reservoir before the washing, and a plate washer can be utilized for this step. A cross-linking agent or other suitable agent may also be added at this stage to allow the now-bound glypican-1 to be covalently attached to the capture reagent if there is any concern that the captured glypican-1 may dissociate to some extent in the subsequent steps.

In some embodiments, the immobilized capture reagent is contacted with detectable antibodies. In some embodiments the detectable antibodies are anti-glypican-1 antibodies. In some embodiments the anti-glypican-1 antibody is MIL-38. In other embodiments, the antibodies are those described in table 2. In other embodiments the detectable antibodies are any antibody capable of detecting glypican-1. The detectable antibody is contacted with the immobilized glypican-1 at a temperature of about 20-40° C. In other embodiments the detectable antibody is contacted at about 20-25° C., with the exact temperature and time for contacting the two being dependent primarily on the detection means employed. For example, when strepatavidin-peroxidase and 3,3',5,5'-tetramethyl benzidine are used as the means for detection, e.g., in one embodiment, the contacting is carried out (e.g., about 1 hour or more) to amplify the signal to the maximum. In some embodiments, a molar excess of an antibody or ligand with respect to the maximum concentration of expected free glypican-1 is added to the plate after it is washed. This antibody is directly or indirectly detectable. The detectable antibody may be a polyclonal or monoclonal antibody, e.g., in certain embodiments, it is a monoclonal antibody, in one embodiment murine, and in one embodiment MIL-38. Also, the detectable antibody can be directly detectable, and in one embodiment has a colorimetric label, and in another embodiment has a flurometric label. In other embodiments the detectable antibody is biotinylated and the detection means is avidin or streptavidin-peroxidase and 3,3',5,5'-tetramethyl benzidine. In some embodiments the detectable antibody may be labeled with a biotin-avidin amplification system, a chemiluminescence system, microspheres, or colloidal gold. The readout of the detection means can be fluorimetric or colorimetric among others. The affinity of the antibody must be sufficiently high that small amounts of the free glypican-1 can be detected.

In some embodiments, the glypican-1 that is bound to the capture reagent is measured using a detection means for the detectable antibody. If the body fluid or tissue sample is from patient, the measuring step comprises comparing the reaction that occurs as a result of the above steps with a standard curve to determine the level of glypican-1 in said body fluid or tissue sample. In other embodiments the reaction that occurs as a result of the above steps is compared to a similar reaction using a control body fluid or tissue sample such as the body fluid or tissue of a age-matched cancer-free individual.

In other glypican-1 detection embodiments, the glypican-1 in the body fluid of patients is detected via a Western Blot Analysis. In some embodiments this assay separates the proteins in a complex sample using electrophoresis. In other embodiments the electrophoresis separation is performed in a size exclusion gel such as a sodium dodecyl sulfate polyacrylamide gel (commonly known as SDS-PAGE). In one embodiment the separated proteins are then transferred to a membrane. One skilled in the art will recognize that there are a variety of materials that can be used for westerns. In some embodiments the membrane is made from nitrocellulose or polyvinylidene fluoride, PVDF. In some embodiments the transfer occurs in a protein transfer box such that the proteins retain the same separation pattern on the membrane as they had in the gel. In some embodiments the membrane is then incubated in diluted protein solutions, e.g. non-fat dry milk or bovine serum albumin (BSA), to block the non-specific binding sites. The blocked membrane can then be incubated with a primary antibody that is specific for the glypican-1 target protein. In some embodiments the membrane is then washed and incubated with a secondary antibody that targets the first antibody. In some embodiments the first or the second antibody is conjugated to a detectable label such that it can be easily detected. In some embodiments the label includes a fluorescent label, a chemiluminescent label, a radiolabel, or another label well known in the art. In some embodiments, said labels conjugated to the secondary ligand are chosen from a group consisting of a radiolabel, a fluorescent label, a biotin-avidin amplification system, a chemiluminescence system, microspheres, and colloidal gold.

Optionally, some aspects of the invention teach that once a user has determined whether a target protein is present in the sample, the primary and (optional) secondary antibodies can be stripped from the membrane, and the membrane can be incubated with an alternative primary antibody that is specific for the same or another protein. In some embodiments the second protein may be used as a loading control. In other embodiments the second protein is another marker for patient health.

In one embodiment, glypican-1 is detected via flow cytometry. In some embodiments glypican-1 is detected on the cell surface of cells in patient body fluids or tissues. In certain aspects of the invention the detection of glypican-1 for flow cytometry may be conducted as outlined below. In some embodiments, cells from body fluids or tissues are purified. The purification of the cells can include a neutralization step. In some embodiments the neutralization step comprises storing the cells in neutralization buffer. The neutralization buffer can be made by combining 39 ml of 0.2 M $NaH_2PO_4$ to 61 ml of 0.2M $Na_2HPO_4$ and adding water to 200 ml. In some embodiments, the cells are centrifuged and resuspended in different solutions. In other embodiments, the cells are sorted without purification. In some embodiments the cells are resuspended or washed in CytoLyt solution. In other embodiments the cells are resuspended or washed in phosphate buffered saline (PBS). In some embodiments the cell suspension is treated with ammonium chloride to lyse the red blood cells. In some embodiments the cells are fixed onto slides. In other embodiments the cells remain free. In some embodiments, cells are contacted with a primarily anti-glypican-1 antibody or other ligand. In some embodiments the primary antibody is MIL-38. In some embodiments the primary antibody is not MIL-38. In other embodiments the primary antibody is any other anti-glypican-1 antibody (Table 2). In certain embodiments, the cells are further contacted with a second detection antibody conjugated to a detection label. In alternative embodiments, the antigen may be detected directly by the primary antibody if the primary antibody is conjugated to a detection label. In particular cases, in addition to being labeled with the glypican-1 antibody, the cells may be distinguishably labeled with other probes, including, but not limited to, antibodies to cell surface markers that distinguish one cell type from another. In some aspects the other probes may be used to normalize signals or total cell counts. In some embodiments the other probes label intracellular antigens. In other embodiments the other probes label extracellular antigens. Once labeled, the labeled cells may be isolated by FACS flow cytometry. In some embodiments, the FACS machine may isolate labeled cells singly (i.e., as single cells). In other embodiments, the labeled cells may be isolated as a mixed population, and then diluted into single cells after FACS. In some embodiments the second label can be a dye. In some embodiments the dye label is DAPI. In some embodiments DAPI labeling is used to quantify the number of cells in the sample.

In embodiments in which the cell is labeled with a plurality of different labels, the cells may be selected using a plurality of different properties. For example, cells may first be sorted by one probe and then another. In some embodiments cells can first be sorted by cell type and later be sorted by glypican-1 concentration. Similarly cells may be sorted in any sequence as designed together with the probes and the detection of the FACS machine. The general principles of fluorescence activated cell sorting, including methods by which single cell suspensions can be made, methods by which cells can be labeled using, e.g., fluorescently labeled probes, methods by which cells can be separated from one another, as well as hardware that can be employed in flow cytometry, including flow cells, reagents, and computer control systems are known and are reviewed in a variety of publications, including, but not limited to: (Orfao et al., 1996; Johnson et al., 2007; Tung et al., 2007; and Dainiak et al., 2007).

The present invention also includes kits for detecting glypican-1 in the body fluids or tissues of patients. In one embodiment the kit for detecting cancer comprises the materials necessary to conduct any of the detection assays described in this application. In some embodiments the kit for detecting cancer comprises a first anti-glypican-1 antibody or other ligand, a pharmaceutically acceptable carrier, and glypican-1 standards; wherein said kit is capable of detecting glypican-1 in the body fluid or tissue of a patient. The first anti-glypican-1 antibody may or may not be MIL-38. The first anti-glypican-1 antibody may comprise: a heavy chain variable region comprising a complementarity determining region 1 (CDR1) comprising or consisting of an amino acid sequence defined by positions 50-54 of SEQ ID NO: 10; a complementarity determining region 2 (CDR2) comprising or consisting of an amino acid sequence defined by positions 69-85 of SEQ ID NO: 10; a complementarity determining region 3 (CDR3) comprising or consisting of an amino acid sequence defined by positions 118-126 of SEQ ID NO: 10; and comprise a light chain variable region comprising a complementarity determining region 1 (CDR1) comprising or consisting of an amino acid sequence defined by positions 44-54 of SEQ ID NO: 11; a complementarity determining region 2 (CDR2) comprising or consisting of an amino acid sequence defined by positions 70-76 of SEQ ID NO: 11; a complementarity determining region 3 (CDR3) comprising or consisting of an amino acid sequence defined by positions 109-117 of SEQ ID NO: 11. The anti-glypican-1 antibody used to detect the glypican-1 levels may not comprise: a light chain variable region comprising a complementarity determining region 1 (CDR1) comprising or consisting of an amino acid sequence defined by positions 48-58 of SEQ ID NO: 12; a complementarity determining region 2 (CDR2) comprising or consisting of an amino acid sequence defined by positions 74-80 of SEQ ID NO: 12; and a complementarity determining region 3 (CDR3) comprising or consisting of an amino acid sequence defined by positions 113-121 of SEQ ID NO: 12. The first anti-glypican-1 antibody may be produced by or otherwise identical to an antibody generated by hybridoma cells as deposited on 22 Aug. 2014 at CellBank Australia (CBA) under accession number CBA20140026.

In some embodiments, the kit will require the additional use of standard laboratory tools or machinery. In some embodiments, necessary tools include pipettes, cell sorting machines, plate readers, centrifuges etc as are known to those being skilled in the art. In some embodiments, use of the kit may require additional standard laboratory reagents such as pipette tips, membranes, buffers, or chemicals as are well known by those being skilled in the art. In some embodiments the kit further comprises a secondary ligand. In some embodiments the secondary ligand is a second anti-glypican-1 antibody. In one embodiment, the second anti-glypican antibody is the same as the first anti-glypican-1 antibody. In some embodiments, the secondary ligand is conjugated to a label for rapid detection of said ligand. In some embodiments the antibodies of the kit can be antibody fragments or antibody combinations as described in this application.

In some embodiments the detection of glypican-1 in the body fluids or tissues of a patient is indicative of the presence of prostate cancer. In some embodiments, the presence of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 600, 700, 800, 900, 1000 pg/ml of glypican-1 in the body fluid of a patient is indicative of prostate cancer.

In some embodiments the detection of glypican-1 in the body fluids or tissues of a patient is indicative of the presence of prostate cancer. In some embodiments, the presence of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 600, 700, 800, 900, 1000 ng/ml of glypican-1 in the body fluid of a patient is indicative of prostate cancer.

In some embodiments the detection of glypican-1 in the body fluids or tissues of a patient is indicative of the presence of prostate cancer. In some embodiments, the presence of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 µg/ml of glypican-1 in the body fluid or tissue of a patient is indicative of prostate cancer.

In some embodiments elevated levels of glypican-1, or glypican-1 detection signal in the body fluid or tissue of a patient is indicative of prostate cancer. In some cases, the glypican-1 levels of cancer patients are 1%, 2%, 3%, 4, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 110%, 120%, 130%, 140%, 150%, 160%, 170%, 180%, 190%, 200%, 210%, 220%, 230%, 240%, 250%, 260%, 270%, 280%, 290%, 300%, 310%, 320%, 330%, 340%, 350%, 360%, 370%, 380%, 390%, 400%, 410%, 420%, 430%, 440%, 450%, 460%, 470%, 480%, 490%, 500, 600%, 700%, 800%, 900%, 1000%, 5,000%, 10,000%, >15,000% higher than the glypican-1 levels or glypican-1 detection signal of a control non-cancerous body fluid or tissue. In some embodiments the control non-cancerous body fluid or tissue will be age matched to the patient.

EXAMPLES

Example 1. Characterization of the Cell Bound MIL-38 Antigen

Despite initial reports of the MIL-38 antigen as a 30 kD protein (Russell et al 2004), work by the present inventors has indicated that the MIL-38 antibody predominantly detects a 60 kDa antigen in a range of cell extracts. Western blot reactivity of MIL-38 with the antigen is lost if the sample has been incubated with reducing agents prior to gel electrophoresis.

Using MIL-38 antibody for immunoprecipitation experiments we were able to specifically isolate the 60 kDa protein from a variety of cell extracts. The presence of the 60 kDa antigen on the cell surface was investigated using live cell immunoprecipitations. In these experiments, live cells were incubated on ice with serum-free media containing the MIL-38 antibody. Cells were then washed, lysates prepared and incubated with protein G beads to isolate any antibody associated with the cells. The 60 kDa band was present in these immunoprecipitates indicating that the antigen was recognized on the cell surface by the MIL-38 in the media.

Example 2. MIL-38 Antigen Immunoprecipitation and Mass Spectrometry

DU-145 prostate cancer cells were processed through a membrane protein extraction kit (MPEK). Membrane extracts were immunoprecipitated with MIL-38 cross-linked to magnetic beads. The immunoprecipitates were either run into a gel and excised for mass spectrometry analysis or were eluted directly from the beads and then subjected to mass spectrometry. Antigens bound to the MIL-38 antibody were then analyzed via mass spectrometry analysis, which can identify peptides based on mass/charge data.

The mass spectrometer identified glypican-1 with a peptide score of 4278 and sequence coverage of 46% including 18 distinct sequences (FIG. 1).

Figure 2:
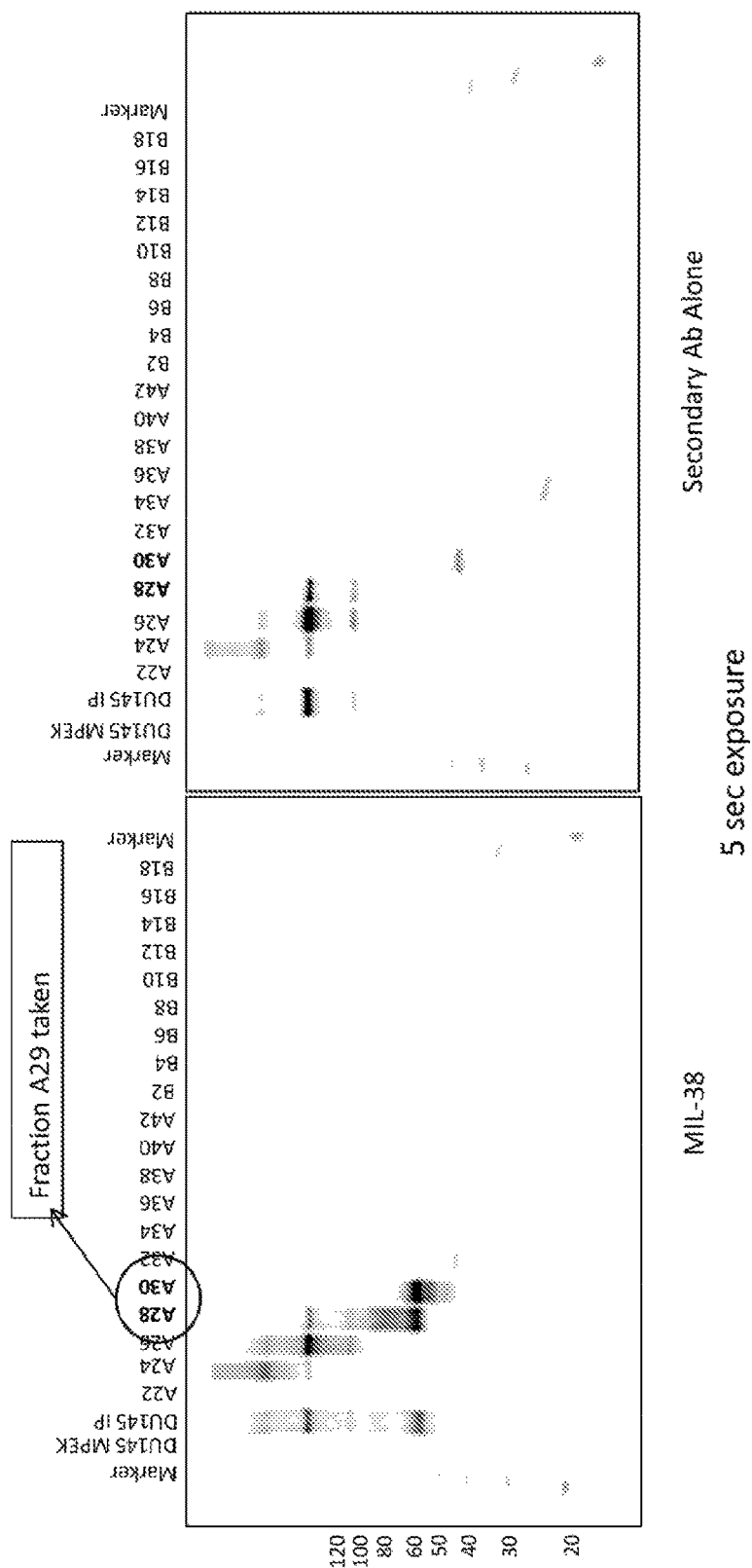
FIG. 2. MIL-38 immunoprecipitation and size-exclusion chromatography.
DU-145 prostate cancer cell membrane extracts were immunoprecipitated using MIL-38 and run through a size-exclusion chromatography column. The figure shows western blot analyses of even numbered chromatography fractions using either MIL-38 antibody or secondary antibody control. The MIL-38 antigen is shown at 60 Kd in fractions A28 and A30.

Example 3. MIL-38 Antigen Immunoprecipitation, Size Exclusion Chromatography and Mass Spectrometry DU-145 prostate cancer cells were processed through a membrane protein extraction kit (MPEK). Membrane extracts were immunoprecipitated with MIL-38 cross-linked to magnetic beads. Following extensive washing, the immunoprecipitate was eluted in TBS (tris buffered saline) containing 2% SDS. The eluate was subjected to size exclusion chromatography (SEC) and every second fraction was acetone precipitated, resuspended in sample loading buffer and used for MIL-38 western blots. Fractions 28 and 30 contained high amounts of MIL-38 antigen (FIG. 2), indicating that fraction 29 would also contain high concentrations of the MIL-38 antigen. Fraction 29 was subjected to mass spec analysis and glypican-1 was identified with sequence coverage of 14% (FIG. 3). This further confirmed that the antigen for the MIL-38 antibody was glypican-1.

Example 4. MIL-38 and Anti-Glypican-1 (Anti-GPC-1) Antibodies Show Overlapping Reactivity on 2D Western Blots A rabbit anti-GPC-1 antibody was purchased and showed reactivity with the glypican-1 core protein at a molecular weight of approximately 60 kDa—the same molecular weight as detected by MIL-38. To confirm that MIL-38 recognized glypican-1, prostate cancer DU-145 MPEK extracts were subjected to 2D electrophoresis and western blotting.

As shown in FIG. 4, MIL-38 antibody and the anti-GPC-1 antibodies showed overlapping reactivity detecting a protein with 60 kDa molecular weight and isoelectric points ranging from 5 to 7.

Example 5. MIL-38 is Detected in Anti-GPC-1 Immunoprecipitates and Vice Versa

MIL-38 or rabbit anti-GPC-1 antibodies were used to immunoprecipitate their respective antigens from DU-145 or C3 (MIL-38 negative) MPEK extracts. The immunoprecipitates (IPs) were western blotted with either MIL-38 or anti-GPC-1 antibody (FIG. 5).

A 60 kDa GPC-1 reactive band was detected in MIL-38 IPs blotted with anti-GPC-1, while a 60 kDa MIL-38 reactive band was detected in anti-GPC-1 IPs blotted with MIL-38. No reactivity was detected with the secondary only controls. Furthermore, immunoprecipitating with MIL-38 antibody resulted in almost complete depletion of both MIL-38 and anti-GPC-1 antigens, strongly suggesting that the MIL-38 antigen is glypican-1.

Example 6. MIL-38 Detects Recombinant GPC-1

Two sources of purified recombinant glypican-1 were tested or reactivity with MIL-38 and anti-GPC-1 antibodies. The first source was a truncated form produced from wheat germ extracts (note this would not contain appropriate mammalian post-translational modifications). The second source was full-length glypican-1 produced in murine NS0 cells. No MIL-38 reactivity was observed with the wheat germ expressed glypican-1, however it could be detected with the rabbit anti-GPC-1 antibody (data not shown). In contrast, very strong reactivity with MIL-38 and anti-GPC-1 antibodies was observed for the glypican-1 produced in NS0 cells (FIG. 6).

Example 7. MIL-38 can Detect Antigen Secreted into Cell Culture Supernatant

To date, there has been no experimental evidence for secretion of MIL-38 antigen. To test this, DU-145 cells were washed in serum-free media then incubated with serum-free media for 36 hrs. The resulting conditioned media was immunoprecipitated with MIL-38 and the resulting samples compared with a standard IP from DU-145 MPEK extracts. Bands of approximately 40 and 55 kDa were observed in the conditioned medium IP, compared to the 60 kDa band isolated from DU-145 extracts (FIG. 7).

The conditioned medium IP sample containing the 40 and 55 kD bands was subjected to mass spec analysis. Glypican-1 (SEQ ID No: 2) was identified with 16% peptide coverage (FIG. 8a). Separate analyses of just the 40 kD band (FIG. 8b) or the 55 kD band (FIG. 8c) both identified as the glypican-1 peptide (SEQ ID No: 2).

These results suggest that a MIL-38 reactive form of glypican-1 can be released into cell culture supernatant from the DU-145 prostate cancer cell line.

Example 8. GPC-1 can be Detected by MIL-38 in Prostate Cancer Plasma Samples and in Membrane Extracts from Prostate Cancer Patients To date, there has been no experimental evidence for secretion of MIL-38 antigen in plasma samples from normal or prostate cancer patients. To test this, plasma samples from one normal patient (042) and one prostate cancer patient (046) were immunoprecipitated with MIL-38 antibody and the IP sample western blotted with MIL-38 and anti-GPC-1 antibodies (FIG. 9a).

Both antibodies detected specific bands of approx. 70 kDa in both plasma samples. The signals were markedly higher (darker bands) for both MIL-38 and anti-GPC-1 antibodies in the prostate cancer patient plasma compared to the normal patient plasma, suggesting that this soluble form of glypican-1 may be elevated in prostate cancer patients.

To determine if MIL-38 antigen could be detected in membrane protein extracts from normal prostate and prostate cancer, one sample of each was obtained from Novus Bio. Equivalent amounts of protein were western blotted using MIL-38 antibody (FIG. 9b). The prostate cancer extract demonstrated much higher expression of the MIL-38 antigen than the normal prostate sample.

Example 9. Detection of MIL-38 Antigen in Patient Urine

MIL-38 can detect cells in the urine of prostate cancer patients. To test the sensitivity and specificity of this detection method, 125 age-matched urine samples were obtained. Cells were spun down from the urine and analyzed by the MIL-38 indirect immunofluorescence assay. A total of 47 healthy controls, 37 benign prostatic hypertrophy (BPH) and 41 biopsy-confirmed prostate cancers were analyzed. Examples of positive prostate cancer cells, DU-145 positive controls and C3 negative cells are shown (FIG. 10).

The MIL-38 immunofluorescence assay (IFA) test demonstrated a sensitivity of 71% and a specificity of 73% in identifying prostate cancers within the cohort. The test showed 71% sensitivity and 76% specificity in identifying prostate cancers compared to BPH patients. (Table 3).

TABLE 3

Sensitivity and specificity calculations of prostate cancer detection in patient urine.

Sensitivity and Specificity Calculations

| True Positive | False Positive |
|---|---|
| 29 | 12 |
| False Negative | True Negative |
| 23 | 61 |

Sensitivity and Specificity Calculations for BPH only

| True Positive | False Positive |
|---|---|
| 29 | 12 |
| False Negative | True Negative |
| 9 | 28 |

Example 10. Combination of MIL-38 Antigen Detection with PSA Level Increases Ability to Detect Prostate Cancer When the MIL-38 immunofluorescence assay (IFA) test is combined with the PSA test there are increases in sensitivity and specificity. These increases vary according to the cut-off value applied to the PSA test. When the cutoff for a positive diagnosis is greater than 2 ng/mL then specificity increases from 73% for just the IFA test to 83% for the two tests combined. When the cutoff for a positive diagnosis is greater than 4 ng/mL then specificity increases from 73% for just the IFA test to 89% for the two tests combined.

This is further illustrated by the logistic regression analysis which shows increases in OR and 95% CI when the two tests are combined.

TABLE 4

Increases in sensitivity and specificity when the MIL-38 IFA test is combined with PSA scores Stratified by 2 ng/ml PSA < 2 ng/ml Cancer

| | | 1 | 0 | |
|---|---|---|---|---|
| GPC-1 | 1 | 5 | 17 | Sensitivity = 100% |
| IFA | 0 | 0 | 36 | Specificity = 68% |

PSA ≥ 2 ng/ml

Cancer

| | | 1 | 0 | |
|---|---|---|---|---|
| GPC-1 | 1 | 24 | 4 | Sensitivity = 67% |
| IFA | 0 | 12 | 20 | Specificity = 83% |

Stratified by 4 ng/ml

PSA < 4 ng/ml

Cancer

| | | 1 | 0 | |
|---|---|---|---|---|
| GPC-1 | 1 | 10 | 20 | Sensitivity = 77% |
| IFA | 0 | 3 | 48 | Specificity = 71% |

PSA ≥ 4 ng/ml

Cancer

| | | 1 | 0 | |
|---|---|---|---|---|
| GPC-1 | 1 | 19 | 1 | Sensitivity = 68% |
| IFA | 0 | 9 | 8 | Specificity = 89% |

Logistic regression

| | OR | 95% CI |
|---|---|---|
| GPC-1 IFA | 6.4 | 2.8-14.9 |
| GPC-1 IFA (adjusted for PSA <4) | 10.2 | 3.2-32.8 |
| GPC-1 IFA (adjusted for PSA <2) | 13.4 | 4.0-44.7 |

Example 11. MIL-38 can Detect Recombinant Glypican-1 in a Variety of ELISA Formats Three ELISA assay formats were conducted as shown in FIG. 11. Recombinant glypican-1 was tested at 0, 0.1, 1 and 10 ng/ml concentrations using MIL-38 as a capture antibody and rabbit anti-GPC-1 as a detection antibody. Similar experiments were conducted using the rabbit anti-GPC-1 as the capture antibody and the MIL-38 as the detection antibody. A single antibody ELISA was also tested using the MIL-38 antibody as the capture antibody, and a biotinylated MIL-38 antibody as the detection antibody. The results indicate that anti-GPC antibodies can be used in a variety of ELISA formats and that the NS0 GPC-1 might represent a suitable positive control.

Example 12. Detection of Glypican-1 Antigen Using AM4 MIL-38 Antibodies

Experiments performed by the present inventors determined that an original deposit of the hybridoma for MIL-38 antibody (ATCC accession no. HB11785: murine hybridoma BLCA-38), then referred to as the "BLCA-38 hybridoma" is a mixed population of hybridoma cells that produces two distinct antibody populations, referred to here as "AM3" and "AM4". Hybridoma cells responsible for producing each different antibody population were separated, and the "AM4" hybridoma cells were deposited on 22 Aug. 2014 at CellBank Australia (CBA), 214 Hawkesbury Rd. Westmead NSW 2145, Australia, under accession number CBA20140026.

Ninety-six well plates were coated with MIL-38 preps AM3 or AM4 (1 µg/well) in carbonate buffer pH 9.5 overnight. Plates were blocked with PBS-Tween (0.1%) containing 5% skim milk at 37° C. and washed. Antigen (GPC-1 NS0) was diluted in Buffer II (20 mM HEPES pH 7.5, 0.5 mM EDTA, 0.5% Triton X-100) with the addition of 150 mM NaCl and incubated overnight at 37° C. Detection was performed with biotinylated AM4 antibody followed by detection with avidin HRP (1 µg/mL). TMB (Sigma cat no T0440) was added and stopped with TMB stop solution (Sigma S5814). Absorbance was read at 450 nm. Results are shown in FIG. 12A.

In a second experiment, ninety-six well plates were coated with MIL-38 preps 34A (a mixture of AM3 and AM4 antibodies) or AM4 (2.5 µg/well) in PBS pH 7.2 for 1 h at room temperature. Plates were blocked with Blocker Casein (Thermo) in PBS-Tween (0.05%) for 1 h at 37° C. Following washing, antigen (GPC-1 NS0) was diluted in TBS pH 7.2 containing 50 mM Tricine and 150 mM NaCl and incubated at 37° C. for 1 h. Detection was performed with biotinylated AM4 clone 1F5 followed by detection with avidin HRP (1 µg/mL). TMB (Sigma cat no T0440) was added and stopped with TMB stop solution (Sigma S5814). Absorbance was read 450 nm. Results are shown in FIG. 12B.

The first ELISA described above was developed using MIL-38 to capture NS0 produced GPC-1 (i.e. MIL-38 antigen). This experiment compared monoclonal AM3 MIL-38 and monoclonal AM4 MIL-38 for capture. AM3 did not function as a capture agent in a sandwich ELISA assay, whereas AM4 was shown to do so (FIG. 12A).

The second ELISA described above compared the ELISA signal obtained when a mixed population of MIL-38 (AM3 and AM4) was compared to that obtained from a monoclonal AM4 1F5 clone. Using AM4 IFS as a capture agent provided a higher ELISA signal than using the mixed 34A antibody population (FIG. 12B).

The sandwich ELISA results demonstrate that only the AM4-like forms of the monoclonal MIL-38 antibody have utility in detecting glypican-1 antigen as a capture reagent and that a capture agent containing a monoclonal population provides a superior ELISA signal to that consisting of a mixed population.

Example 13 Sequence Analysis of AM4 and AM3 MIL-38 Antibody Populations

Materials and Methods

Heavy and Light Chain Sequencing (DNA)

Three separate sequencing runs were performed. The first run (coded 224945) utilised bi-clonal hybridoma cells from a mixed (AM4 and AM3) preparation named 1-0. The second run (coded 449295-1) utilised cells from Alfio I a hybridoma stock that was used to generate AM4. The third run (coded 449295-5) utilised cells from Alfio II, a hybridoma stock that was used to generate AM3.

For sequencing runs 224945 (1-0) and 449295-1 (Alfio I), total RNA was extracted from frozen hybridoma cells and cDNA was synthesized from the RNA. RT-PCR was then performed to amplify the variable regions (heavy and light chains) and constant regions of the antibody, which were then cloned into a standard cloning vector separately and sequenced.

Total RNA was isolated from the hybridoma cells following the technical manual of TRIzol® Plus RNA Purification System. The total RNA was analysed by agarose gel electrophoresis. Total RNA was reverse transcribed into cDNA using isotype-specific anti-sense primers or universal primers following the technical manual of SuperScript™ III First-Strand Synthesis System. The antibody fragments of VH, VL, CH and CL were amplified according to the standard operating procedure of RACE of GenScript.

Amplified antibody fragments were separately cloned into a standard cloning vector using standard molecular cloning procedures.

Colony PCR screening was performed to identify clones with inserts of correct sizes. No less than five single colonies with inserts of correct sizes were sequenced for each antibody fragment.

$V_H$ and $V_L$ plasmids encoded the full-length variable regions of the antibody and a part of $C_H1$ and $C_L$. $C_H$ plasmid encoded a part of $C_H1$ and full-length $C_H2$ and $C_H3$. $C_L$ plasmid encoded a part of $C_L$. In order to get full-length constant regions or heavy/light chain, the part of constant regions encoded by $V_H$ and $V_L$ plasmids and the part of constant regions encoded by $C_H$ and $C_L$ plasmids were amplified by PCR separately, and then overlap extension PCR was employed to obtain full-length DNAs. Five single colonies with correct $V_H$, $V_L$, $C_H$ and $C_L$ insert sizes were sent for sequencing.

Sequencing run 449295-5 (Alfio II) encountered difficulty obtaining sequence corresponding to the expected IgG1 heavy chain sequence. Two RNA preparations were performed. For the 1st batch of cells, oligo-dT primer and CDS III primers were used for reverse transcription (RT). VH/CH and VK/CK were amplified by PCR using IgG1 and IgK specific primers, partial mouse β-actin gene was amplified as positive control. Normal light chain bands were obtained easily while only weak VH could be observed on the gel. Five individual colonies with correct VK and CK insert sizes were sent for sequencing. The VK and CK genes of five different clones were found to be nearly identical. The consensus light chain sequences from the Alfio II hybridoma is listed below. One unproductive heavy chain sequence was obtained from eight randomly sequenced VH positive clones, shown as below. Three kinds of heavy chain constant region sequences were obtained from ten randomly sequenced CH positive clones (one $IgG_1CH$, one $IgG_{2a}C_H$ and eight $IgG_{2b}C_H$). In order to avoid the influence of potential class switching, amplification of the CH using IgM specific primer was performed, but no target PCR product was obtained. There was also no target PCR product when full-length heavy chain ($V_H$-$C_H$) was amplified using heavy chain FRI degenerate primers.

As no productive heavy chain could be obtained after several attempts, isolation of heavy chain sequence from the 2nd vial of Alfio II cells was attempted. For the 2nd vial of cells, oligo-dT primer was used for reverse transcription initially. $V_H$ was amplified using IgG1, IgG2b, IgM, IgA specific primers and IgG degenerate primer, respectively, and VK was amplified using IgK specific primers. Productive light chain and unproductive heavy chain, which were identical with previous results, were obtained. Reverse transcription using Random 6 mers primer was also attempted without success.

In summary, multiple attempts to isolate light chain and heavy chain sequence were made. One rearranged light chain sequence was consistently obtained after different attempts on two batches of cells. However, only weak VH target PCR products were observed and sequencing did not result in any consistent heavy chain sequence.

Results

Sequence Summary Table

Table 5 below provides an overview of heavy and light chain nucleic acid and protein sequences of the antibodies studied, indicating the positions of various internal regions.

TABLE 5

Overview of AM4 and AM3 antibody sequences and internal regions

| DNA Seq ID# |  |  | Leader | HFR1 | HCDR1 | HFR2 | HCDR2 | HFR3 | HCDR3 | HFR4 | CH1-CH3 | Hinge |
|---|---|---|---|---|---|---|---|---|---|---|---|---|
| 13 | AM4 Heavy |  | 1-57 | 58-147 | 148-162 | 163-204 | 205-255 | 256-351 | 352-378 | 379-411 | 412-1383 | 703-741 |
|  |  |  | Leader | LFR1 | LCDR1 | LFR2 | LCDR2 | LFR3 | LCDR3 | LFR4 | CL |  |
| 14 | AM4 Light |  | 1-60 | 61-129 | 130-162 | 163-207 | 208-228 | 229-324 | 325-351 | 352-381 | 382-702 |  |
| 15 | AM3 light |  | 1-72 | 73-141 | 142-174 | 175-219 | 220-240 | 241-336 | 337-363 | 364-393 | 394-714 |  |
| AA Seq ID# |  |  | Leader | HFR1 | HCDR1 | HFR2 | HCDR2 | HFR3 | HCDR3 | HFR4 | CH | Hinge |
| 10 | AM4 heavy |  | 1-19 | 20-49 | 50-54 | 55-68 | 69-85 | 86-117 | 118-126 | 127-137 | 138-461 | 235-247 |
|  |  |  | Leader | LFR1 | LCDR1 | LFR2 | LCDR2 | LFR3 | LCDR3 | LFR4 | CL |  |
| 11 | AM4 light |  | 1-20 | 21-43 | 44-54 | 55-69 | 70-76 | 77-108 | 109-117 | 118-127 | 128-234 |  |
| 12 | AM3 light |  | 1-24 | 25-47 | 48-58 | 59-73 | 74-80 | 81-112 | 113-121 | 122-131 | 132-238 |  |

Notes:
HFR = heavy chain framework region;
HCDR = heavy chain complementarily determining region;
CH = heavy chain constant region
LFR = light chain framework region;
LCDR = light chain complementarily determining region;
CL = light chain constant region
Grey Boxes are indicative of positions within sequence defined in column I by SEQ ID NO.

Sequencing (DNA)

The isolated total RNA of the sample was run alongside a DNA marker (Marker III—TIANGEN, Cat. No.: MD103) on a 1.5% agarose/GelRed™ gel.

Four microliters of PCR products of each sample were run alongside the DNA marker (Marker III) on a 1.5% agarose/GelRed™ gel. The PCR products were purified and stored at −20° C. until further use.

The $V_H$, $V_L$, $C_H$ and $C_L$ genes of five different clones were nearly identical. The consensus sequence, listed below, was determined to be the sequence of the antibody produced by the monoclonal hybridoma population (AM-4).

AM4 MIL-38 Mouse IgG₁ Heavy Chain DNA Consensus Sequence (SEQ ID NO: 13)

ATGGCTTGGGTGTGGACCTTGCTATTCCTGATGGCTGCTGCCCAAAGTATCCAAGCACAGATCAGTTGGTGCAG

TCTGGACCTGAGCTGAAGAAGCCTGGAGAGACAGTCAAGATCTCCTGCAAGGCTTCTGGTTATGCCTTCACAGAC

TATTCAATGAACTGGGTGAAGCAGGCTCCAGGAAAGGGTTTAAGGTGGATGGGCTGGATAAACACTGAGACTGG

TGAGCCAACATATACAGATGACTTCAAGGGACGGTTTGCCTTCTCTTTGGAAACCTCTGCCAGCACTGCCTTTTT

GCAGATCAACAACCTCAGAAATGAAGACACGGCTACATATTTCTGTGCTAGACACTATGATTACGGGGGTTTCC

TTACTGGGGCCAAGGGACTCTGGTCACTGTCTCTGCAGCCAAAACGACACCCCATCTGTCTATCCACTGGCCC

CTGGATCTGCTGCCCAAACTAACTCCATGGTGACCCTGGGATGCCTGGTCAAGGGCTATTTCCCTGAGCCAGTGA

CAGTGACCTGGAACTCTGGATCCCTGTCCAGCGGTGTGCACACCTTCCCAGCTGTCCTGCAGTCTGACCTCTACA

CTCTGAGCAGCTCAGTGACTGTCCCCTCCAGCACCTGGCCCAGCGAGACCGTCACCTGCAACGTTGCCCACCCGG

CCAGCAGCACCAAGGTGGACAAGAAAATTGTGCCCAGGGATTGTGGTTGTAAGCCTTGCATATGTACAGTCCCAG

AAGTATCATCTGTCTTCATCTTCCCCCCAAAGCCCAAGGATGTGCTCACCATTACTCTGACTCCTAAGGTCACGT

GTGTTGTGGTAGACATCAGCAAGGATGATCCCGAGGTCCAGTTCAGCTGGTTTGTAGATGATGTGGAGGTGCACA

CAGCTCAGACGCAACCCCGGGAGGAGCAGTTCAACAGCACTTTCCGCTCAGTCAGTGAACTTCCCATCATGCACC

AGGACTGGCTCAATGGCAAGGAGTTCAAATGCAGGGTCAACAGTGCAGCTTTCCCTGCCCCATCGAGAAAACCA

TCTCCAAAACCAAAGGCAGACCGAAGGCTCCACAGGTGTACACCATTCCACCTCCCAAGGAGCAGATGGCCAAGG

ATAAAGTCAGTCTGACCTGCATGATAACAGACTTCTTCCCTGAAGACATTACTGTGGAGTGGCAGTGGAATGGGC

AGCCAGCGGAGAACTACAAGAACACTCAGCCCATCATGGACACAGATGGCTCTTACTTCGTCTACAGCAAGCTCA

ATGTGCAGAAGAGCAACTGGGAGGCAGGAAATACTTTCACCTGCTCTGTGTTACATGAGGGCCTGCACAACCACC

ATACTGAGAAGAGCCTCTCCCACTCTCCTGGTAAATGA

Individual regions of mouse heavy chain encoded sequence are highlighted with alternating boxed-unboxed text. Positions: 1-57 = leader sequence; 58-147 = framework region (HFR1); 148-162 = complementarity determining region (HCDR1); 163-204 = HFR2; 205-255 = HCDR2; 256-351 = HFR3; 352-378 = HCDR3; 379-411 = HFR4; 412-1383 = constant regions (CH1-CH3); 703-741 = hinge region (double underlined); 1384-1386 = stop codon.

AM4 MIL-38 Mouse Kappa Light Chain DNA Consensus Sequence
(SEQ ID NO: 14)

ATGAGTGTGCTCACTCAGGTCCTGGCGTTGCTGCTGCTGTGCTTACAGGTGCCAGATGT GACATCCAGATGACT
CAGTCTCCAGCCTCCCTATCTGCATCTGTGGGAGAAACTGTCACCATCACATGTCGA GCAAGTGGGAATGTTCAC
AATTATTTAGCA TGGTATCAGCAGAAACAGGGAAAATCTCCTCAACTCCTGGTCTAT ACTGCAAAAACCTTAGC
AGAT GGTGTGCCATCAAGGTTCAGTGGCAGTGGATCAGGAACACAATATTCTCTCAAGATCAATAGCCTGCAGCC
TGAAGATTTTGGGACTTATTACTGT CAACATTTTTGGAGTAATCCGTGGACG TTCGGTGGAGGCACCAAGCTGGA
AATCAAA CGGGCTGATGCTGCACCAACTGTATCCATCTTCCCACCATCCAGTGAGCAGTTAACATCTGGAGGTGC
CTCAGTCGTGTGCTTCTTGAACAACTTCTACCCCAAAGACATCAATGTCAAGTGGAAGATTGATGGCAGTGAACG
ACAAAATGGCGTCCTGAACAGTTGGACTGATCAGGACAGCAAAGACGACACCTACAGCATGAGCAGCACCCTCAC
GTTGACCAAGGACGAGTATGAACGACATAACAGCTATACCTGTGAGGCCACTCACAAGACATCAACTTCACCCAT
TGTCAAGAGCTTCAACAGGAATGAGTGT TAG

Individual regions of mouse light chain encoded sequence are highlighted with
alternating boxed/unboxed text. Positions: 1-60 = leader sequence; 61-129 =
framework region (LFR1); 130-162 = complementarity determining region
(LCDR1); 163-207 = LFR2; 208-228 = LCDR2; 229-324 = LFR3; 325-351 = LCDR3;
352-381 LFR4; 382-702 = constant regions (CK); 703-705 = stop codon.

The heavy and light chain AM4 MIL-38 consensus DNA sequences above translate to the following heavy chain and light chain amino acid sequences:

AM4 MIL-38 Mouse IgG1 Heavy Chain Amino Acid Consensus Sequence
(SEQ ID NO: 10)

MAWVWTLLFLMAAAQSIQA QIQLVQSGPELKKPGETVKISCKASGYAFT DYSMN WVKQAPGKGLRWMG WINTET
GEPTYTDDFKG RFAFSLETSASTAFLQINNLRNEDTATYFCAR HYDYGGFPY WGQGTLVTVSA AKTTPPSVYPL
APGSAAQTNSMVTLGCLVKGYFPEPVTVTWNSGSLSSGVHTFPAVLQSDLYTLSSSVTVPSSTWPSETVTCNVAH
PASSTKVDKKIVPRDCGCKPCICTVPEVSSVFIFPPKPKDVLTITLTPKVTCVVVDISKDDPEVQFSWFVDDVEV
HTAQTQPREEQFNSTFRSVSELPIMHQDWLNGKEFKCRVNSAAFPAPIEKTISKTKGRPKAPQVYTIPPPKEQMA
KDKVSLTCMITDFFPEDITVEWQWNGQPAENYKNTQPIMDTDGSYFVYSKLNVQKSNWEAGNTFTCSVLHEGLHN
HHTEKSLSHSPGK *

Individual regions of mouse IgG1 heavy chain sequence are indicated in the
amino acid sequence above. Positions 1-19 = leader sequence; 20-49 =
framework region (HFR1); 50-54 = complementarity determining region 1
(HCD1); 55-68 = HFR2; 69-85 = HCDR2; 86-117 = HFR3; 118-126 = HCDR3;
127-137 = HFR4 (also called the joining region or J-region); 138-461 =
IgG1 chain constant regions (CH1-CH3) & stop codon (*). Hinge region -
is double underlined in the sequence above.

AM4 consensus MIL-38 Light Chain Amino Acid Consensus Sequence
(SEQ ID NO: 11)

MSVLTQVLALLLLWLTGARC DIQMTQSPASLSASVGETVTITC RASGNVHNYLA WYQQKQGKSPQLLVY TAKTL
AD GVPSRFSGSGSGTQYSLKINSLQPEDFGTYYC QHFWSNPWT FGGGTKLEIK RADAAPTVSIFPPSSEQLTSG
GASVVCFLNNFYPKDINVKWKIDGSERQNGVLNSWTDQDSKDSTYSMSSTLTLTKDEYERHNSYTCEATHKTSTS
PIVKSFNRNEC *

Individual regions of light chain amino acid sequence are indicated as
labelled: Positions 1-20 = Leader sequence; framework region (LFR1); 21-43 =

-continued complementarity determining region 1 (LCDR1); 44-54 = LFR2; 55-69 = LCDR2;
70-76 = LFR3; 77-108 = LCDR3; 109-117 = LFR4; 118-234 = kappa constant region
(CK) & stop codon(*)

AM3 Consensus Sequences

No consistent heavy chain sequence could be obtained from the AM3-like Alfio II cells. The light chain sequence obtained from sequencing run 449295-5 (Alfio II) was consistently obtained and showed clear differences in both the framework regions and the complementarity-determining regions compared to the sequence for the other two sequencing runs.

AM3 MIL-38 Kappa Light Chain DNA Consensus Sequence
(SEQ ID NO: 15)

ATGGGCATCAAGATGGAGTCACAGACTCAGGTCTTTGTATACATGTTGCTGTGGTTGTCTGGTGTTGATGGAGAC

ATTGTGATGACCCAGTCTCAAAAGTTCATGTCCACATCAATAGGAGACAGGGTCAGCGTCACCTGCAAGGCCAGT

CAGAATGTGGGTTCTCATGTAGCCTGGTTTCAGCAGAAACCAGGGCAATCTCCTAAAGCACTGATTTACTCGGC

ATCCTACCGGTACAGCGGAGTCACTGATCGCTTCACAGGCAGTGGATCTGGGACAGATTTCACTCTCACCATCAA

CAATGTGCAGTCTGAAGACTTGGCAGAGTATTTCTGTCAGCAATATAACAGTTTTCCATTCACGTTCGGTTCGGG

GACAAAGTTGGAAATAAAACGGGCTGATGCTGCACCAACTGTATCCATCTTCCCACCATCCAGTGAGCAGTTAAC

ATCTGGAGGTGCCTCAGTCGTGTGCTTCTTGAACAACTTCTACCCCAAAGACATCAATGTCAAGTGGAAGATTGA

TGGCAGTGAACGACAAAATGGCGTCCTGAACAGTTGGACTGATCAGGACAGCAAAGACAGCACCTACAGCATGAG

CAGCACCCTCACGTTGACCAAGGACGAGTATGAACGACATAACAGCTATACCTGTGAGGCCACTCACAAGACATC

AACTTCACCCATTGTCAAGAGCTTCAACAGGAATGAGTGTTAG

* Individual regions of light chain encoded sequence are highlighted with
alternating boxed/unboxed text. Positions: 1-72 = leader sequence; 73-141 =
framework region (LFR1); 142-174 = complementarity determining region
(LCDR1); 175-219 = LFR2; 220-240 = LCDR2; 241-336 = LFR3; 337-363 = LCDR3;
364-393 = LFR4; 394-714 = constant region (CK); 715-717 = stop codon AM3 MIL-38 Light Chain Amino Acid Consensus Sequence
(SEQ ID NO: 12)

MGIKMESQTQVFVYMLLWLSGVDGDIVMTQSQKFMSTSIGDRVSVTCKASQNVGSHVAWFQQKPGQSPKALIYS

ASYRYSGVTDRFTGSGSGTDFTLTINNVQSEDLAEYFCQQYNSFPFTFGSGTKLEIKRADAAPTVSIFPPSSEQ

LTSGGASVVCFLNNFYPKDINVKWKIDGSERQNGVLNSWTDQDSKDSTYSMSSTLTLTKDEYERHNSYTCEATHK

TSTSPIVKSFNREC*

Individual regions of light chain amino acid sequence are indicated as
labelled: Positions 1-24 = Leader sequence; 25-47 = framework region (LFR1);
48-58 = complementarity determining region 1 (LCDR1); 59-73 = LFR2; 74-80 =
LCDR2; 81-112 = LFR3; 113-121 = LCDR3; 122-131 = LFR4; 132-238 = kappa
constant region (CK) & stop codon(*)

Example 14 Identification and Characterisation of Glypican-1 Epitope Bound by AM4 Anti-Glypican-1 Antibodies Materials and Methods Table 6 below provides information on the AM4 anti-glypican-1 antibodies used in this study.

TABLE 6 description of AM4 antibodies used

| Name | Origin | Concentration | Location | Status |
|---|---|---|---|---|
| MIL38-AM4* | mouse | 4.6 mg/ml | −20° C./73 | OK |

*Produced by hybridoma cells as deposited at Cellbank Australia under accession number CBA20140026

Peptides

The human glypican-1 (GPC-1) sequence on which this study was based is defined in SEQ ID NO: 16. The following sequences of residues were used:

```
GPC1_residues #343-366
                                (SEQ ID NO: 17)
GNPKVNPQGPGPEEKRRRGKLAP GPC1_residues #140-149
                                (SEQ ID NO: 18)
GELYTQNARAFRDLYSELR
```

Peptide Synthesis

Peptide synthesis was performed using the methods referred in Example 1. Chemically synthesized linear and CLIPS peptides were synthesized according to the designs shown below:

Chemically Linked Peptides on Scaffolds (CLIPS) Technology

The following provides description of general principles of the CLIPS technology utilised.

CLIPS technology structurally fixes peptides into defined three-dimensional structures. This results in functional mimics of even the most complex binding sites. CLIPS technology is now routinely used to shape peptide libraries into single, double or triple looped structures as well as sheet- and helix-like folds.

The CLIPS reaction takes place between bromo groups of the CLIPS scaffold and thiol sidechains of cysteines. The reaction is fast and specific under mild conditions. Using this chemistry, native protein sequences are transformed into CLIPS constructs with a range of structures including single T2 loops, T3 double loops, conjugated T2+T3 loops, stabilized beta sheets, and stabilized alpha helixes (Timmerman et al., J. Mol. Recognit. 2007; 20: 283-29).

CLIPS library screening starts with the conversion of the target protein into a library of up to 10,000 overlapping peptide constructs, using a combinatorial matrix design. On a solid carrier, a matrix of linear peptides is synthesized, which are subsequently shaped into spatially defined CLIPS constructs. Constructs representing both parts of the discontinuous epitope in the correct conformation bind the antibody with high affinity, which is detected and quantified. Constructs presenting the incomplete epitope bind the antibody with lower affinity, whereas constructs not containing the epitope do not bind at all. Affinity information is used in iterative screens to define the sequence and conformation of epitopes in detail.

The target protein containing a discontinuous conformational epitope is converted into a matrix library. Combinatorial peptides are synthesized on a proprietary minicard and chemically converted into spatially defined CLIPS constructs. Binding of antibodies is quantified.

Peptide Synthesis

To reconstruct discontinuous epitopes of the target molecule a library of structured peptides was synthesized. This was done using Chemically Linked Peptides on Scaffolds (CLIPS) technology. CLIPS technology allowed the generation of structured peptides in single loops, double-loops, triple loops, sheet-like folds, helix-like folds and combinations thereof. CLIPS templates were coupled to cysteine residues. The side-chains of multiple cysteines in the peptides were coupled to one or two CLIPS templates. For example, a 0.5 mM solution of the T2 CLIPS template 1,3-bis (bromomethyl) benzene was dissolved in ammonium bicarbonate (20 mM, pH 7.9)/acetonitrile (1:1(v/v)). This solution was added onto the peptide arrays. The CLIPS template bound to side-chains of two cysteines as present in the solid-phase bound peptides of the peptide-arrays (455 wells plate with 3 µl wells). The peptide arrays were gently shaken in the solution for 30 to 60 minutes while completely covered in solution. Finally, the peptide arrays were washed extensively with excess of $H_2O$ and sonicated in disrupt-buffer containing 1 percent SDS/0.1 percent beta-mercaptoethanol in PBS (pH 7.2) at 70° C. for 30 minutes, followed by sonication in $H_2O$ for another 45 minutes. The T3 CLIPS carrying peptides were made in a similar way but with three cysteines.

Linear and CLIPS peptides were chemically synthesized according to the following designs:

| Mimic Type | |
|---|---|
| Set 1 | |
| Discontinuous epitope mimics | |
| Label | MAT.A, MAT.B |
| Description | Constrained peptide mimics of varying length. From the two starting sequences (SEQ ID NO: 17 and SEQ ID NO: 18) all 10 to 22, and 10 to 18 mer peptides with stepsize 4 have been made, and these have been paired. At the termini and in between the two peptides cysteines are placed. These are linked by a T3 CLIPS. |
| Set 2 | |
| Linear peptides | |
| Label | RN.PKVNPQGPGPEEKRR (SEQ ID NO: 19) |
| Description | Substitution analysis, starting from the base sequence PKVNPQGPGPEEKRR (SEQ ID NO: 20), all individual amino acids are replaced by all naturally occurring amino acids, except cysteine. |
| Set 3 | |
| Constrained peptides. | |
| Label | RN.PKVNPQGPGPEEKRR_LOOP (SEQ ID NO: 19), RN.ELCTQNCRAFRDLYS_heli3 (SEQ ID NO: 21) RN.ELCTQNCRAFRDLYS_LOOP (SEQ ID NO: 21) |
| Description | Substitution analyses, starting from the base sequences as indicated in the label names, all individual amino acids are replaced by all naturally occurring amino acids, except cysteine. |

ELISA Screening

The binding of antibody to each of the synthesized peptides was tested in a PEPSCAN-based ELISA. The peptide arrays were incubated with primary antibody solution (overnight at 4° C.). After washing, the peptide arrays were incubated with a 1/1000 dilution of an antibody peroxidase conjugate (SBA, cat.nr.2010-05) for one hour at 25° C. After washing, the peroxidase substrate 2,2'-azino-di-3-ethylbenzthiazoline sulfonate (ABTS) and 2 µl/ml of 3 percent H2O2 were added. After one hour, the color development was measured. The color development was quantified with a charge coupled device (CCD)—camera and an image processing system.

Data Processing

The values obtained from the CCD camera range from 0 to 3000 mAU, similar to a standard 96-well plate ELISA-reader. The results are quantified and stored into the Peplab database. Occasionally a well contains an air-bubble resulting in a false-positive value, the cards are manually inspected and any values caused by an air-bubble are scored as 0.

Synthesis Quality Control

To verify the quality of the synthesized peptides, a separate set of positive and negative control peptides was synthesized in parallel. These were screened with antibody 57.9 (ref. Posthumus et al., J. Virology, 1990, 64:3304-3309).

Screening Details

Table 7 summarises antibody binding conditions. For the Pepscan Buffer and Pre-conditioning (SQ), the numbers indicate the relative amount of competing protein (a combination of horse serum and ovalbumin).

TABLE 7

| | screening conditions | | |
|---|---|---|---|
| serum | dilution | samplebuffer | preconditioning |
| MIL-38 AM4 | 10 µg/ml | 10% SQ | 50% SQ |

Results

Primary Experimental Results and Signal to Noise Ratio Determination

A graphical overview of the complete dataset of raw ELISA results generated by the screening is shown in FIG. 13. Here a box plot depicts each dataset and indicates the average ELISA signal, the distribution and the outliers within each dataset. Depending on experiment conditions (amount of antibody, blocking strength etc) different distributions of ELISA data are obtained.

Antibody MIL 38-AM4

In earlier analyses carried out by the present inventors it was established that MIL 38-AM4 binds glypican on stretch 348VNPQGPGPEEK$_{358}$ (SEQ ID NO: 22), and also binds to the stretch $_{135}$TQNARA$_{140}$ (SEQ ID NO: 8)/$_{135}$TQNARAFRD$_{143}$ (SEQ ID NO: 9), which was taken as an indication for a discontinuous epitope.

The looped constructs containing the main stretch pinpoint the residues that are most critical to binding. The results of this study demonstrated that residues V348, Q351, G352, and P353 do not tolerate replacement, with significant requirement for K347, N349 and P350, and to a lesser extent from G354, P355, and E356 (FIG. 14).

Conclusions

The conformational epitope of antibody MIL38-AM4 was profiled.

Leads obtained in earlier analyses that point to a discontinuous epitope for MIL38—AM4 were used to generate a matrix array in which the loops have different lengths. In addition, full substitution analyses of the individual lead sequences were made. All arrays were probed with MIL38-AM4 antibody.

For recognition of glypican-1, the MIL38—AM4 antibody investigated in this study binds to an epitope that exclusively or mainly consists of the flexible loop between residues 347 and 358.

Monoclonal antibody MIL38-AM4 mainly binds glypican-1 on the loop between residues 347-355, but this antibody clearly benefits from the addition of residues from the range 135-140 or 135-143 to the peptide.

TABLE 8

Epitope of the MIL38-AM4 antibody

| Antibody | Epitope | Most important residues | Conformation sensitive |
|---|---|---|---|
| MIL38-AM4 | $_{347}$KVNPQGPGP$_{355}$ (SEQ ID NO: 7) | V348, Q351, G352, P353 | Y |

Unless defined otherwise, all technical and scientific terms herein have the same meaning as commonly understood by one of ordinary skill in the art to which this invention belongs. Although any methods and materials, similar or equivalent to those described herein, can be used in the practice or testing of the present invention, the preferred methods and materials are described herein. All publications, patents, and patent publications cited are incorporated by reference herein in their entirety for all purposes.

The publications discussed herein are provided solely for their disclosure prior to the filing date of the present application. Nothing herein is to be construed as an admission that the present invention is not entitled to antedate such publication by virtue of prior invention.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

REFERENCES

Aikawa T, Whipple C, Lopez M, Gunn J, Young A, Lander A, Korc M. 2008. "Glypican-1 modulates the angiogenic and metastatic potential of human and mouse cancer cells" The Journal of Clinical Investigation Vol 118:1

Borrebaeck et al., 1995 Antibody Engineering: A Practical Approach (Borrebaeck, C, ed.), 1995, Oxford University Press, Oxford; J. Immunol. 149, 3914-3920 (1992)

Cole et al., 1985, in Monoclonal Antibodies and Cancer Therapy, Alan R. Liss, Inc., pp. 77-96

Dainak M, Kumar A, Galaev I Y, Mattiasson B. 2007 "Methods in Cell Separations" Vol 106:1-18

David G, Lories V, Decock B, Marynen P, Cassiman J J, Van den Berghe H. 1990. "Molecular Cloning of a Phosphatidylinositol-anchored Membrane Heparan Sulfate Proteoglycan from Human Lung Fibroblasts" The Journal of Cell Biology Vol 111:6-2 3165-3176

Filmus J, Capurro M, Rast J. "Glypicans" Genome Biology 2008, 9:224

Filmus J, Selleck S B: Glypicans: proteoglycans with a surprise. J Clin Invest 2001, 108:497-501.

Fujise M, Takeo S, Kamimura K, Matsuo T, Aigaki T, Izumi S, Nakato H. Dally regulates DPP morphogen gradient formation in the *Drosophila* wing. Development 2003, 130:1515-1522.

Han C, Belenkaya T Y, Wang B, Lin X. "*Drosophila* glypicans control the cell-to-cell movement of hedgehog by a dynamin-independent process". Development 2004, 131:601-611.

Harlow et al 1988. Antibodies, A Laboratory Manual, Ed Harlow and David Lane, Cold Spring Harbor Laboratory (1988), Cold Spring Harbor, N.Y.

Harmon J Eyre, Robert A Smith, and Curtis J Mettlin, "Chapter 28 Cancer Screening and Early Detection" Holland-Frei Cancer Medicine 5' Edition. Bast R C Jr, Kufe D W, Pollock R E, editors Hamilton (ON): BC Decker; 2000.

Hoffman R., Gililand F., Cameron M., Hunt W., and Key C. "Prostate-specific antigen testing accuracy in community practice" BMC Fam Pract. 2002, 3:19.

Holliger P and Hudson P. 2005. "Engineered antibody fragments and the rise of single domains" Nature Biotech 23 1126-1136.

Johnson K W, Dooner M, Queensberry P J. 2007 "Fluorescence Activated Cell Sorting: A Window on the Stem Cell" Vol 8:133-9

Kleef J, Ishiwata T, Kumbasar A, Friess H, Buchler M, Lander A. "The Cell-surface haparan sulfate proteoglycan glypican-1 regulated growth factor action in pancreatic carcinoma cells and is overexpressed in human pancreatic cancer" J Clin Invest. Vol 102 No 9 Nov. 1998

Kohler and Milstein 1975 Continuous cultures of fused cells secreting antibody of predefined specificity Nature 256: 495-497

Matsuda K, Maruyama H, Guo F, Kleef J, Matsumodto Y, Lander A D, Korc M. "Glypican-1 is overexprssed in human breast cancer and modulates the mitogenic effects of multiple heparin-binding growth factors in breast cancer cells." Cancer Res 2001 Jul. 15, 61(14)5562-9.

Orfao A, Ruiz-arguelles, Alejandro. 1996 "General concepts about cell sorting techniques" Clin. Biochem. Vol 29:1 5-9

Qiao D, Meyer K, Mundhenke C, Friedl S, Friedl D. 2003 "Heparan Sulfate Proteoglycans as Regulators of Fibroblast Growth Factor-2 Signaling in Brain Endothelial Cells: SPECIFIC: ROLE FOR GLYPICAN-1 IN GLIOMA ANGIOGENESIS" J. Biol. Chem. 16045-16053.

Rotmans et al. 1983 Cross-linking of *Schistosoma mansoni* antigens and their covalent binding on the surface of polystyrene microtitration trays for use in the ELISA J. Immunol. Methods 57:87-98 (1983)

Russell P J., Ow K T., Tam P N., Juarez E A., Qu C F., Li Y., Cozzi P J., and Martiniello-Wilks. "Immunohistochemical characterization of the monoclonal antibody BLCA-38 for the detection of prostate cancer" Cancer Immunol. Immunoother (2004) 53: 995-1004

Spaltro, Andrea Doctoral Dissertation University of Bologna 2012

Su G, Meyer, K, Nandini C, Qiao D, Salamat S, Friedl A. "Glypican-1 is frequently overexpressed in human gliomas and enhances FGF-2 signaling in glioma cells" Am J Pathol 2006 June 168(6) 2014-2026.

Suhovskih A, MostovichL, Kunin I, Mekhrozhiddin B, Nepomnyashchikh G, Aidaulova S, Griorieva E. "Proteoglycan expression in normal human prostate tissue and prostate cancer" Oncology Volume 2013 ID 680136

Tung Jw, Heydari K, Tirouvanziam R, Sahaf B, Parks D R, Herzenberg L A. 2007 "Modern Flow Cytometry: A Practical Approach" Vol 27:453-68

Veugelers M, De Cat B, Ceulemans H, Bruystens A M, Coomans C, Durr J, Vermeesch J, Marynen P, David G. "Glypican-6, a new member of the glypican family of cell surface proteoglycans." J Biol Chem 1999 274:26968-26977

Walker K Z, Russell P J, Kingsley E A, Philips J, Raghavan D. "Detection of maliganant cells in voided urine from patients with bladder cancer, a novel monoclonal assay. J Urol 142:1578 1989.

Whipple C, Yong A, RLATG, Korc M. 2012. "A Kras$^{G12D}$-driven Genetic Mouse Model of Pancreatic Cancer Requires Glypican-1 for Efficient Proliferation and Angiogenesis" Ocogene May 17 31(20) 2535-2544.

The invention claimed is:

1. A method of detecting prostate cancer in a patient, the method comprising measuring the level of soluble glypican-1 in a body fluid sample from a patient and determining that said patient has prostate cancer based upon the level of soluble glypican-1 in the body fluid sample, wherein:
   the measuring of soluble glypican-1 in the body fluid sample comprises contacting the body fluid sample with a population of anti-glypican-1 antibodies, and
   the population of anti-glypican-1 antibodies comprise:
   (a) a heavy chain variable region comprising:
   a complementarity determining region 1 (CDR1) comprising the amino acid sequence positions 50-54 of SEQ ID NO: 10;
   a complementarity determining region 2 (CDR2) comprising the amino acid sequence positions 69-85 of SEQ ID NO: 10;
   a complementarity determining region 3 (CDR3) comprising the amino acid sequence positions 118-126 of SEQ ID NO: 10; and
   (b) a light chain variable region comprising:
   a complementarity determining region 1 (CDR1) comprising the amino acid sequence positions 44-54 of SEQ ID NO: 11;
   a complementarity determining region 2 (CDR2) comprising the amino acid sequence positions 70-76 of SEQ ID NO: 11;
   a complementarity determining region 3 (CDR3) comprising the amino acid sequence positions 109-117 of SEQ ID NO: 11.

2. The method of detecting prostate cancer in a patient of claim 1, comprising the steps of:
   (a) obtaining a body fluid sample from a patient;
   (b) contacting said body fluid sample with the population of anti-glypican-1 antibodies of claim 1; and
   (c) determining that said patient has prostate cancer based upon binding of the population of anti-glypican-1 antibodies to said body fluid sample.

3. The method of claim 2, wherein the population of anti-glypican-1 antibodies are not used in combination with antibodies comprising a light chain variable region comprising:
   a complementarity determining region 1 (CDR1) comprising the amino acid sequence positions 48-58 of SEQ ID NO: 12;
   a complementarity determining region 2 (CDR2) comprising the amino acid sequence positions 74-80 of SEQ ID NO: 12; and/or
   a complementarity determining region 3 (CDR3) comprising the amino acid sequence positions 113-121 of SEQ ID NO: 12.

4. The method of claim 3, wherein the population of anti-glypican-1 antibodies are produced by or otherwise identical to an antibody population as generated by hybridoma cells deposited on 22 Aug. 2014 at CellBank Australia (CBA) under accession number CBA20140026.

5. The method of claim 2, wherein the population of anti-glypican-1 antibodies comprises antibody fragments or recombinant antibodies capable of binding glypican-1.

6. The method of claim 1, wherein the population of anti-glypican-1 antibodies are labeled.

7. The method of claim 6, wherein said label is chosen from a group consisting of a radiolabel, a fluorescent label, a biotin-avidin amplification system, a chemiluminescence system, microspheres, and colloidal gold.

8. The method of claim 1, wherein binding of the population of anti-glypican-1 antibodies to soluble glypican-1 in the body fluid sample is detected via a technique selected from the group consisting of immunofluorescence, radiolabeling, immunoblotting, Western blotting, enzyme-linked immunosorbent assay (ELISA), flow cytometry, immunoprecipitation, immunohistochemistry, biofilm test, affinity ring test, antibody array optical density test, and chemiluminescence.

9. The method of claim 1, wherein said level of glypican-1 in the body fluid sample from a patient is compared to the level of glypican-1 in a control sample; wherein increased anti-glypican-1 antibody binding of the body fluid sample over the control sample is associated with the presence of prostate cancer.

10. The method of claim 9, wherein a 50% or more increase in the level of glypican-1 of said body fluid sample over the level of glypican-1 in the control sample is indicative of prostate cancer.

11. The method of claim 1, wherein binding of the anti-glypican-1 antibodies to said body fluid sample is compared to binding of anti-glypican-1 antibodies in a control sample; wherein increased anti-glypican-1 antibody binding of the body fluid sample over the control sample is associated with the presence of prostate cancer.

12. The method of claim 11, wherein a 50% or more increase in the anti-glypican-1 antibody binding to said body fluid sample over the level of anti-glypican-1 antibody binding of the control sample is indicative of prostate cancer.

13. The method of claim 1, wherein binding of the population of anti-glypican-1 antibodies to said body fluid sample is compared to binding of the population of anti-glypican-1 antibodies to one or more glypican-1 standards; wherein the anti-glypican-1 antibody binding of the standards is used to quantify the amount of glypican-1 in said body fluid sample.

14. The method of claim 1, wherein a glypican-1 content higher than about 10 ng/ml in the body fluid sample is indicative of prostate cancer.

15. The method of claim 1, further comprising:
measuring the level of prostate-specific antigen (PSA) in a body fluid sample from the patient, and determining that said patient has prostate cancer based upon (i) the level of PSA measured in the body fluid sample, and (ii) binding of said anti-glypican-1 antibody to said body fluid sample.

16. The method of claim 15, wherein the level of prostate-specific antigen (PSA) is measured in a blood sample from the patient.

17. The method of claim 15, wherein the level of prostate-specific antigen (PSA) in the body fluid sample measured is compared to the level of PSA measured in a control sample; wherein increased PSA levels in the body fluid sample over the control sample is associated with the presence of prostate cancer.

18. The method of claim 1, wherein said body fluid is selected from the group consisting of blood, serum, plasma, and urine.

* * * * *